United States Patent
Dorsey et al.

(10) Patent No.: US 11,987,624 B2
(45) Date of Patent: May 21, 2024

(54) HUMAN MONOCARBOXYLATE TRANSPORTER 1 ANTIBODIES AND USES THEREOF

(71) Applicant: Immunometabolism Development Company, LLC, Indianapolis, IN (US)

(72) Inventors: Frank Charles Dorsey, Indianapolis, IN (US); Joseph Benjamin Granger, Indianapolis, IN (US); Kira Vladimirovna Rubtsova, San Diego, CA (US); Oliver Schroeder, Encinitas, CA (US); Wei Wang, Zionsville, IN (US)

(73) Assignee: Immunometabolism Development Company, LLC, Indianapolis, IN (US)

(*) Notice: Subject to any disclaimer, the term of this patent is extended or adjusted under 35 U.S.C. 154(b) by 0 days.

(21) Appl. No.: 17/932,039

(22) Filed: Sep. 14, 2022

(65) Prior Publication Data

US 2023/0111363 A1 Apr. 13, 2023

Related U.S. Application Data

(60) Provisional application No. 63/272,903, filed on Oct. 28, 2021, provisional application No. 63/261,177, filed on Sep. 14, 2021.

(51) Int. Cl.
*C07K 16/28* (2006.01)
*A61P 37/00* (2006.01)
*C12N 15/85* (2006.01)

(52) U.S. Cl.
CPC .............. *C07K 16/28* (2013.01); *A61P 37/00* (2018.01); *C12N 15/85* (2013.01); *C07K 2317/565* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 2004/0132813 A1 | 7/2004 | Broeks |
| 2014/0193436 A1 | 7/2014 | Prudent |
| 2017/0355987 A1 | 12/2017 | Mauro et al. |
| 2019/0263931 A1* | 8/2019 | Rothstein ............... C07K 16/40 |

FOREIGN PATENT DOCUMENTS

WO 2019/136300 A2 7/2019

OTHER PUBLICATIONS

International Searching Authority, International Search Report and Search Report, and Search Strategy for PCT/US2019/12415, dated Jun. 28, 2019.
Written Opinion of the International Searching Authority for PCT/US2019/12415, dated Jun. 28, 2019.
Balasubramaniam, S, "Heterozygous Monocarboxylate Transporter 1 (MCT1, SLC16A1) Deficiency as a Cause of Recurrent Ketoacidosis", JIMD Rep. 2016;29:33-81.
Doherty, Jr, "Blocking Lactate Export by Inhibiting the Myc Target MCT1 Disables Glycolysis and Glutathione Synthesis", Cancer Research. 2014;74(3):908-20.
Fischer, K, "Inhibitory effect of tumor cell—derived lactic acid on human T cells", Blood. 2007;109(9):3812-9).
Halestrap, AP, "The Monocarboxylate Transporter Family—Structure and Functional Characterization", IUBMB Life. 2012;64(1):1-9).
Philip NJ, "Loss of MCT1, MCT3 and MCT4 Expression in the Retinal Pigment Epithelium and Neural Retina of the 5A11/Basigin-Null Mouse", Investigative Ophthalmology & Visual Science. 2003, 44(3):1305-11.
Van Hasselt PM, "Monocarboxylate Transporter 1 Deficiency and Ketone Utilization", N Engl J Med. 2014, 371(20):1900-7.
Wang, R, "The Transcription Factor Myc Controls Metabolic Reprogramming upon T Lymphocyte Activation", Immunity. 2011;35(6):871-82).
Yin Y, "Normalization of CD4+ T cell metabolism reverses lupus", Sci Transl Med. 2015;7(274):274ra18.

* cited by examiner

*Primary Examiner* — Daniel E Kolker
*Assistant Examiner* — Hilary Ann Petrash
(74) *Attorney, Agent, or Firm* — Dipa Patel

(57) ABSTRACT

The present invention relates to antibodies that specifically bind human monocarboxylate transporter 1 (MCT1) ("anti-human MCT1 antibodies"), compositions comprising such anti-human MCT1 antibodies, and methods of using such anti-human MCT1 antibodies.

34 Claims, 9 Drawing Sheets

Specification includes a Sequence Listing.

SEQUENCE LISTING

Sequence total quantity: 99
SEQ ID NO: 1        moltype = AA  length = 13
FEATURE             Location/Qualifiers
source              1..13
                       mol_type = protein
                       organism = synthetic construct
SEQUENCE: 1
TVSGFSLTNY HLQ                                    13

```
SEQ ID NO: 2               moltype = AA   length = 16
FEATURE                    Location/Qualifiers
source                     1..16
                           mol_type = protein
                           organism = synthetic construct
SEQUENCE: 2
FIRSSGNTEY NSEFKS                                                           16

SEQ ID NO: 3               moltype = AA   length = 20
FEATURE                    Location/Qualifiers
source                     1..20
                           mol_type = protein
                           organism = synthetic construct
SEQUENCE: 3
ARNSWYHGTY YSPGYYVMDA                                                       20

SEQ ID NO: 4               moltype = AA   length = 11
FEATURE                    Location/Qualifiers
source                     1..11
                           mol_type = protein
                           organism = synthetic construct
SEQUENCE: 4
KGSQNINNYL A                                                                11

SEQ ID NO: 5               moltype = AA   length = 8
FEATURE                    Location/Qualifiers
source                     1..8
                           mol_type = protein
                           organism = synthetic construct
SEQUENCE: 5
YNRHNLQT                                                                    8

SEQ ID NO: 6               moltype = AA   length = 8
FEATURE                    Location/Qualifiers
source                     1..8
                           mol_type = protein
                           organism = synthetic construct
SEQUENCE: 6
YQYSDGYT                                                                    8

SEQ ID NO: 7               moltype = AA   length = 126
FEATURE                    Location/Qualifiers
source                     1..126
                           mol_type = protein
                           organism = synthetic construct
SEQUENCE: 7
QVQLVQSGAE VKKPGASVKV SCTVSGFSLT NYHLQWVRQA PGQGLEWMGF IRSSGNTEYN            60
SEFKSRVTMT RDTSTSTVYM ELSSLRSEDT AVYYCARNSW YHGTYYSPGY YVMDAWGQGT           120
LVTVSS                                                                    126

SEQ ID NO: 8               moltype = AA   length = 106
FEATURE                    Location/Qualifiers
source                     1..106
                           mol_type = protein
                           organism = synthetic construct
SEQUENCE: 8
EIVLTQSPGT LSLSPGERAT LSCKGSQNIN NYLAWYQQKP GQAPRLLIYN RHNLQTGIPD            60
RFSGSGSGTD FTLTISRLEP EDFAVYYCYQ YSDGYTFGGG TKVEIK                         106

SEQ ID NO: 9               moltype = AA   length = 456
FEATURE                    Location/Qualifiers
source                     1..456
                           mol_type = protein
                           organism = synthetic construct
SEQUENCE: 9
QVQLVQSGAE VKKPGASVKV SCTVSGFSLT NYHLQWVRQA PGQGLEWMGF IRSSGNTEYN            60
SEFKSRVTMT RDTSTSTVYM ELSSLRSEDT AVYYCARNSW YHGTYYSPGY YVMDAWGQGT           120
LVTVSSASTK GPSVFPLAPS SKSTSGGTAA LGCLVKDYFP EPVTVSWNSG ALTSGVHTFP           180
AVLQSSGLYS LSSVVTVPSS SLGTQTYICN VNHKPSNTKV DKRVEPKSCD KTHTCPPCPA           240
PEAEGAPSVF LFPPKPKDTL MISRTPEVTC VVVDVSHEDP EVKFNWYVDG VEVHNAKTKP           300
REEQYNSTYR VVSVLTVLHQ DWLNGKEYKC KVSNKALPSS IEKTISKAKG QPREPQVYTL           360
PPSREEMTKN QVSLTCLVKG FYPSDIAVEW ESNGQPENNY KTTPPVLDSD GSFFLYSKLT           420
VDKSRWQQGN VFSCSVMHEA LHNHYTQKSL SLSPGK                                    456

SEQ ID NO: 10              moltype = AA   length = 213
FEATURE                    Location/Qualifiers
source                     1..213
                           mol_type = protein
```

```
                          organism = synthetic construct
SEQUENCE: 10
EIVLTQSPGT LSLSPGERAT LSCKGSQNIN NYLAWYQQKP GQAPRLLIYN RHNLQTGIPD    60
RFSGSGSGTD FTLTISRLEP EDFAVYYCYQ YSDGYTFGGG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 11           moltype = DNA   length = 1368
FEATURE                 Location/Qualifiers
source                  1..1368
                        mol_type = other DNA
                        organism = synthetic construct
SEQUENCE: 11
caagtccaac tggtgcaatc tggggcagag gtaaagaagc ctggcgcatc agtaaaggta    60
agttgcactg taagcgggtt ctcactcaca aactaccatc tgcaatgggt tcgacaagct   120
ccagggcaag gcttggaatg gatggggttc ataaggagct ccgggaacac agaatataac   180
agcgagttca agtcacgagt cacaatgaca cgggacacct caacctcaac agtttacatg   240
gaattgtctt cattgcgtag tgaggacacc gccgtttact actgtgctag gaactcctgg   300
tatcacggta cctactattc tcctggctat tatgtaatgg atgcttgggg ccaggggact   360
ctggtaaccg tttcctccgc ctccaccaag ggcccatcgg tcttccccct ggcaccctcc   420
tccaagagca cctctggggg cacagcggcc ctgggctgcc tggtcaagga ctacttccc    480
gaaccggtga cggtgtcgtg gaactcaggc gcactgacca gcggcgtgca caccttcccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagagag ttgagcccaa atcttgtgac aaaactcaca catgcccacc gtgcccagca   720
cctgaaccg agggggcacc gtcagtcttc ctcttccccc caaaacccaa ggacaccctc   780
atgatctccc ggacccctga ggtcacatgc gtggtggtgg acgtgagcca cgaagaccct   840
gaggtcaagt tcaactggta tgtggacggc gtggaggtgc ataatgccaa gacaaagccg   900
cgggaggagc agtacaacag cacgtaccgt gtggtcagcg tcctcaccgt cctgcaccaa   960
gactggctga atggcaagga gtacaagtgc aaggtctcca acaaagccct cccatcctcc  1020
atcgagaaaa ccatctccaa agccaaaggg cagccccgag aaccacaggt gtacaccctg  1080
cccccatccc gggaggagat gaccaagaac caagtcagcc tgacctgcct ggtcaaaggc  1140
ttctatccca gcgacatcgc cgtggagtgg gagagcaatg ggcagccgga gaacaactac  1200
aagaccacgc ctcccgtgct ggactccgac ggctccttct tcctctattc aagctcacc  1260
gtggacaaga gcaggtggca gcaggggaac gtcttctcat gctccgtgat gcatgaggct  1320
ctgcacaacc actacacgca gaagagcctc tccctgtctc cgggcaaa              1368

SEQ ID NO: 12           moltype = DNA   length = 639
FEATURE                 Location/Qualifiers
source                  1..639
                        mol_type = other DNA
                        organism = synthetic construct
SEQUENCE: 12
gagatcgtcc tcacccagtc tcccggcaca ttgagtttga gtccaggtga aagagcaaca    60
ctgagctgca aagtagcca gaacataaat aattatcttg catggtacca gcagaaacct   120
gggcaggcac ccaggctctt gatctacaat aggcataacc tgcagacagg cattcctgat   180
agattttctg gatcaggtag tggtaccgac tttacccttac catctcacg actggagcct   240
gaagattttg ccgtctatta ctgttatcaa tacagcgatg gttacacttt cggggggagg   300
acaaaagtgg aaataaagcg aaccgtggct gcaccatctg tcttcatctt cccgccatct   360
gatgagcagt tgaaatctgg aactgcctct gttgtgtgcc tgctgaataa cttctatccc   420
agagagccca aagtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgc                         639

SEQ ID NO: 13           moltype = AA    length = 106
FEATURE                 Location/Qualifiers
source                  1..106
                        mol_type = protein
                        organism = synthetic construct
SEQUENCE: 13
DIQMTQSPST LSASVGDRVT ITCKGSQNIN NYLAWYQQKP GKAPKLLIYN RHNLQTGVPS    60
RFSGSGSGTE FTLTISSLQP DDFATYYCYQ YSDGYTFGGG TKVEIK                  106

SEQ ID NO: 14           moltype =    length =
SEQUENCE: 14
000

SEQ ID NO: 15           moltype = AA   length = 213
FEATURE                 Location/Qualifiers
source                  1..213
                        mol_type = protein
                        organism = synthetic construct
SEQUENCE: 15
DIQMTQSPST LSASVGDRVT ITCKGSQNIN NYLAWYQQKP GKAPKLLIYN RHNLQTGVPS    60
RFSGSGSGTE FTLTISSLQP DDFATYYCYQ YSDGYTFGGG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213
```

```
SEQ ID NO: 16            moltype =    length =
SEQUENCE: 16
000

SEQ ID NO: 17            moltype = DNA   length = 639
FEATURE                  Location/Qualifiers
source                   1..639
                         mol_type = other DNA
                         organism = synthetic construct
SEQUENCE: 17
gatattcaga tgacacagag cccttccacc ctgagcgcca gtgtaggcga ccgggtaact    60
ataacatgta aaggctcaca aaacatcaat aactatttgg cctggtatca gcaaaagcca   120
ggaaaagctc ctaaactctt gatatacaac agacataact tgcaaactgg ggtgccaagt   180
cgcttcagcg ggagtggctc aggtacagag tttactctta ccattcctc cctgcaacct   240
gacgattttg ccacctacta ttgctaccaa tattccgatg gatacacttt cggggggtgg   300
actaaagttg agattaagcg aaccgtggct gcaccatctg tcttcatctt cccgccatct   360
gatgagcagt tgaaatctgg aactgcctct gttgtgtgcc tgctgaataa cttctatccc   420
agagaggcca aagtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgc                          639

SEQ ID NO: 18            moltype = AA  length = 126
FEATURE                  Location/Qualifiers
source                   1..126
                         mol_type = protein
                         organism = synthetic construct
SEQUENCE: 18
EVQLVESGGG LVQPGGSLRL SCTVSGFSLT NYHLQWVRQA PGKGLEWVGF IRSSGNTEYN    60
SEFKSRFTIS RDDSKNSLYL QMNSLKTEDT AVYYCARNSW YHGTYYSPGY YVMDAWGQGT   120
LVTVSS                                                              126

SEQ ID NO: 19            moltype = AA  length = 456
FEATURE                  Location/Qualifiers
source                   1..456
                         mol_type = protein
                         organism = synthetic construct
SEQUENCE: 19
EVQLVESGGG LVQPGGSLRL SCTVSGFSLT NYHLQWVRQA PGKGLEWVGF IRSSGNTEYN    60
SEFKSRFTIS RDDSKNSLYL QMNSLKTEDT AVYYCARNSW YHGTYYSPGY YVMDAWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKRVEPKSCD KTHTCPPCPA   240
PEAEGAPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPSS IEKTISKAKG QPREPQVYTL   360
PPSREEMTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGK                             456

SEQ ID NO: 20            moltype = DNA   length = 1368
FEATURE                  Location/Qualifiers
source                   1..1368
                         mol_type = other DNA
                         organism = synthetic construct
SEQUENCE: 20
gaagtccaac ttgtagaatc tgggggagga ctggtccaac ctggcggcag cctgcgactg    60
tcttgcactg tcagtggatt tccctcacc aactaccatc ttcaatgggt ccgacaagcc   120
cccggaaaag gactggaatg ggtgggcttc ataagatcaa gtggtaacac agagtacaac   180
tcagaattca agtcacgttt taccataagc gcgatgaca gcaaaaatag cttgtacctt   240
caaatgaact ctctcaagac cgaggatacc gccgtgtatt actgcgctcg aatagctgg   300
taccacggaa catattactc tcccggttac tatgttatgg acgcttgggg gcagggtaca   360
ttggttaccg tctccagcgc ctccaccaag ggcccatcgg tcttcccct ggcaccctcc   420
tccaagagca cctctggggg cacagcggcc ctgggctgcc tggtcaagga ctacttcccc   480
gaaccggtga cggtgtcgtg gaactcaggc gcactgacca gcggcgtgca caccttcccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagagag ttgagcccaa atcttgtgac aaaactcaca catgcccacc gtgcccagca   720
cctgaagccg aggggcacc gtcagtcttc ctcttccccc caaaacccaa ggacaccctc   780
atgatctccc ggaccctga ggtcacatgc gtggtggtgg acgtgagcca cgaagaccct   840
gaggtcaagt tcaactggta tgtggacggc gtggaggtgc ataatgccaa gacaaagccg   900
cgggaggagc agtacaacag cacgtaccgt gtggtcagcg tcctcaccgt cctgcaccaa   960
gactggctga atggcaagga gtacaagtgc aaggtctcca acaaagccct cccatcctcc  1020
atcgagaaaa ccatctccaa agccaaaggg cagccccgag aaccacaggt gtacaccctg  1080
cccccatccc gggaggagat gaccaagaac caagtcagcc tgacctgcct ggtcaaaggc  1140
ttctatccca gcgacatcgc cgtggagtgg gagagcaatg gcagccggga gaacaactac  1200
aagaccacgc ctcccgtgct ggactccgac ggctccttct tcctctattc caagctcacc  1260
gtggacaaga gcaggtggca gcaggggaac gtcttctcat gctccgtgat gcatgaggct  1320
ctgcacaacc actacacgca gaagagcctc tccctgtctc cgggcaaa               1368

SEQ ID NO: 21            moltype = AA  length = 126
FEATURE                  Location/Qualifiers
```

```
source                  1..126
                        mol_type = protein
                        organism = synthetic construct
SEQUENCE: 21
EVQLVESGGG LVKPGGSLRL SCTVSGFSLT NYHLQWVRQA PGKGLEWVGF IRSSGNTEYN    60
SEFKSRFTIS RDDSKNTLYL QMNSLKTEDT AVYYCARNSW YHGTYYSPGY YVMDAWGQGT   120
LVTVSS                                                              126

SEQ ID NO: 22           moltype = AA  length = 106
FEATURE                 Location/Qualifiers
source                  1..106
                        mol_type = protein
                        organism = synthetic construct
SEQUENCE: 22
DIQMTQSPSS LSASVGDRVT ITCKGSQNIN NYLAWYQQKP GKAPKLLIYN RHNLQTGVPS    60
RFSGSGSGTD FTLTISSLQP EDFATYYCYQ YSDGYTFGGG TKVEIK                  106

SEQ ID NO: 23           moltype = AA  length = 456
FEATURE                 Location/Qualifiers
source                  1..456
                        mol_type = protein
                        organism = synthetic construct
SEQUENCE: 23
EVQLVESGGG LVKPGGSLRL SCTVSGFSLT NYHLQWVRQA PGKGLEWVGF IRSSGNTEYN    60
SEFKSRFTIS RDDSKNTLYL QMNSLKTEDT AVYYCARNSW YHGTYYSPGY YVMDAWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKRVEPKSCD KTHTCPPCPA   240
PEAEGAPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPSS IEKTISKAKG QPREPQVYTL   360
PPSREEMTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGK                             456

SEQ ID NO: 24           moltype = AA  length = 213
FEATURE                 Location/Qualifiers
source                  1..213
                        mol_type = protein
                        organism = synthetic construct
SEQUENCE: 24
DIQMTQSPSS LSASVGDRVT ITCKGSQNIN NYLAWYQQKP GKAPKLLIYN RHNLQTGVPS    60
RFSGSGSGTD FTLTISSLQP EDFATYYCYQ YSDGYTFGGG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 25           moltype = DNA  length = 1368
FEATURE                 Location/Qualifiers
source                  1..1368
                        mol_type = other DNA
                        organism = synthetic construct
SEQUENCE: 25
gaagtccagc tggtagaatc tggtggtggg ttggtcaaac ccggcgggag ccttagactg    60
tcatgtactg tatcaggttt ttcattgaca aattatcatc tccagtgggt acgacaagcc   120
cctggaaagg ggctcgaatg ggtaggtttt atcagaagtt caggcaacac agaatacaac   180
tcagagttca gtctcgtttt taccataagc cgcgatgact ctaaaaacac actgtacctt   240
cagatgaact ctctcaagac cgaagacacc gccgtctact attgcgctag aaatagttgg   300
taccatggta catactactc tcctggatat tacgtcatgg acgcctgggg ccaggggact   360
cttgtgacag tttcctccgc ctccaccaag ggcccatcgg tcttcccct  ggcaccctcc   420
tccaagagca cctctggggg cacagcggcc ctgggctgcc tggtcaagga ctacttcccc   480
gaaccggtga cggtgtcgtg gaactcaggc gcactgacca gcggcgtgca cacctteccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagagag ttgagcccaa atcttgtgac aaaactcaca catgcccacc gtgcccagca   720
cctgaagccg aggggcacc  gtcagtcttc ctcttcccc  caaacccaa  ggacaccctc   780
atgatctccc ggacccctga ggtcacatgc gtggtggtgg acgtgagcca cgaagaccct   840
gaggtcaagt tcaactggta tgtggacggc gtggaggtgc ataatgccaa gacaaagccg   900
cgggaggagc agtacaacag cacgtaccgt gtggtcagcg tcctcaccgt cctgcaccaa   960
gactggctga atggcaagga gtacaagtgc aaggtctcca acaaagccct cccatcctcc  1020
atcgagaaaa ccatctccaa agccaaaggg cagccccgag aaccacaggt gtacaccctg  1080
cccccatccc gggaggagat gaccaagaac caagtcagcc tgacctgcct ggtcaaaggc  1140
ttctatccca gcgacatcgc cgtggagtgg gagagcaatg ggcagccgga gaacaactac  1200
aagaccacgc ctcccgtgct ggactccgac ggctccttct tcctctattc caagctcacc  1260
gtggacaaga gcaggtggca gcaggggaac gtcttctcat gctccgtgat gcatgaggct  1320
ctgcacaacc actacacgca gaagagcctc tccctgtctc cgggcaaa                1368

SEQ ID NO: 26           moltype = DNA  length = 639
FEATURE                 Location/Qualifiers
source                  1..639
                        mol_type = other DNA
                        organism = synthetic construct
SEQUENCE: 26
```

```
gatattcaaa tgacacaatc tccctccagc ctgtcagcct ctgttggaga cagggtaact   60
ataacatgca aaggctccca aaacataaat aattacttgg cctggtatca acagaaacct  120
ggtaaggcac ctaagctgct catctacaat aggcataacc ttcagactgg cgttccttct  180
aggtttagcg ggtcagggtc cggtaccgat tttaccctca caatatccag tcttcaaccc  240
gaggacttcg caacatatta ttgttatcag tattctgatg gttacacctt cggaggggga  300
actaaggtgg agatcaagcg aaccgtggct gcaccatctg tcttcatctt cccgccatct  360
gatgagcagt tgaaatctgg aactgcctct gtttgtgtgc ctgctgaataa cttctatccc  420
agagaggcca agtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgc                         639

SEQ ID NO: 27           moltype = AA  length = 126
FEATURE                 Location/Qualifiers
source                  1..126
                        mol_type = protein
                        organism = synthetic construct
SEQUENCE: 27
EVQLVQSGAE VKKPGESLKI SCTVSGFSLT NYHLQWVRQM PGKGLEWMGF IRSSGNTEYN   60
SEFKSQVTIS ADKSISTAYL QWSSLKASDT AMYYCARNSW YHGTYYSPGY YVMDAWGQGT  120
LVTVSS                                                             126

SEQ ID NO: 28           moltype = AA  length = 456
FEATURE                 Location/Qualifiers
source                  1..456
                        mol_type = protein
                        organism = synthetic construct
SEQUENCE: 28
EVQLVQSGAE VKKPGESLKI SCTVSGFSLT NYHLQWVRQM PGKGLEWMGF IRSSGNTEYN   60
SEFKSQVTIS ADKSISTAYL QWSSLKASDT AMYYCARNSW YHGTYYSPGY YVMDAWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKRVEPKSCD KTHTCPPCPA  240
PEAEGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPSS IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                            456

SEQ ID NO: 29           moltype = DNA  length = 1368
FEATURE                 Location/Qualifiers
source                  1..1368
                        mol_type = other DNA
                        organism = synthetic construct
SEQUENCE: 29
gaggtccaac ttgttcagtc cggtgctgag gtgaaaaagc ctggagaatc actgaaaatt   60
agttgcaccg tatctggctt ttctcttacc aactaccacc tccaatgggt aagacagatg  120
ccagggaaag gtttggagtg gatgggtttc atccggtcct ccggcaacac cgaatataac  180
agtgagttta aaagtcaggt tactatttcc gccgataaag gcatttcaac cgcctacctt  240
cagtggtcca gtttgaaggc atctgacaca gcaatgtatt attgtgctcg aaactcctgg  300
tatcatggaa catactattc accagggtac tacgtgatgg atgcatgggg tcagggtacc  360
ctcgtcacag taagctctgc ctccaccaag ggcccatcgg tcttccccct ggcaccctcc  420
tccaagagca cctctggggg cacagcggcc ctgggctgcc tggtcaagga ctacttcccg  480
gaaccggtga cggtgtcgtg gaactcaggc gcactgacca gcggcgtgca caccttcccg  540
gctgtcctac agtcctcagg actctactcc ctcagcagcg tggtgaccgt gccctccagc  600
agcttgggca cccagaccta catctgcaac gtgaatcaca agcccagcaa caccaaggtg  660
gacaagagag ttgagcccaa atcttgtgac aaaactcaca catgcccacc gtgcccagca  720
cctgaagccg aggggggcacc gtcagtcttc ctcttccccc caaaacccaa ggacaccctc  780
atgatctccc ggacccctga ggtcacatgc gtggtggtgg acgtgagcca cgaagaccct  840
gaggtcaagt tcaactggta tgtggacggc gtggaggtgc ataatgccaa gacaaagccg  900
cgggaggagc agtacaacag cacgtaccgt gtggtcagcg tcctcaccgt cctgcaccaa  960
gactggctga atggcaagga gtacaagtgc aaggtctcca acaaagccct cccatcctcc 1020
atcgagaaaa ccatctccaa agccaaaggg cagccccgag aaccacaggt gtacaccctg 1080
cccccatccc gggaggagat gaccaagaac caagtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctattc caagctcacc 1260
gtggacaaga gcaggtggca gcaggggaac gtcttctcat gctccgtgat gcatgaggct 1320
ctgcacaacc actacacgca gaagagcctc tccctgtctc cgggcaaa             1368

SEQ ID NO: 30           moltype = AA  length = 13
FEATURE                 Location/Qualifiers
source                  1..13
                        mol_type = protein
                        organism = synthetic construct
SEQUENCE: 30
TVSGRSLTNY HLQ                                                      13

SEQ ID NO: 31           moltype = AA  length = 16
FEATURE                 Location/Qualifiers
source                  1..16
                        mol_type = protein
```

-continued

```
SEQUENCE: 31
FIRSSGNTEY NSRFKS                                                      16

SEQ ID NO: 32           moltype = AA  length = 20
FEATURE                 Location/Qualifiers
source                  1..20
                        mol_type = protein
                        organism = synthetic construct
SEQUENCE: 32
ARNRWYHGTY YSPGYYVMDA                                                  20

SEQ ID NO: 33           moltype = AA  length = 11
FEATURE                 Location/Qualifiers
source                  1..11
                        mol_type = protein
                        organism = synthetic construct
SEQUENCE: 33
KGSQNIENYL A                                                           11

SEQ ID NO: 34           moltype = AA  length = 126
FEATURE                 Location/Qualifiers
source                  1..126
                        mol_type = protein
                        organism = synthetic construct
SEQUENCE: 34
QVQLVQSGAE VKKPGASVKV SCTVSGRSLT NYHLQWVRQA PGQGLEWMGF IRSSGNTEYN       60
SRFKSRVTMT RDTSTSTVYM ELSSLRSEDT AVYYCARNRW YHGTYYSPGY YVMDAWGQGT      120
LVTVSS                                                                126

SEQ ID NO: 35           moltype = AA  length = 106
FEATURE                 Location/Qualifiers
source                  1..106
                        mol_type = protein
                        organism = synthetic construct
SEQUENCE: 35
EIVLTQSPGT LSLSPGERAT LSCKGSQNIE NYLAWYQQKP GQAPRLLIYN RHNLQTGIPD       60
RFSGSGSGTD FTLTISRLEP EDFAVYYCYQ YSDGYTFGGG TKVEIK                    106

SEQ ID NO: 36           moltype = AA  length = 456
FEATURE                 Location/Qualifiers
source                  1..456
                        mol_type = protein
                        organism = synthetic construct
SEQUENCE: 36
QVQLVQSGAE VKKPGASVKV SCTVSGRSLT NYHLQWVRQA PGQGLEWMGF IRSSGNTEYN       60
SRFKSRVTMT RDTSTSTVYM ELSSLRSEDT AVYYCARNRW YHGTYYSPGY YVMDAWGQGT      120
LVTVSSASTK GPSVFPLAPS SKSTSGGTAA LGCLVKDYFP EPVTVSWNSG ALTSGVHTFP      180
AVLQSSGLYS LSSVVTVPSS SLGTQTYICN VNHKPSNTKV DKRVEPKSCD KTHTCPPCPA      240
PEAEGAPSVF LFPPKPKDTL MISRTPEVTC VVVDVSHEDP EVKFNWYVDG VEVHNAKTKP      300
REEQYNSTYR VVSVLTVLHQ DWLNGKEYKC KVSNKALPSS IEKTISKAKG QPREPQVYTL      360
PPSREEMTKN QVSLTCLVKG FYPSDIAVEW ESNGQPENNY KTTPPVLDSD GSFFLYSKLT      420
VDKSRWQQGN VFSCSVMHEA LHNHYTQKSL SLSPGK                               456

SEQ ID NO: 37           moltype = AA  length = 213
FEATURE                 Location/Qualifiers
source                  1..213
                        mol_type = protein
                        organism = synthetic construct
SEQUENCE: 37
EIVLTQSPGT LSLSPGERAT LSCKGSQNIE NYLAWYQQKP GQAPRLLIYN RHNLQTGIPD       60
RFSGSGSGTD FTLTISRLEP EDFAVYYCYQ YSDGYTFGGG TKVEIKRTVA APSVFIFPPS      120
DEQLKSGTAS VVCLLNNFYP REAKVQWKVD NALQSGNSQE SVTEQDSKDS TYSLSSTLTL      180
SKADYEKHKV YACEVTHQGL SSPVTKSFNR GEC                                  213

SEQ ID NO: 38           moltype = DNA  length = 1368
FEATURE                 Location/Qualifiers
source                  1..1368
                        mol_type = other DNA
                        organism = synthetic construct
SEQUENCE: 38
caagtgcagc tggtgcagtc cggtgccgaa gtcaagaagc ccgtgcttc ggtgaaagtg        60
tcatgtaccg tgtccggacg ctccttgacg aactaccatc tccaatgggt cagacaggcg     120
cctggacagg gactggaatg gatgggcttc atccggtcct cgggaaatac cgagtacaac     180
agccggttca gtcccgcgt gaccatgact cggacacca gcacctcaac cgtgtacatg       240
gagcttagca gcctgcgctc tgaggacact gccgtgtact actgcgcccg gaacagatgg     300
taccacggga cctactactc gccgggctat acgtgatgg atgcatgggg acagggcact      360
ctggtcactg tgtcctccgc tagcaccaag ggcccatcgg tcttcccct ggcaccctcc      420
tccaagagca cctctggggg cacagcggcc ctgggctgcc tggtcaagga ctacttcccc     480
```

```
gaaccggtga  cggtgtcgtg  gaactcaggc  gcactgacca  gcggcgtgca  caccttcccg   540
gctgtcctac  agtcctcagg  actctactcc  ctcagcagcg  tggtgaccgt  gccctccagc   600
agcttgggca  cccagaccta  catctgcaac  gtgaatcaca  agcccagcaa  caccaaggtg   660
gacaagagag  ttgagcccaa  atcttgtgac  aaaactcaca  catgcccacc  gtgcccagca   720
cctgaagccg  aggggggcacc  gtcagtcttc  ctcttccccc  caaaacccaa  ggacaccctc   780
atgatctccc  ggacccctga  ggtcacatgc  gtggtggtgg  acgtgagcca  cgaagaccct   840
gaggtcaagt  tcaactggta  tgtggacggc  gtggaggtgc  ataatgccaa  gacaaagccg   900
cgggaggagc  agtacaacag  cacgtaccgt  gtggtcagcg  tcctcaccgt  cctgcaccaa   960
gactggctga  atggcaagga  gtacaagtgc  aaggtttcca  acaaagccct  cccatcctcc  1020
atcgagaaaa  ccatctccaa  agccaaaggg  cagccccgag  aaccacaggt  gtacaccctg  1080
cccccatccc  gggaggagat  gaccaagaac  caagtcagcc  tgacctgcct  ggtcaaaggc  1140
ttctatccca  gcgacatcgc  cgtggagtgg  gagagcaatg  ggcagccgga  gaacaactac  1200
aagaccacgc  ctcccgtgct  ggactccgac  ggctccttct  tcctctattc  caagctcacc  1260
gtggacaaga  gcaggtggca  gcaggggaac  gtcttctcat  gctccgtgat  gcatgaggct  1320
ctgcacaacc  actacacgca  gaaaagcctc  tccctgtctc  cgggcaaa                 1368

SEQ ID NO: 39          moltype = DNA  length = 639
FEATURE                Location/Qualifiers
source                 1..639
                       mol_type = other DNA
                       organism = synthetic construct
SEQUENCE: 39
gagatcgtcc  tcacccagtc  tcccggcaca  ttgagtttga  gtccaggtga  aagagcaaca    60
ctgagctgca  aaggtagcca  gaacatcgag  aattatcttg  catggtacca  gcagaaacct   120
gggcaggcac  ccaggctctt  gatctacaat  aggcataacc  tgcagacagg  cattcctgat   180
agattttctg  gatcaggtag  tggtaccgac  tttaccctta  ccatctcacg  actggagcct   240
gaagattttg  ccgtctatta  ctgttatcaa  tacagcgatg  gttacacttt  cgggggaggg   300
acaaaagtgg  aaataaagcg  aactgtggct  gcaccatctg  tcttcatctt  cccgccatct   360
gatgagcagt  tgaaatctgg  aactgcctct  gttgtgtgcc  tgctgaataa  cttctatccc   420
agagagccaa  aagtacagtg  gaaggtggat  aacgcccctcc  aatcgggtaa  ctcccaggag   480
agtgtcacag  agcaggacag  caaggacagc  acctacagcc  tcagcagcac  cctgacgctg   540
agcaaagcag  actacgagaa  acacaaagtc  tacgcctgcg  aagtcaccca  tcagggcctg   600
agctcgcccg  tcacaaagag  cttcaacagg  ggagagtgc                            639

SEQ ID NO: 40          moltype = AA  length = 13
FEATURE                Location/Qualifiers
source                 1..13
                       mol_type = protein
                       organism = synthetic construct
SEQUENCE: 40
TVSGRSRTNY HLQ                                                             13

SEQ ID NO: 41          moltype = AA  length = 126
FEATURE                Location/Qualifiers
source                 1..126
                       mol_type = protein
                       organism = synthetic construct
SEQUENCE: 41
QVQLVQSGAE VKKPGASVKV SCTVSGRSRT NYHLQWVRQA PGQGLEWMGF IRSSGNTEYN          60
SEFKSRVTMT RDTSTSTVYM ELSSLRSEDT AVYYCARNRW YHGTYYSPGY YVMDAWGQGT         120
LVTVSS                                                                    126

SEQ ID NO: 42          moltype = AA  length = 456
FEATURE                Location/Qualifiers
source                 1..456
                       mol_type = protein
                       organism = synthetic construct
SEQUENCE: 42
QVQLVQSGAE VKKPGASVKV SCTVSGRSRT NYHLQWVRQA PGQGLEWMGF IRSSGNTEYN          60
SEFKSRVTMT RDTSTSTVYM ELSSLRSEDT AVYYCARNRW YHGTYYSPGY YVMDAWGQGT         120
LVTVSSASTK GPSVFPLAPS SKSTSGGTAA LGCLVKDYFP EPVTVSWNSG ALTSGVHTFP         180
AVLQSSGLYS LSSVVTVPSS SLGTQTYICN VNHKPSNTKV DKRVEPKSCD KTHTCPPCPA         240
PEAEGAPSVF LFPPKPKDTL MISRTPEVTC VVVDVSHEDP EVKFNWYVDG VEVHNAKTKP         300
REEQYNSTYR VVSVLTVLHQ DWLNGKEYKC KVSNKALPSS IEKTISKAKG QPREPQVYTL         360
PPSREEMTKN QVSLTCLVKG FYPSDIAVEW ESNGQPENNY KTTPPVLDSD GSFFLYSKLT         420
VDKSRWQQGN VFSCSVMHEA LHNHYTQKSL SLSPGK                                   456

SEQ ID NO: 43          moltype = DNA  length = 1368
FEATURE                Location/Qualifiers
source                 1..1368
                       mol_type = other DNA
                       organism = synthetic construct
SEQUENCE: 43
caagtgcagc  tggtgcagtc  cggtgccgaa  gtcaagaagc  ccggtgcttc  ggtgaaagtg    60
tcatgtaccg  tgtccggacg  ctccaggacg  aactaccatc  tccaatgggt  cagacaggcg   120
cctggacagg  gactggaatg  gatgggcttc  atccggtcct  cggggaatac  cgagtacaac   180
agcgaattca  gtcccgcgt  gaccatgact  cgggacacca  gcacctcaac  cgtgtacatg   240
gagcttagca  gcctgcgctc  tgaggacact  gccgtgtact  actgcgcccg  gaacagatgg   300
taccacggga  cctactactc  gccgggctat  tacgtgatgg  atgcatgggg  acagggcact   360
```

```
ctggtcactg tgtcctccgc tagcaccaag ggcccatcgg tcttcccct ggcaccctcc    420
tccaagagca cctctggggg cacagcggcc ctgggctgcc tggtcaagga ctacttcccc    480
gaaccggtga cggtgtcgtg gaactcaggc gcactgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atcttgtgac aaaactcaca catgcccacc gtgcccagca    720
cctgaagccg agggggcacc gtcagtcttc ctcttccccc caaaacccaa ggacaccctc    780
atgatctccc ggaccctga ggtcacatgc gtggtggtgg acgtgagcca cgaagaccct    840
gaggtcaagt tcaactggta tgtggacggc gtggaggtgc ataatgccaa gacaaagccg    900
cgggaggagc agtacaacag cacgtaccgt gtggtcagca cctcaccgt cctgcaccaa    960
gactggctga atggcaagga gtacaagtgc aaggtttcca acaaagccct cccatcctcc    1020
atcgagaaaa ccatctccaa agccaaaggg cagccccgag aaccacaggt gtacaccctg    1080
cccccatccc gggaggagat gaccaagaac caagtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctattc caagctcacc    1260
gtggacaaga gcaggtggca gcaggggaac gtcttctcat gctccgtgat gcatgaggct    1320
ctgcacaacc actacacgca gaaaagcctc tccctgtctc cgggcaaa                1368

SEQ ID NO: 44           moltype = AA  length = 16
FEATURE                 Location/Qualifiers
source                  1..16
                        mol_type = protein
                        organism = synthetic construct
SEQUENCE: 44
FIRSSGNTIY NSEFKS                                                    16

SEQ ID NO: 45           moltype = AA  length = 126
FEATURE                 Location/Qualifiers
source                  1..126
                        mol_type = protein
                        organism = synthetic construct
SEQUENCE: 45
QVQLVQSGAE VKKPGASVKV SCTVSGRSLT NYHLQWVRQA PGQGLEWMGF IRSSGNTIYN    60
SEFKSRVTMT RDTSTSTVYM ELSSLRSEDT AVYYCARNRW YHGTYYSPGY YVMDAWGQGT   120
LVTVSS                                                              126

SEQ ID NO: 46           moltype = AA  length = 456
FEATURE                 Location/Qualifiers
source                  1..456
                        mol_type = protein
                        organism = synthetic construct
SEQUENCE: 46
QVQLVQSGAE VKKPGASVKV SCTVSGRSLT NYHLQWVRQA PGQGLEWMGF IRSSGNTIYN    60
SEFKSRVTMT RDTSTSTVYM ELSSLRSEDT AVYYCARNRW YHGTYYSPGY YVMDAWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKRVEPKSCD KTHTCPPCPA   240
PEAEGAPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPSS IEKTISKAKG QPREPQVYTL   360
PPSREEMTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGK                             456

SEQ ID NO: 47           moltype = DNA  length = 1368
FEATURE                 Location/Qualifiers
source                  1..1368
                        mol_type = other DNA
                        organism = synthetic construct
SEQUENCE: 47
caagtgcagc tggtgcagtc cggtgccgaa gtcaagaagc ccgtgcttc ggtgaaagtg     60
tcatgtaccg tgtccggacg ctccttgacg aactaccatc tccaatgggt cagacaggcg   120
cctggacagg gactggaatg gatgggcttc atccggtcct cgggaatac catctacaac    180
agcgaattca gtcccgcgt gaccatgact cgggacacca gcacctcaac cgtgtacatg   240
gagcttagca gcctgcgctc tgaggacact gccgtgtact actgcgcccg aacagatgg   300
taccacggga cctactactc gccgggctat tacgtgatgg atgcatgggg acagggcact   360
ctggtcactg tgtcctccgc tagcaccaag ggcccatcgg tcttcccct ggcaccctcc   420
tccaagagca cctctggggg cacagcggcc ctgggctgcc tggtcaagga ctacttcccc   480
gaaccggtga cggtgtcgtg gaactcaggc gcactgacca gcggcgtgca caccttcccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagagag ttgagcccaa atcttgtgac aaaactcaca catgcccacc gtgcccagca   720
cctgaagccg agggggcacc gtcagtcttc ctcttccccc caaaacccaa ggacaccctc   780
atgatctccc ggaccctga ggtcacatgc gtggtggtgg acgtgagcca cgaagaccct   840
gaggtcaagt tcaactggta tgtggacggc gtggaggtgc ataatgccaa gacaaagccg   900
cgggaggagc agtacaacag cacgtaccgt gtggtcagca cctcaccgt cctgcaccaa   960
gactggctga atggcaagga gtacaagtgc aaggtttcca acaaagccct cccatcctcc   1020
atcgagaaaa ccatctccaa agccaaaggg cagccccgag aaccacaggt gtacaccctg   1080
cccccatccc gggaggagat gaccaagaac caagtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctattc caagctcacc   1260
gtggacaaga gcaggtggca gcaggggaac gtcttctcat gctccgtgat gcatgaggct   1320
```

-continued

```
ctgcacaacc actacacgca gaaaagcctc tccctgtctc cgggcaaa           1368

SEQ ID NO: 48           moltype = AA  length = 13
FEATURE                 Location/Qualifiers
source                  1..13
                        mol_type = protein
                        organism = synthetic construct
SEQUENCE: 48
TVSGRSLTNY HIQ                                                 13

SEQ ID NO: 49           moltype = AA  length = 126
FEATURE                 Location/Qualifiers
source                  1..126
                        mol_type = protein
                        organism = synthetic construct
SEQUENCE: 49
QVQLVQSGAE VKKPGASVKV SCTVSGRSLT NYHIQWVRQA PGQGLEWMGF IRSSGNTEYN   60
SEFKSRVTMT RDTSTSTVYM ELSSLRSEDT AVYYCARNRW YHGTYYSPGY YVMDAWGQGT  120
LVTVSS                                                            126

SEQ ID NO: 50           moltype = AA  length = 456
FEATURE                 Location/Qualifiers
source                  1..456
                        mol_type = protein
                        organism = synthetic construct
SEQUENCE: 50
QVQLVQSGAE VKKPGASVKV SCTVSGRSLT NYHIQWVRQA PGQGLEWMGF IRSSGNTEYN   60
SEFKSRVTMT RDTSTSTVYM ELSSLRSEDT AVYYCARNRW YHGTYYSPGY YVMDAWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKRVEPKSCD KTHTCPPCPA  240
PEAEGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPSS IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                           456

SEQ ID NO: 51           moltype = DNA  length = 1368
FEATURE                 Location/Qualifiers
source                  1..1368
                        mol_type = other DNA
                        organism = synthetic construct
SEQUENCE: 51
caagtgcagc tggtgcagtc cggtgccgaa gtcaagaagc ccggtgcttc ggtgaaagtg   60
tcatgtaccg tgtccggacg ctcccctcac gaactaccata ttcaatgggt cagacaggcg  120
cctggacagg gactggaatg gatgggcttc atccggtcct cggggaatac cgagtacaac  180
agcgaattca gtcccgcgt gaccatgact cgggacacca gcacctcaac cgtgtacatg  240
gagcttagca gcctgcgctc tgaggacact gccgtgtact actgcgcccg gaacagatgg  300
taccacggga cctactactc gccgggctat tacgtgatgg atgcatgggg acagggcact  360
ctggtcactg tgtcctccgc tagcaccaag ggcccatcgg tcttcccct ggcaccctcc  420
tccaagagca cctctggggg cacagcggcc ctgggctgcc tggtcaagga ctacttcccc  480
gaaccggtga cggtgtcgtg gaactcaggc gcactgacca gcggcgtgca caccttcccg  540
gctgtcctac agtcctcagg actctactcc ctcagcagcg tggtgaccgt gccctccagc  600
agcttgggca cccagaccta catctgcaac gtgaatcaca agcccagcaa caccaaggtg  660
gacaagagag ttgagcccaa atcttgtgac aaaactcaca catgcccacc gtgcccagca  720
cctgaagccg agggggcacc gtcagtcttc ctcttcccc caaaacccaa ggacaccctc  780
atgatctccc ggacccctga ggtcacatgc gtggtggtgg acgtgagcca cgaagaccct  840
gaggtcaagt tcaactggta tgtggacggc gtggaggtgc ataatgccaa gacaaagccg  900
cgggaggagc agtacaacag cacgtaccgt gtggtcagcg tcctcaccgt cctgcaccaa  960
gactggctga atggcaagga gtacaagtgc aaggtttcca acaaagccct cccatcctcc 1020
atcgagaaaa ccatctccaa agccaaaggg cagccccgag aaccacaggt gtacaccctg 1080
cccccatccc gggaggagat gaccaagaac caagtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct tcctctattc caagctcacc 1260
gtggacaaga gcaggtggca gcaggggaac gtcttctcat gctccgtgat gcatgaggct 1320
ctgcacaacc actacacgca gaaaagcctc tccctgtctc cgggcaaa            1368

SEQ ID NO: 52           moltype = AA  length = 13
FEATURE                 Location/Qualifiers
source                  1..13
                        mol_type = protein
                        organism = synthetic construct
SEQUENCE: 52
TVSGRSLTGY HLQ                                                 13

SEQ ID NO: 53           moltype = AA  length = 126
FEATURE                 Location/Qualifiers
source                  1..126
                        mol_type = protein
                        organism = synthetic construct
SEQUENCE: 53
```

```
QVQLVQSGAE VKKPGASVKV SCTVSGRSLT GYHLQWVRQA PGQGLEWMGF IRSSGNTEYN    60
SEFKSRVTMT RDTSTSTVYM ELSSLRSEDT AVYYCARNRW YHGTYYSPGY YVMDAWGQGT   120
LVTVSS                                                              126

SEQ ID NO: 54              moltype = AA   length = 456
FEATURE                    Location/Qualifiers
source                     1..456
                           mol_type = protein
                           organism = synthetic construct
SEQUENCE: 54
QVQLVQSGAE VKKPGASVKV SCTVSGRSLT GYHLQWVRQA PGQGLEWMGF IRSSGNTEYN    60
SEFKSRVTMT RDTSTSTVYM ELSSLRSEDT AVYYCARNRW YHGTYYSPGY YVMDAWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKRVEPKSCD KTHTCPPCPA   240
PEAEGAPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPSS IEKTISKAKG QPREPQVYTL   360
PPSREEMTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGK                             456

SEQ ID NO: 55              moltype = DNA   length = 1368
FEATURE                    Location/Qualifiers
source                     1..1368
                           mol_type = other DNA
                           organism = synthetic construct
SEQUENCE: 55
caagtgcagc tggtgcagtc cggtgccgaa gtcaagaagc ccggtgcttc ggtgaaagtg    60
tcatgtaccg tgtccggacg ctccttgacg ggctaccatc tccaatgggg cagacaggcg   120
cctggacagg gactgaatg gatgggcttc atccggtcct cggggaatac cgagtacaac   180
agcgaattca gtcccgcgt gaccatgact cgggacacca gcacctcaac cgtgtacatg   240
gagcttagca gcctgcgctc tgaggacact ccgtgtactc actgcgcccg gaacagatgg   300
taccacggga cctactactc gccgggctat tacgtgatgg atgcatgggg acagggcact   360
ctggtcactg tgtcctccgc tagcaccaag ggcccatcgg tcttccccct ggcaccctcc   420
tccaagagca cctctggggg cacagcggcc ctgggctgcc tggtcaagga ctacttcccc   480
gaaccggtga cggtgtcgtg gaactcaggc gcactgacca gcggcgtgca caccttcccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagagag ttgagcccaa atcttgtgac aaaactcaca catgcccacc gtgcccagca   720
cctgaagccg agggggcacc gtcagtcttc ctcttccccc caaaacccaa ggacaccctc   780
atgatctccc ggaccccctga ggtcacatgc gtggtggtgg acgtgagcca cgaagaccct   840
gaggtcaagt tcaactggta tgtggacggc gtggaggtgc ataatgccaa gacaaagccg   900
cgggaggagc agtacaacag cacgtaccgt gtggtcagcg tcctcaccgt cctgcaccaa   960
gactggctga atggcaagga gtacaagtgc aaggtttcca acaaagccct cccatcctcc  1020
atcgagaaaa ccatctccaa agccaaaggg cagccccgag aaccacaggt gtacaccctg  1080
cccccatccc gggaggagat gaccaagaac caagtcagcc tgacctgcct ggtcaaaggc  1140
ttctatccca gcgacatcgc cgtggagtgg gagagcaatg ggcagccgga gaacaactac  1200
aagaccacgc ctcccgtgct ggactccgac ggctccttct tcctctattc caagctcacc  1260
gtggacaaga gcaggtggca gcaggggaac gtcttctcat gctccgtgat gcatgaggct  1320
ctgcacaacc actacacgca gaaaagcctc tccctgtctc cgggcaaa               1368

SEQ ID NO: 56              moltype = AA   length = 20
FEATURE                    Location/Qualifiers
source                     1..20
                           mol_type = protein
                           organism = synthetic construct
SEQUENCE: 56
ARNRWHHGTY YSPGYYVMDA                                                20

SEQ ID NO: 57              moltype = AA   length = 126
FEATURE                    Location/Qualifiers
source                     1..126
                           mol_type = protein
                           organism = synthetic construct
SEQUENCE: 57
QVQLVQSGAE VKKPGASVKV SCTVSGRSLT NYHLQWVRQA PGQGLEWMGF IRSSGNTEYN    60
SEFKSRVTMT RDTSTSTVYM ELSSLRSEDT AVYYCARNRW HHGTYYSPGY YVMDAWGQGT   120
LVTVSS                                                              126

SEQ ID NO: 58              moltype = AA   length = 456
FEATURE                    Location/Qualifiers
source                     1..456
                           mol_type = protein
                           organism = synthetic construct
SEQUENCE: 58
QVQLVQSGAE VKKPGASVKV SCTVSGRSLT NYHLQWVRQA PGQGLEWMGF IRSSGNTEYN    60
SEFKSRVTMT RDTSTSTVYM ELSSLRSEDT AVYYCARNRW HHGTYYSPGY YVMDAWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKRVEPKSCD KTHTCPPCPA   240
PEAEGAPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPSS IEKTISKAKG QPREPQVYTL   360
```

```
PPSREEMTKN QVSLTCLVKG FYPSDIAVEW ESNGQPENNY KTTPPVLDSD GSFFLYSKLT    420
VDKSRWQQGN VFSCSVMHEA LHNHYTQKSL SLSPGK                              456

SEQ ID NO: 59           moltype = DNA   length = 1368
FEATURE                 Location/Qualifiers
source                  1..1368
                        mol_type = other DNA
                        organism = synthetic construct
SEQUENCE: 59
caagtgcagc tggtgcagtc cggtgccgaa gtcaagaagc ccggtgcttc ggtgaaagtg    60
tcatgtaccg tgtccggacg ctccttgacg aactaccatc tccaatgggt cagacaggcg    120
cctggacagg gactggaatg gatgggcttc atccggtcct ggggaatac cgagtacaac     180
agcgaattca agtcccgcgt gaccatgact cgggacacca gcacctcaac cgtgtacatg    240
gagcttagca gcctgcgctc tgaggacact gccgtgtact actgcgcccg gaacagatga    300
caccacggga cctactactc gccgggctat tacgtgatgg atgcatgggg acagggcact    360
ctggtcactg tgtcctccgc tagcaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gcactgacca ggggcgtgca caccttcccg    540
gctgtcctac agtcctcagg actctactcc ctcagcagcg tggtgaccgt gcctccagc    600
agcttgggca cccagaccta catctgcaac gtgaatcaca gcccagcaa caccaaggtg    660
gacaagagag ttgagcccaa atcttgtgac aaaactcaca catgcccacc gtgcccagca    720
cctgaaccg aggggcacc gtcagtcttc ctcttcccc caaaacccaa ggacaccctc      780
atgatctccc ggaccctga ggtcacatg gtggtggtgg acgtgagcca cgaagaccct     840
gaggtcaagt tcaactggta tgtggacggc gtggaggtgc ataatgccaa gacaaagccg    900
cgggaggagc agtacaacag cacgtaccgt gtggtcagcg tcctcaccgt cctgcaccaa    960
gactggctga atggcaagga gtacaagtgc aaggtttcca acaaagccct cccatcctcc    1020
atcgagaaaa ccatctccaa agccaaaggg cagccccgag aaccacaggt gtacaccctg    1080
cccccatccc gggaggagat gaccaagaac caagtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctattc caagctcacc    1260
gtggacaaga gcaggtggca gcagggggaac gtcttctcat gctccgtgat gcatgaggct    1320
ctgcacaacc actacacgca gaaaagcctc tccctgtctc cgggcaaa                 1368

SEQ ID NO: 60           moltype = AA   length = 13
FEATURE                 Location/Qualifiers
source                  1..13
                        mol_type = protein
                        organism = synthetic construct
SEQUENCE: 60
TVSGRSLTNY HLV                                                        13

SEQ ID NO: 61           moltype = AA   length = 126
FEATURE                 Location/Qualifiers
source                  1..126
                        mol_type = protein
                        organism = synthetic construct
SEQUENCE: 61
QVQLVQSGAE VKKPGASVKV SCTVSGRSLT NYHLVWVRQA PGQGLEWMGF IRSSGNTEYN    60
SEFKSRVTMT RDTSTSTVYM ELSSLRSEDT AVYYCARNRW YHGTYYSPGY YVMDAWGQGT    120
LVTVSS                                                               126

SEQ ID NO: 62           moltype = AA   length = 456
FEATURE                 Location/Qualifiers
source                  1..456
                        mol_type = protein
                        organism = synthetic construct
SEQUENCE: 62
QVQLVQSGAE VKKPGASVKV SCTVSGRSLT NYHLVWVRQA PGQGLEWMGF IRSSGNTEYN    60
SEFKSRVTMT RDTSTSTVYM ELSSLRSEDT AVYYCARNRW YHGTYYSPGY YVMDAWGQGT    120
LVTVSSASTK GPSVFPLAPS SKSTSGGTAA LGCLVKDYFP EPVTVSWNSG ALTSGVHTFP    180
AVLQSSGLYS LSSVVTVPSS SLGTQTYICN VNHKPSNTKV DKRVEPKSCD KTHTCPPCPA    240
PEAEGAPSVF LFPPKPKDTL MISRTPEVTC VVVDVSHEDP EVKFNWYVDG VEVHNAKTKP    300
REEQYNSTYR VVSVLTVLHQ DWLNGKEYKC KVSNKALPSS IEKTISKAKG QPREPQVYTL    360
PPSREEMTKN QVSLTCLVKG FYPSDIAVEW ESNGQPENNY KTTPPVLDSD GSFFLYSKLT    420
VDKSRWQQGN VFSCSVMHEA LHNHYTQKSL SLSPGK                              456

SEQ ID NO: 63           moltype = DNA   length = 1368
FEATURE                 Location/Qualifiers
source                  1..1368
                        mol_type = other DNA
                        organism = synthetic construct
SEQUENCE: 63
caagtgcagc tggtgcagtc cggtgccgaa gtcaagaagc ccggtgcttc ggtgaaagtg    60
tcatgtaccg tgtccggacg ctccttgacg aactaccatc tcgtctgggt cagacaggcg    120
cctggacagg gactggaatg gatgggcttc atccggtcct ggggaatac cgagtacaac     180
agcgaattca agtcccgcgt gaccatgact cgggacacca gcacctcaac cgtgtacatg    240
gagcttagca gcctgcgctc tgaggacact gccgtgtact actgcgcccg gaacagatgg    300
taccacggga cctactactc gccgggctat tacgtgatgg atgcatgggg acagggcact    360
ctggtcactg tgtcctccgc tagcaccaag ggcccatcgg tcttccccct ggcaccctcc    420
```

```
tccaagagca cctctggggg cacagcggcc ctgggctgcc tggtcaagga ctacttcccc    480
gaaccggtga cggtgtcgtg gaactcaggc gcactgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atcttgtgac aaaactcaca catgcccacc gtgcccagca    720
cctgaagccg aggggggcacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta tgtggacggc gtggaggtgc ataatgccaa gacaaagccg    900
cgggaggagc agtacaacag cacgtaccgt gtggtcagcg tcctcaccgt cctgcaccaa    960
gactggctga atggcaagga gtacaagtgc aaggtttcca acaaagccct cccatcctcc   1020
atcgagaaaa ccatctccaa agccaaaggg cagccccgag aaccacaggt gtacaccctg   1080
cccccatccc gggaggagat gaccaagaac caagtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctattc caagctcacc   1260
gtggacaaga gcaggtggca gcaggggaac gtcttctcat gctccgtgat gcatgaggct   1320
ctgcacaacc actacacgca gaaaagcctc tccctgtctc cgggcaaa               1368

SEQ ID NO: 64          moltype = AA   length = 20
FEATURE                Location/Qualifiers
source                 1..20
                       mol_type = protein
                       organism = synthetic construct
SEQUENCE: 64
ARNRWRHGTY YSPGYYVMDA                                                 20

SEQ ID NO: 65          moltype = AA   length = 126
FEATURE                Location/Qualifiers
source                 1..126
                       mol_type = protein
                       organism = synthetic construct
SEQUENCE: 65
QVQLVQSGAE VKKPGASVKV SCTVSGRSLT NYHLQWVRQA PGQGLEWMGF IRSSGNTEYN     60
SEFKSRVTMT RDTSTSTVYM ELSSLRSEDT AVYYCARNRW RHGTYYSPGY YVMDAWGQGT    120
LVTVSS                                                              126

SEQ ID NO: 66          moltype = AA   length = 456
FEATURE                Location/Qualifiers
source                 1..456
                       mol_type = protein
                       organism = synthetic construct
SEQUENCE: 66
QVQLVQSGAE VKKPGASVKV SCTVSGRSLT NYHLQWVRQA PGQGLEWMGF IRSSGNTEYN     60
SEFKSRVTMT RDTSTSTVYM ELSSLRSEDT AVYYCARNRW RHGTYYSPGY YVMDAWGQGT    120
LVTVSSASTK GPSVFPLAPS SKSTSGGTAA LGCLVKDYFP EPVTVSWNSG ALTSGVHTFP    180
AVLQSSGLYS LSSVVTVPSS SLGTQTYICN VNHKPSNTKV DKRVEPKSCD KTHTCPPCPA    240
PEAEGAPSVF LFPPKPKDTL MISRTPEVTC VVVDVSHEDP EVKFNWYVDG VEVHNAKTKP    300
REEQYNSTYR VVSVLTVLHQ DWLNGKEYKC KVSNKALPSS IEKTISKAKG QPREPQVYTL    360
PPSREEMTKN QVSLTCLVKG FYPSDIAVEW ESNGQPENNY KTTPPVLDSD GSFFLYSKLT    420
VDKSRWQQGN VFSCSVMHEA LHNHYTQKSL SLSPGK                              456

SEQ ID NO: 67          moltype = DNA   length = 1368
FEATURE                Location/Qualifiers
source                 1..1368
                       mol_type = other DNA
                       organism = synthetic construct
SEQUENCE: 67
caagtgcagc tggtgcagtc cggtgccgaa gtcaagaagc ccgtgccttc ggtgaaagtg     60
tcatgtaccg tgtccggacg ctccttgacg aactaccatc tccaatgggt cagacaggcg    120
cctggacagg gactggaatg gatgggcttc atccggtcct cgggaataca cgagtacaac    180
agcgaattca gtcccagcgt gaccatgact cgggacacca gcacctcaac cgtgtacatg    240
gagcttagca gcctgcgctc tgaggacact gccgtgtact actgcgcccg gaacagatgg    300
cggcacggga cctactactc gccgggctat tacgtgatgg atgcatgggg acagggcact    360
ctggtcactg tgtcctccgc tagcaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gcactgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atcttgtgac aaaactcaca catgcccacc gtgcccagca    720
cctgaagccg aggggggcacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta tgtggacggc gtggaggtgc ataatgccaa gacaaagccg    900
cgggaggagc agtacaacag cacgtaccgt gtggtcagcg tcctcaccgt cctgcaccaa    960
gactggctga atggcaagga gtacaagtgc aaggtttcca acaaagccct cccatcctcc   1020
atcgagaaaa ccatctccaa agccaaaggg cagccccgag aaccacaggt gtacaccctg   1080
cccccatccc gggaggagat gaccaagaac caagtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctattc caagctcacc   1260
gtggacaaga gcaggtggca gcaggggaac gtcttctcat gctccgtgat gcatgaggct   1320
ctgcacaacc actacacgca gaaaagcctc tccctgtctc cgggcaaa               1368
```

```
SEQ ID NO: 68           moltype = AA  length = 20
FEATURE                 Location/Qualifiers
source                  1..20
                        mol_type = protein
                        organism = synthetic construct
SEQUENCE: 68
ARNRWYHGTY YSPGYYVMDP                                                    20

SEQ ID NO: 69           moltype = AA  length = 126
FEATURE                 Location/Qualifiers
source                  1..126
                        mol_type = protein
                        organism = synthetic construct
SEQUENCE: 69
QVQLVQSGAE VKKPGASVKV SCTVSGRSLT NYHLQWVRQA PGQGLEWMGF IRSSGNTEYN        60
SEFKSRVTMT RDTSTSTVYM ELSSLRSEDT AVYYCARNRW YHGTYYSPGY YVMDPWGQGT       120
LVTVSS                                                                 126

SEQ ID NO: 70           moltype = AA  length = 456
FEATURE                 Location/Qualifiers
source                  1..456
                        mol_type = protein
                        organism = synthetic construct
SEQUENCE: 70
QVQLVQSGAE VKKPGASVKV SCTVSGRSLT NYHLQWVRQA PGQGLEWMGF IRSSGNTEYN        60
SEFKSRVTMT RDTSTSTVYM ELSSLRSEDT AVYYCARNRW YHGTYYSPGY YVMDPWGQGT       120
LVTVSSASTK GPSVFPLAPS SKSTSGGTAA LGCLVKDYFP EPVTVSWNSG ALTSGVHTFP       180
AVLQSSGLYS LSSVVTVPSS SLGTQTYICN VNHKPSNTKV DKRVEPKSCD KTHTCPPCPA       240
PEAEGAPSVF LFPPKPKDTL MISRTPEVTC VVVDVSHEDP EVKFNWYVDG VEVHNAKTKP       300
REEQYNSTYR VVSVLTVLHQ DWLNGKEYKC KVSNKALPSS IEKTISKAKG QPREPQVYTL       360
PPSREEMTKN QVSLTCLVKG FYPSDIAVEW ESNGQPENNY KTTPPVLDSD GSFFLYSKLT       420
VDKSRWQQGN VFSCSVMHEA LHNHYTQKSL SLSPGK                                456

SEQ ID NO: 71           moltype = DNA  length = 1368
FEATURE                 Location/Qualifiers
source                  1..1368
                        mol_type = other DNA
                        organism = synthetic construct
SEQUENCE: 71
caagtgcagc tggtgcagtc cggtgccgaa gtcaagaagc ccgtgccttc ggtgaaagtg        60
tcatgtaccg tgtccggacg ctccttgacg aactaccatc tccaatgggt cagacaggcg       120
cctggacagg gactggaatg gatgggcttc atccggtcct cgggaatac cgagtacaac       180
agcgaattca gtccccgcgt gaccatgact cgggacacca gcacctcaac cgtgtacatg       240
gagcttagca gcctcgcgctc tgaggacact gccgtgtact actgcgcccg aacagatgg       300
taccacggga cctactactc gccgggctat tacgtgatgg atccatgggg acagggcact       360
ctggtcactg tgtcctccgc tagcaccaag ggcccatccg tcttccccct ggcaccctcc       420
tccaagagca cctctggggg cacagcggcc ctgggctgcc tggtcaagga ctacttcccc       480
gaaccggtga cggtgtcgtg gaactcaggc gcactgacca gcggcgtgca cacctttccg       540
gctgtcctac agtcctcagg actctactcc ctcagcagcg tggtgaccgt gccctccagc       600
agcttgggca cccagaccta catctgcaac gtgaatcaca agcccagcaa caccaaggtg       660
gacaagagag ttgagcccaa atcttgtgac aaaactcaca catgcccacc gtgcccagca       720
cctgaagccg agggggcacc gtcagtcttc ctcttccccc caaaacccaa ggacaccctc       780
atgatctccc ggacccctga ggtcacatgc gtggtggtgg acgtgagcca cgaagaccct       840
gaggtcaagt tcaactggta tgtggacggc gtggaggtgc ataatgccaa gacaaagccg       900
cgggaggagc agtacaacag cacgtaccgt gtggtcagcg tcctcaccgt cctgcaccaa       960
gactggctga atggcaagga gtacaagtgc aaggtttcca acaaagccct cccatcctcc      1020
atcgagaaaa ccatctccaa agccaaaggg cagccccgag aaccacaggt gtacaccctg      1080
cccccatccc gggaggagat gaccaagaac caagtcagcc tgacctgcct ggtcaaaggc      1140
ttctatccca gcgacatcgc cgtggagtgg gagagcaatg ggcagccgga gaacaactac      1200
aagaccacgc ctcccgtgct ggactccgac ggctccttct tcctctattc caagctcacc      1260
gtggacaaga gcaggtggca gcaggggaac gtcttctcat gctccgtgat gcatgaggct      1320
ctgcacaacc actacacgca gaaaagcctc tccctgtctc cgggcaaa                   1368

SEQ ID NO: 72           moltype = AA  length = 20
FEATURE                 Location/Qualifiers
source                  1..20
                        mol_type = protein
                        organism = synthetic construct
SEQUENCE: 72
ARNLWYHGTY YSPGYYVMDA                                                    20

SEQ ID NO: 73           moltype = AA  length = 126
FEATURE                 Location/Qualifiers
source                  1..126
                        mol_type = protein
                        organism = synthetic construct
SEQUENCE: 73
QVQLVQSGAE VKKPGASVKV SCTVSGRSLT NYHLQWVRQA PGQGLEWMGF IRSSGNTEYN        60
```

```
SEFKSRVTMT RDTSTSTVYM ELSSLRSEDT AVYYCARNLW YHGTYYSPGY YVMDAWGQGT  120
LVTVSS                                                          126

SEQ ID NO: 74           moltype = AA  length = 456
FEATURE                 Location/Qualifiers
source                  1..456
                        mol_type = protein
                        organism = synthetic construct
SEQUENCE: 74
QVQLVQSGAE VKKPGASVKV SCTVSGRSLT NYHLQWVRQA PGQGLEWMGF IRSSGNTEYN  60
SEFKSRVTMT RDTSTSTVYM ELSSLRSEDT AVYYCARNLW YHGTYYSPGY YVMDAWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKRVEPKSCD KTHTCPPCPA  240
PEAEGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPSS IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                           456

SEQ ID NO: 75           moltype = DNA  length = 1368
FEATURE                 Location/Qualifiers
source                  1..1368
                        mol_type = other DNA
                        organism = synthetic construct
SEQUENCE: 75
caagtgcagc tggtgcagtc cggtgccgaa gtcaagaagc ccggtgcttc ggtgaaagtg  60
tcatgtaccg tgtccggacg ctccttgacg aactaccatc tccaatgggt cagacaggcg  120
cctggacagg gactgaatg gatgggcttc atccggtcct cggggaatac cgagtacaac  180
agcgaattca gtcccgcgt gaccatgact cgggacacca gcacctcaac cgtgtacatg  240
gagcttagca gcctgcgctc tgaggacact gccgtgtact actgcgcccg gaacctctgg  300
taccacggga cctactactc gccggggctat tacgtgatgg atgcatgggg acagggcact  360
ctggtcactg tgtcctccgc tagcaccaag ggcccatcgg tcttcccct ggcaccctcc  420
tccaagagca cctctggggg cacagcggcc ctgggctgcc tggtcaagga ctacttcccc  480
gaaccggtga cggtgtcgtg gaactcaggc gcactgacca cggcgtgca ccttcccg  540
gctgtcctac agtcctcagg actctactcc ctcagcagc tggtgacgg gcccctcagc  600
agcttgggca cccagaccta catctgcaac gtgaatcaca agcccagcaa caccaaggtg  660
gacaagagag ttgagcccaa atcttgtgac aaaactcaca catgcccacc gtgcccagca  720
cctgaagccg aggggcacc gtcagtcttc ctcttccccc caaaacccaa ggacaccctc  780
atgatctccc ggacccctga ggtcacatgc gtggtggtgg acgtgagcca cgaagaccct  840
gaggtcaagt tcaactggta tgtggacggc gtggaggtgc ataatgccaa gacaaagccg  900
cgggaggagc agtacaacag cacgtaccgt gtggtcagcg tcctcaccgt cctgcaccaa  960
gactggctga atggcaagga gtacaagtgc aaggttccca acaaagccct cccatcctcc  1020
atcgagaaaa ccatctccaa agccaaaggg cagccccgag aaccacaggt gtacaccctg  1080
cccccatccc gggaggagat gaccaagaac caagtcactg tgacctgcct ggtcaaagcc  1140
ttctatccca gcgacatcgc cgtggagtgg gagagcaatg ggcagccgga gaacaactac  1200
aagaccacgc ctcccgtgct ggactccgac ggctccttct tcctctattc caagctcacc  1260
gtggacaaga gcaggtggca gcaggggaac gtcttctcat gctccgtgat gcatgaggct  1320
ctgcacaacc actacacgca gaaaagcctc tccctgtctc cgggcaaa            1368

SEQ ID NO: 76           moltype = AA  length = 13
FEATURE                 Location/Qualifiers
source                  1..13
                        mol_type = protein
                        organism = synthetic construct
SEQUENCE: 76
TRSGRSLTNY HLQ                                                    13

SEQ ID NO: 77           moltype = AA  length = 126
FEATURE                 Location/Qualifiers
source                  1..126
                        mol_type = protein
                        organism = synthetic construct
SEQUENCE: 77
QVQLVQSGAE VKKPGASVKV SCTRSGRSLT NYHLQWVRQA PGQGLEWMGF IRSSGNTEYN  60
SEFKSRVTMT RDTSTSTVYM ELSSLRSEDT AVYYCARNRW YHGTYYSPGY YVMDAWGQGT  120
LVTVSS                                                            126

SEQ ID NO: 78           moltype = AA  length = 456
FEATURE                 Location/Qualifiers
source                  1..456
                        mol_type = protein
                        organism = synthetic construct
SEQUENCE: 78
QVQLVQSGAE VKKPGASVKV SCTRSGRSLT NYHLQWVRQA PGQGLEWMGF IRSSGNTEYN  60
SEFKSRVTMT RDTSTSTVYM ELSSLRSEDT AVYYCARNRW YHGTYYSPGY YVMDAWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKRVEPKSCD KTHTCPPCPA  240
PEAEGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPSS IEKTISKAKG QPREPQVYTL  360
PPSREEMTKN QVSLTCLVKG FYPSDIAVEW ESNGQPENNY KTTPPVLDSD GSFFLYSKLT  420
```

```
VDKSRWQQGN VFSCSVMHEA LHNHYTQKSL SLSPGK                          456

SEQ ID NO: 79           moltype = DNA   length = 1368
FEATURE                 Location/Qualifiers
source                  1..1368
                        mol_type = other DNA
                        organism = synthetic construct
SEQUENCE: 79
caagtgcagc tggtgcagtc tggtgcagaa gtcaagaagc cgggcgcttc agtgaaagtg   60
tcctgcactc ggtcgggacg gtccttgacg aactaccatc ttcaatgggt cagacaggcc  120
cccggtcaag gactgaatg gatggggttc atccggtcct ccgggaacac tgagtacaac   180
tccgagttca agagcagagt gaccatgact cgcgacacct ccacctcgac cgtgtacatg  240
gaactgtcaa gcctgaggag cgaggatacc gccgtgtact actgtgcgcg caatcgctgg  300
taccacggga cctattactc gcctggctac tacgtgatgg acgcctgggg acagggaacc  360
ctcgtgactg tcagctccgc tagcaccaag ggcccatcgg tcttccccct ggcaccctcc  420
tccaagagca cctctggggg cacagcggcc ctgggctgcc tggtcaagga ctacttcccc  480
gaaccggtga cggtgtcgtg gaactcaggc gcactgacca gcggcgtgca cacctttccg  540
gctgtcctac agtcctcagg actctactcc ctcagcagcg tggtgaccgt gccctccagc  600
agcttgggca cccagaccta catctgcaac gtgaatcaca agcccagcaa caccaaggtg  660
gacaagagag ttgagcccaa atcttgtgac aaaactcaca catgcccacc gtgcccagca  720
cctgaagccg agggggcacc gtcagtcttc ctcttccccc caaaacccaa ggacaccctc  780
atgatctccc ggaccccctga ggtcacatgc gtggtggtgg acgtgagcca cgaagaccct  840
gaggtcaagt tcaactggta tgtggacggc gtggaggtgc ataatgccaa gacaaagccg  900
cgggaggagc agtacaacag cacgtaccgt gtggtcagcg tcctcaccgt cctgcaccaa  960
gactggctga atggcaagga gtacaagtgc aaggtttcca acaaagccct cccatcctcc 1020
atcgagaaaa ccatctccaa agccaaaggg cagccccgag aaccacaggt gtacaccctg 1080
cccccatccc gggaggagat gaccaagaac caagtcagcc tgacctgcct ggtcaaaggc 1140
ttctatccca gcgacatcgc cgtggagtgg gagagcaatg ggcagccgga gaacaactac 1200
aagaccacgc ctcccgtgct ggactccgac ggctccttct cctctattc caagctcacc 1260
gtggacaaga gcaggtggca gcaggggaac gtcttctcat gctccgtgat gcatgaggct 1320
ctgcacaacc actacacgca gaaaagcctc tccctgtctc cgggcaaa            1368

SEQ ID NO: 80           moltype = AA   length = 13
FEATURE                 Location/Qualifiers
source                  1..13
                        mol_type = protein
                        organism = synthetic construct
SEQUENCE: 80
TVSGRSLTNI HLQ                                                    13

SEQ ID NO: 81           moltype = AA   length = 126
FEATURE                 Location/Qualifiers
source                  1..126
                        mol_type = protein
                        organism = synthetic construct
SEQUENCE: 81
QVQLVQSGAE VKKPGASVKV SCTVSGRSLT NIHLQWVRQA PGQGLEWMGF IRSSGNTEYN   60
SEFKSRVTMT RDTSTSTVYM ELSSLRSEDT AVYYCARNRW YHGTYYSPGY YVMDAWGQGT  120
LVTVSS                                                             126

SEQ ID NO: 82           moltype = AA   length = 456
FEATURE                 Location/Qualifiers
source                  1..456
                        mol_type = protein
                        organism = synthetic construct
SEQUENCE: 82
QVQLVQSGAE VKKPGASVKV SCTVSGRSLT NIHLQWVRQA PGQGLEWMGF IRSSGNTEYN   60
SEFKSRVTMT RDTSTSTVYM ELSSLRSEDT AVYYCARNRW YHGTYYSPGY YVMDAWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKRVEPKSCD KTHTCPPCPA  240
PEAEGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPSS IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                            456

SEQ ID NO: 83           moltype = DNA   length = 1368
FEATURE                 Location/Qualifiers
source                  1..1368
                        mol_type = other DNA
                        organism = synthetic construct
SEQUENCE: 83
caagtgcagc tggtgcagtc gggagcagaa gtcaagaagc ctggagcctc agtgaaagtg   60
tcctgcaccg tcagcggtcg gagcctgacc aacatccacc ttcagtgggt cagacaggct  120
cccggacaag gcctgaatg gatgggcttc attcgctcgt ccggaaacac ggagtacaac  180
tctgagttca gtcccgcgt gaccatgact agggacacca gcacctcgac cgtgtacatg  240
gaactgtcca gcctgagatc cgaggacact gccgtgtatt actgtgcgcg gaatcggtgg  300
taccatggga cttactactc cccgggctac tacgtgatgg atgcctgggg tcaagggacc  360
ctcgtgactg tgtcatccgc tagcaccaag ggcccatcgg tcttccccct ggcaccctcc  420
tccaagagca cctctggggg cacagcggcc ctgggctgcc tggtcaagga ctacttcccc  480
```

```
gaaccggtga cggtgtcgtg gaactcaggc gcactgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atcttgtgac aaaactcaca catgcccacc gtgcccagca    720
cctgaagccg aggggggcacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta tgtggacggc gtggaggtgc ataatgccaa gacaaagccg    900
cgggaggagc agtacaacag cacgtaccgt gtggtcagcg tcctcaccgt cctgcaccaa    960
gactggctga atggcaagga gtacaagtgc aaggtttcca acaaagccct cccatcctcc   1020
atcgagaaaa ccatctccaa agccaaaggg cagccccgag aaccacaggt gtacaccctg   1080
cccccatccc gggaggagat gaccaagaac caagtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctattc caagctcacc   1260
gtggacaaga gcaggtggca gcaggggaac gtcttctcat gctccgtgat gcatgaggct   1320
ctgcacaacc actacacgca gaaaagcctc tccctgtctc cgggcaaa                1368

SEQ ID NO: 84         moltype = AA  length = 13
FEATURE               Location/Qualifiers
source                1..13
                      mol_type = protein
                      organism = synthetic construct
SEQUENCE: 84
TVSGRSLTNY HLG                                                          13

SEQ ID NO: 85         moltype = AA  length = 126
FEATURE               Location/Qualifiers
source                1..126
                      mol_type = protein
                      organism = synthetic construct
SEQUENCE: 85
QVQLVQSGAE VKKPGASVKV SCTVSGRSLT NYHLGWVRQA PGQGLEWMGF IRSSGNTEYN     60
SEFKSRVTMT RDTSTSTVYM ELSSLRSEDT AVYYCARNRW YHGTYYSPGY YVMDAWGQGT    120
LVTVSS                                                                126

SEQ ID NO: 86         moltype = AA  length = 456
FEATURE               Location/Qualifiers
source                1..456
                      mol_type = protein
                      organism = synthetic construct
SEQUENCE: 86
QVQLVQSGAE VKKPGASVKV SCTVSGRSLT NYHLGWVRQA PGQGLEWMGF IRSSGNTEYN     60
SEFKSRVTMT RDTSTSTVYM ELSSLRSEDT AVYYCARNRW YHGTYYSPGY YVMDAWGQGT    120
LVTVSSASTK GPSVFPLAPS SKSTSGGTAA LGCLVKDYFP EPVTVSWNSG ALTSGVHTFP    180
AVLQSSGLYS LSSVVTVPSS SLGTQTYICN VNHKPSNTKV DKRVEPKSCD KTHTCPPCPA    240
PEAEGAPSVF LFPPKPKDTL MISRTPEVTC VVVDVSHEDP EVKFNWYVDG VEVHNAKTKP    300
REEQYNSTYR VVSVLTVLHQ DWLNGKEYKC KVSNKALPSS IEKTISKAKG QPREPQVYTL    360
PPSREEMTKN QVSLTCLVKG FYPSDIAVEW ESNGQPENNY KTTPPVLDSD GSFFLYSKLT    420
VDKSRWQQGN VFSCSVMHEA LHNHYTQKSL SLSPGK                               456

SEQ ID NO: 87         moltype = DNA  length = 1368
FEATURE               Location/Qualifiers
source                1..1368
                      mol_type = other DNA
                      organism = synthetic construct
SEQUENCE: 87
caagtgcagt tggtgcagtc cggtgccgaa gtcaagaagc cgggagcttc cgtgaaagtg     60
tcgtgcactg tgtccggtcg gagcctgacc aactaccacc tgggctgggt cagacaggca    120
cctggccaag gactggaatg gatgggcttc atccggagct caggaaacac cgagtacaac    180
tcggagttca gtcgcgcgt gactatgacg cgggacactt caaccagcac tgtctacatg    240
gaacttagct ctctgaggtc cgaggacacc gccgtgtact actgtgcccg caatagatgg    300
taccatggga cctactactc ccccggctat tacgtgatgg atgcgtgggg acaggggacc    360
ctcgtgaccg tgtcctccgc tagcaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gcactgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atcttgtgac aaaactcaca catgcccacc gtgcccagca    720
cctgaagccg aggggggcacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta tgtggacggc gtggaggtgc ataatgccaa gacaaagccg    900
cgggaggagc agtacaacag cacgtaccgt gtggtcagcg tcctcaccgt cctgcaccaa    960
gactggctga atggcaagga gtacaagtgc aaggtttcca acaaagccct cccatcctcc   1020
atcgagaaaa ccatctccaa agccaaaggg cagccccgag aaccacaggt gtacaccctg   1080
cccccatccc gggaggagat gaccaagaac caagtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctattc caagctcacc   1260
gtggacaaga gcaggtggca gcaggggaac gtcttctcat gctccgtgat gcatgaggct   1320
ctgcacaacc actacacgca gaaaagcctc tccctgtctc cgggcaaa                1368
```

```
SEQ ID NO: 88            moltype = AA  length = 16
FEATURE                  Location/Qualifiers
source                   1..16
                         mol_type = protein
                         organism = synthetic construct
SEQUENCE: 88
FIRRSGNTEY NSEFKS                                                        16

SEQ ID NO: 89            moltype = AA  length = 126
FEATURE                  Location/Qualifiers
source                   1..126
                         mol_type = protein
                         organism = synthetic construct
SEQUENCE: 89
QVQLVQSGAE VKKPGASVKV SCTVSGRSLT NYHLQWVRQA PGQGLEWMGF IRRSGNTEYN         60
SEFKSRVTMT RDTSTSTVYM ELSSLRSEDT AVYYCARNRW YHGTYYSPGY YVMDAWGQGT        120
LVTVSS                                                                  126

SEQ ID NO: 90            moltype = AA  length = 456
FEATURE                  Location/Qualifiers
source                   1..456
                         mol_type = protein
                         organism = synthetic construct
SEQUENCE: 90
QVQLVQSGAE VKKPGASVKV SCTVSGRSLT NYHLQWVRQA PGQGLEWMGF IRRSGNTEYN         60
SEFKSRVTMT RDTSTSTVYM ELSSLRSEDT AVYYCARNRW YHGTYYSPGY YVMDAWGQGT        120
LVTVSSASTK GPSVFPLAPS SKSTSGGTAA LGCLVKDYFP EPVTVSWNSG ALTSGVHTFP        180
AVLQSSGLYS LSSVVTVPSS SLGTQTYICN VNHKPSNTKV DKRVEPKSCD KTHTCPPCPA        240
PEAEGAPSVF LFPPKPKDTL MISRTPEVTC VVVDVSHEDP EVKFNWYVDG VEVHNAKTKP        300
REEQYNSTYR VVSVLTVLHQ DWLNGKEYKC KVSNKALPSS IEKTISKAKG QPREPQVYTL        360
PPSREEMTKN QVSLTCLVKG FYPSDIAVEW ESNGQPENNY KTTPPVLDSD GSFFLYSKLT        420
VDKSRWQQGN VFSCSVMHEA LHNHYTQKSL SLSPGK                                 456

SEQ ID NO: 91            moltype = DNA  length = 1368
FEATURE                  Location/Qualifiers
source                   1..1368
                         mol_type = other DNA
                         organism = synthetic construct
SEQUENCE: 91
caagtgcagc tggtgcagtc aggagccgaa gtcaagaagc ctggagcctc ggtgaaagtg         60
tcctgcaccg tgtcggggag gagcctgacc aactaccatc ttcaatgggt ccgccaagca        120
ccgggacagg gtttggagtg gatgggcttc atcagacgac gcggcaacac cgagtataac        180
tctgaattca gtccagagt gaccatgacc cgggacactt ccacgtcaac tgtctacatg        240
gagctgtcgt ccctgcgtc cgaagatact gctgtgtact actgtgcccg gaatcgctgg        300
taccacggca cttactactc ccccgggtac tacgtgatgg acgcgtgggg acagggtacc        360
ctcgtgactg tgtccagcgc tagcaccaag ggcccatcgg tcttcccct ggcaccctcc        420
tccaagagca cctctggggg cacagcggcc ctgggctgcc tggtcaagga ctacttcccc        480
gaaccggtga cggtgtcgtg gaactcaggc gcactgacca gcggcgtgca caccttcccg        540
gctgtcctac agtcctcagg actctactcc ctcagcagcg tggtgaccgt gcctccagc        600
agcttgggca cccagaccta catctgcaac gtgaatcaca agcccagcaa caccaaggtg        660
gacaagagag ttgagcccaa atcttgtgac aaaactcaca catgcccacc gtgcccagca        720
cctgaagccg aggggcacc gtcagtcttc ctcttccccc caaaacccaa ggacaccctc        780
atgatctccc ggacccctga ggtcacatgc gtggtggtgg acgtgagcca cgaagaccct        840
gaggtcaagt tcaactggta tgtggacggc gtggaggtgc ataatgccaa gacaaagccg        900
cgggaggagc agtacaacag cacgtaccgt gtggtcagcg tcctcaccgt cctgcaccaa        960
gactggctga atggcaagga gtacaagtgc aaggtttcca acaaagccct cccatcctcc       1020
atcgagaaaa ccatctccaa agccaaaggg cagccccgag aaccacaggt gtacaccctg       1080
cccccatccc gggaggagat gaccaagaac caagtcagcc tgacctgcct ggtcaaaggc       1140
ttctatccca gcgacatcgc cgtggagtgg gagagcaatg ggcagccgga gaacaactac       1200
aagaccacgc ctcccgtgct ggactccgac ggctccttct tcctctattc caagctcacc       1260
gtggacaaga gcaggtggca gcaggggaac gtcttctcat gctccgtgat gcatgaggct       1320
ctgcacaacc actacacgca gaaaagcctc tccctgtctc cgggcaaa                    1368

SEQ ID NO: 92            moltype = AA  length = 456
FEATURE                  Location/Qualifiers
source                   1..456
                         mol_type = protein
                         organism = synthetic construct
SEQUENCE: 92
QVQLKESGPG LVKPSQTLSL TCTVSGFSLT NYHLQWVRQP PGKGLEWIGF IRSSGNTEYN         60
PSLKSRVTIS RDTSKNQVSL KLSSVTAADT AVYYCARKRW VHGTWYSPGY YVMDAWGQGT        120
LVTVSSASTK GPSVFPLAPS SKSTSGGTAA LGCLVKDYFP EPVTVSWNSG ALTSGVHTFP        180
AVLQSSGLYS LSSVVTVPSS SLGTQTYICN VNHKPSNTKV DKKVEPKSCD KTHTCPPCPA        240
PEAAGGPSVF LFPPKPKDTL MISRTPEVTC VVVDVSHRDP EVKFNWYVDG VEVHNAKTKP        300
REEQYNSTYR VVSVLTVLHQ DWLNGKEYKC AVSNKALPAP IEKTISKAKG QPREPQVYTL        360
PPSRDELTKN QVSLTCLVKG FYPSDIAVEW ESNGQPENNY KTTPPVLDSD GSFFLYSKLT        420
VDKSRWQQGN VFSCSVMHEA LHNHYTQKSL SLSPGK                                 456

SEQ ID NO: 93            moltype = AA  length = 214
```

```
FEATURE                  Location/Qualifiers
source                   1..214
                         mol_type = protein
                         organism = synthetic construct
SEQUENCE: 93
DIQLTQSPSA MSASVGDRVT ITCRASQGIS NYLAWYQQKP GKAPKLLIYA ASTLQSGVAS    60
RFSGRGSGTD FTLTISSLQP EDFATYYCQQ SDILPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 94            moltype = AA  length = 456
FEATURE                  Location/Qualifiers
source                   1..456
                         mol_type = protein
                         organism = synthetic construct
SEQUENCE: 94
QVQLKESGPG LVKPSQTLSL TCTVSGFSLT NYHLQWVRQP PGKGLEWIGF IRSSGNTEYN    60
PSLKSRVTIS RDTSKNQVSL KLSSVTAADT AVYYCARKRW VHGTWYSPGY YVMDAWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKRVEPKSCD KTHTCPPCPA   240
PEAEGAPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPSS IEKTISKAKG QPREPQVYTL   360
PPSREEMTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGK                            456

SEQ ID NO: 95            moltype = AA  length = 500
FEATURE                  Location/Qualifiers
source                   1..500
                         mol_type = protein
                         organism = Homo sapiens
SEQUENCE: 95
MPPAVGGPVG YTPPDGGWGW AVVIGAFISI GFSYAFPKSI TVFFKEIEGI FHATTSEVSW    60
ISSIMLAVMY GGGPISSILV NKYGSRIVMI VGGCLSGCGL IAASFCNTVQ QLYVCIGVIG   120
GLGLAFNLNP ALTMIGKYFY KRRPLANGLA MAGSPVFLCT LAPLNQVFFG IFGWRGSFLI   180
LGGLLLNCCV AGALMRPIGP KPTKAGKDKS KASLEKAGKS GVKKDLHDAN TDLIGRHPKQ   240
EKRSVFQTIN QFLDLTLFTH RGFLLYLSGN VIMFFGLFAP LVFLSSYGKS QHYSSEKSAF   300
LLSILAFVDM VARPSMGLVA NTKPIRPRIQ YFFAASVVAN GVCHMLAPLS TTYVGFCVYA   360
GFFGFAFGWL SSVLFETLMD LVGPQRFSSA VGLVTIVECC PVLLGPPLLG RLNDMYGDYK   420
YTYWACGVVL IISGIYLFIG MGINYRLLAK EQKANEQKKE SKEEETSIDV AGKPNEVTKA   480
AESPDQKDTD GGPKEEESPV                                              500

SEQ ID NO: 96            moltype = AA  length = 500
FEATURE                  Location/Qualifiers
source                   1..500
                         mol_type = protein
                         organism = Macaca fascicularis
SEQUENCE: 96
MPPAVGGPVG YTPPDGGWGW AVVIGAFISI GFSYAFPKSI TVFFKEIESI FHATTSEVSW    60
ISSIMLAVMY GGGPISSILV NKYGSRIVMI IGGCLSGCGL IAASFCNTVQ ELYFCIGFVG   120
GLGLAFNLNP ALTMIGKYFY KRRPLANGLA MAGSPVFLCT LAPLNQVFFD IFGWRGSFLI   180
LGGLLLNCCV AGALMRPIGP KPTKAGKDKS KASLQKAGKS GVKKGRHDAN TDLIGRHPKR   240
EKRSVFQTIN QFLDLTLFTH RGFLLYLSGN VIMFFGLFAP LVFLSSYGKS QHYSSEKSAF   300
LLSILAFVDM VARPSMGLVA NTKPIRPRIQ YFFAASIVAN GVCHMLAPLS TTYVGFCVYA   360
GFFGFAFGWL SSVLFETLMD LVGPQRFSSA VGLVTIVECC PVLLGPPLLG RLSDMYGDYK   420
YTYWACGVVL IISGIYLFIG MGINYRLLAK EQKANEQKKE SKEEETSIDV AGKPKEVTKA   480
AESPDQKDTE EGPKEEDSPV                                              500

SEQ ID NO: 97            moltype = AA  length = 13
FEATURE                  Location/Qualifiers
VARIANT                  2
                         note = X at position 2 is Valine or Arginine
VARIANT                  7
                         note = X at position 7 is Leucine or Arginine
VARIANT                  9
                         note = X at position 9 is Asparagine or Glycine
VARIANT                  10
                         note = X at position 10 is Tyrosine or Isoleucine
VARIANT                  12
                         note = X at position 12 is Leucine or Isoleucine
VARIANT                  13
                         note = X at position 13 is Glutamine, Valine, or Glycine
source                   1..13
                         mol_type = protein
                         organism = synthetic construct
SEQUENCE: 97
TXSGRSXTXX HXX                                                      13

SEQ ID NO: 98            moltype = AA  length = 16
FEATURE                  Location/Qualifiers
```

```
                                -continued
VARIANT             4
                    note = X at position 4 is Arginine or Serine
VARIANT             9
                    note = X at position 9 is Isoleucine or Glutamic Acid
VARIANT             13
                    note = X at position 13 is Glutamic Acid or Arginine
source              1..16
                    mol_type = protein
                    organism = synthetic construct
SEQUENCE: 98
FIRXSGNTXY NSXFKS                                                          16

SEQ ID NO: 99       moltype = AA   length = 20
FEATURE             Location/Qualifiers
VARIANT             4
                    note = X at position 4 is Arginine or Leucine
VARIANT             6
                    note = X at position 6 is Histidine or Arginine or Tyrosine
VARIANT             20
                    note = X at position 20 is Proline or Alanine
source              1..20
                    mol_type = protein
                    organism = synthetic construct
SEQUENCE: 99
ARNXWXHGTY YSPGYYVMDX                                                      20
```

HUMAN MONOCARBOXYLATE TRANSPORTER 1 ANTIBODIES AND USES THEREOF

SEQUENCE LISTING FILE

The present application is being filed along with a Sequence Listing in ST.26 XML format. The Sequence Listing is provided as a file titled "X22880 sequence listing v1_2" created Nov. 2, 2022 and is 128 kilobytes in size. The Sequence Listing information in the ST.26 XML format is incorporated herein by reference in its entirety.

The present disclosure is in the field of medicine. Particularly, the present disclosure relates to antibodies that specifically bind human monocarboxylate transporter 1 (MCT1) ("anti-human MCT1 antibodies"), compositions comprising such anti-human MCT1 antibodies, and methods of using such anti-human MCT1 antibodies.

The monocarboxylate transporter 1 (also known as MCT1, SLC16A1, HHF7, MCT, MCT1D, or "solute carrier family 16 member 1") is a multi-pass transmembrane protein responsible for the facilitated transport of critical metabolites, including products of glycolysis. MCT1 is a member of one of the largest family of surface membrane proteins, known as solute channel proteins (SLCs), whose functions involve the transport across membranes of critical cellular nutrients, metabolites, ions, hormones, and lipids. MCT1 belongs to the SLC16 family of transporters, five of which have been shown to transport monocarboxylates, such as pyruvate, lactate, and ketones (such as acetoacetate and β-hydroxybutyrate), in a facilitated, pH dependent and bidirectional manner. SLC16 family of transporters SLC16A1 (MCT1), SLC16A7 (MCT2), SLC16A8 (MCT3) and SLC16A3 (MCT4) have all been shown to transport monocarboxylates with Km in the 1 to 40 mM range (Halestrap A P, *IUBMB Life*. 2012; 64(1):1-9). MCT1, MCT3 and MCT4 are co-expressed with the Ig-domain containing surface protein CD147 (Basigin), which in many cells is critical for proper cell surface expression. MCT1 is especially relevant to the transport of lactate in T and B cells (Fischer K, et al., *Blood*. 2007; 109(9):3812-9).

Immune cells undergo shifts in their metabolic demand throughout growth, and require specific metabolic states for employing their effector functions. For example, both glycolysis and mitochondrial oxidative metabolism are elevated in CD4$^+$ T cells from lupus-prone B6.Sle1.Sle2.Sle3 (TC) mice as compared to non-autoimmune controls (Yin Y, et al., *Sci Transl Med*. 2015; 7(274):274ra18). Treatment of the TC mice with a combination of the mitochondrial metabolism inhibitor metformin and the glucose metabolism inhibitor 2-Deoxy-D-glucose (2DG) normalized T cell metabolism and reversed disease biomarkers (Yin Y, et al., *Sci Transl Med*. 2015; 7(274):274ra18). Both metformin and 2DG also reduced IFNγ production in vitro (Yin Y, et al., *Sci Transl Med*. 2015; 7(274):274ra18). Blocking the export of lactate reduces flux through the glycolytic pathway and, by altering Myc, can shift T cells away from effector functions (Doherty J R, et al., *Cancer Research*. 2014; 74(3):908-20; Wang R, et al., *Immunity*. 2011; 35(6):871-82).

Individuals with homozygous MCT1 loss-of-function (LOF) mutations were identified under stress (infection, starvation) due to alterations in ketone utilization and metabolism; adult humans deficient in MCT1 are otherwise healthy (van Hasselt P M, *N Engl J Med*. 2014, 371(20): 1900-7; Balasubramaniam S, et al., *JIMD Rep*. 2016; 29:33-8). Infants presented with ketone utilization defects and, sometimes, exercise intolerance. These various symptoms disappeared as they aged, possibly due to growth of skeletal muscle mass during adolescence. Heterozygous family members of individuals with homozygous MCT1 mutations had no history of ketoacidosis, suggesting that LOF mutations cause ketoacidosis only in conjunction with additional genetic/environmental factors (Balasubramaniam S, et al., *JIMD Rep*. 2016, 29:33-8). Outside the immune system, MCT1 is expressed in multiple organs, including skeletal muscle, kidney, liver, testis, heart, and brain, along with other MCTs. The absence of broad toxicity in individuals with MCT1 mutations is likely due to the redundancy of MCTs. For example, MCT1, MCT2 & MCT4 are all expressed in the retina (Philp N J, *Investigative Ophthalmology & Visual Science*. 2003, 44(3):1305-11), and no retinal defects were observed in MCT1-deficient individuals suggesting functional redundancy. At this time, no overt immune deficiencies have been observed in MCT1-deficient individuals. Additionally, MCT1-deficient humans do not present with any red blood cell dysfunction.

Given the broad expression of MCTs across many tissues, small molecule MCT inhibitors have been developed. However, many of these small molecule approaches hit multiple MCTs, posing off target toxicities, including tissue toxicities. As such, there remains a need for therapies that selectively and specifically target MCT1.

Antibodies targeting MCT1 have been disclosed for example, as set forth in WO19136300. However, to date, no known antibody that specifically binds human MCT1 has been approved for therapeutic use or is in clinical development. Therefore, there remains a need for antibodies that selectively and specifically bind human MCT1, have desirable developability and patient safety profiles, and can be used for treatment of MCT1 associated disorders, such as autoimmune conditions.

DETAILED DESCRIPTION

The present disclosure provides antibodies that selectively and specifically bind human MCT1 and inhibit MCT1-mediated responses (e.g., metabolite transport, T cell and B cell proliferation), and/or drive differentiation of regulatory T cells; and compositions comprising such MCT1 antibodies, and methods of using such MCT1 antibodies and compositions. Particularly, the present disclosure provides anti-human MCT1 antibodies that specifically bind human MCT1, have desirable binding affinities, inhibit MCT1 mediated responses, have desirable developability and/or patient safety profiles, such as having low immunogenicity risk. Desirable developability profiles further reduce potentially complex and costly changes in downstream analytical and manufacturing processes. The anti-human MCT1 antibodies as disclosed herein, can be used to treat MCT1 associated disorders such as, autoimmune conditions (e.g., systemic lupus erythematosus, inflammatory bowel disease, rheumatoid arthritis, psoriasis, or multiple sclerosis), allergic conditions, inflammatory conditions, metabolic disorders, transplant or cell therapy recipients, MCT1-positive cancers, exercise-induced hyperinsulinism (EIHI) conditions, and/or polycystic kidney disease (ADPKD). As such, the anti-human MCT1 antibodies provided herein have one or more of the following properties: 1) specifically bind human MCT1 with desirable binding affinities, 2) inhibit MCT1 mediated metabolite transport, 3) inhibit CD4 and CD8 T cell proliferation, 4) inhibit B cell proliferation, 5) drive differentiation of regulatory T cells (e.g., Foxp3+ regulatory T cells), 6) do not significantly induce effector function mediated killing (e.g., ADCC, ADCP) or neutrophil activation in vitro, 7) do not significantly induce complement mediated activity, 8) low immunogenicity risk, 9) low in culture oxidation and/or degradation, 10) low to no detectable human serum protein binding, 11) low hydrophobicity, 12) desirable properties such as stability, solubility, and low nonspecific interactions e.g., binding to analytical column resin, providing desirable developability and patient safety profiles for use in the treatment of MCT1-associated disorders.

In some embodiments, the anti-human MCT1 antibodies as disclosed herein are fully humanized antibodies. In some embodiments, the anti-human MCT1 antibodies as disclosed herein specifically bind human and/or cynomolgus MCT1. In some embodiments, the anti-human MCT1 antibodies as disclosed herein, comprise particular combinations of framework amino acid sequences which support, and allow for optimal presentation of the particular CDR amino acid sequences as disclosed herein. In some embodiments, such anti-human MCT1 antibodies have desirable binding affinities and functional activity, such as those described herein. In further embodiments, the anti-human MCT1 antibodies as disclosed herein, specifically bind human MCT1 and inhibit metabolite transport (e.g., lactate, pyruvate, ketones), and T cell and/or B cell proliferation. In further embodiments, the anti-human MCT1 antibodies as disclosed herein, specifically bind human MCT1 and drive differentiation of regulatory T cells. In such embodiments, increase in regulatory T cells by the anti-human MCT1 antibodies of the disclosure results in inhibition of autoimmune responses. In further embodiments, anti-human MCT1 antibodies as disclosed herein, have desirable developability and/or patient safety profiles such as acceptable immunogenicity risk, reduced or eliminated: oxidation and in culture degradation; nonspecific serum protein binding (e.g., serum IgG, apolipoprotein), and/or hydrophobicity. These desirable developability profiles indicate reduced risk of aggregation and/or loss of yield, reduced risk of faster clearance, desirable pharmacokinetic profile, solubility, stability, and/or reduced challenges in downstream purification and analytical processes.

In yet other embodiments, the anti-human MCT1 antibodies of the present disclosure do not significantly induce effector function mediated killing and/or C1q complement activity.

Accordingly, in some embodiments, the present disclosure provides an antibody or antigen binding fragment thereof, that specifically binds human MCT1, wherein the antibody comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein:

a. the HCDR1 comprises SEQ ID NO: 30;
   the HCDR2 comprises SEQ ID NO: 31;
   the HCDR3 comprises SEQ ID NO: 32;
   the LCDR1 comprises SEQ ID NO: 33;
   the LCDR2 comprises SEQ ID NO: 5; and
   the LCDR3 comprises SEQ ID NO: 6;
b. the HCDR1 comprises SEQ ID NO: 30;
   the HCDR2 comprises SEQ ID NO: 2;
   the HCDR3 comprises SEQ ID NO: 56, SEQ ID NO: 64, SEQ ID NO: 68, or SEQ ID NO: 72;
   the LCDR1 comprises SEQ ID NO: 33;
   the LCDR2 comprises SEQ ID NO: 5; and
   the LCDR3 comprises SEQ ID NO: 6;
c. the HCDR1 comprises SEQ ID NO: 30;
   the HCDR2 comprises SEQ ID NO: 2;
   the HCDR3 comprises SEQ ID NO: 99;
   the LCDR1 comprises SEQ ID NO: 33;
   the LCDR2 comprises SEQ ID NO: 5; and
   the LCDR3 comprises SEQ ID NO: 6;
d. the HCDR1 comprises SEQ ID NO: 30;
   the HCDR2 comprises SEQ ID NO: 2;
   the HCDR3 comprises SEQ ID NO: 72;
   the LCDR1 comprises SEQ ID NO: 4;
   the LCDR2 comprises SEQ ID NO: 5; and
   the LCDR3 comprises SEQ ID NO: 6;
e. the HCDR1 comprises SEQ ID NO: 30;
   the HCDR2 comprises SEQ ID NO: 2;
   the HCDR3 comprises SEQ ID NO: 68;
   the LCDR1 comprises SEQ ID NO: 4;
   the LCDR2 comprises SEQ ID NO: 5; and
   the LCDR3 comprises SEQ ID NO: 6;
f. the HCDR1 comprises SEQ ID NO: 40, SEQ ID NO: 48, SEQ ID NO: 52, SEQ ID NO: 60, SEQ ID NO: 76, SEQ ID NO: 80 or SEQ ID NO: 84;
   the HCDR2 comprises SEQ ID NO: 2;
   the HCDR3 comprises SEQ ID NO: 32;
   the LCDR1 comprises SEQ ID NO: 33;
   the LCDR2 comprises SEQ ID NO: 5; and
   the LCDR3 comprises SEQ ID NO: 6;
g. the HCDR1 comprises SEQ ID NO: 97;
   the HCDR2 comprises SEQ ID NO: 2;
   the HCDR3 comprises SEQ ID NO: 32;
   the LCDR1 comprises SEQ ID NO: 33;
   the LCDR2 comprises SEQ ID NO: 5; and
   the LCDR3 comprises SEQ ID NO: 6;
h. the HCDR1 comprises SEQ ID NO: 30;
   the HCDR2 comprises SEQ ID NO: 44 or SEQ ID NO: 88;
   the HCDR3 comprises SEQ ID NO: 32;
   the LCDR1 comprises SEQ ID NO: 33;
   the LCDR2 comprises SEQ ID NO: 5; and
   the LCDR3 comprises SEQ ID NO: 6; or
i. the HCDR1 comprises SEQ ID NO: 30;
   the HCDR2 comprises SEQ ID NO: 98;
   the HCDR3 comprises SEQ ID NO: 32;
   the LCDR1 comprises SEQ ID NO: 33;
   the LCDR2 comprises SEQ ID NO: 5; and
   the LCDR3 comprises SEQ ID NO: 6.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 31, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 34, and a VL comprising SEQ ID NO: 35. In some embodiments, the antibody or antigen binding fragment thereof comprises a HC comprising SEQ ID NO: 36, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 40, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 41, and a VL comprises SEQ ID NO: 35. In some embodiments, the antibody or antigen binding fragment thereof comprises a HC comprising SEQ ID NO: 42, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 44, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 45, and a VL comprises SEQ ID NO: 35. In some embodiments, the antibody or antigen binding fragment thereof comprises a HC comprising SEQ ID NO: 46, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises the HCDR1 comprises SEQ ID NO: 48, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments the antibody or antigen binding fragment thereof comprises a VH comprising SEQ ID NO: 49, and a VL comprising SEQ ID NO: 35. In some embodiments, the antibody or antigen binding fragment thereof comprises a HC comprising SEQ ID NO: 50, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 52, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof, comprises a VH comprising SEQ ID NO: 53, and a VL comprising SEQ ID NO: 35. In some embodiments, the antibody or antigen binding fragment thereof comprises a HC comprising SEQ ID NO: 54, and a light chain (LC) comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 2, the HCDR3 comprises SEQ ID NO: 56, the LCDR1 comprises SEQ ID NO: 33, the LCDR2 comprises SEQ ID NO: 5, and the LCDR3 comprises SEQ ID NO: 6. In some embodiments the antibody or antigen binding fragment thereof, comprises a VH comprising SEQ ID NO: 57, and a VL comprising SEQ ID NO: 35. In some embodiments the antibody or antigen binding fragment thereof, comprises a heavy chain (HC) comprising SEQ ID NO: 58, and a light chain (LC) comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 60, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof, comprises a VH comprising SEQ ID NO: 61, and a VL comprising SEQ ID NO: 35. In some embodiments, the antibody or antigen binding fragment thereof comprises a HC comprising SEQ ID NO: 62, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 2, the HCDR3 comprises SEQ ID NO: 64, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof, comprises a VH comprising SEQ ID NO: 65, and a VL comprising SEQ ID NO: 35. In some embodiments, the antibody or antigen binding fragment thereof, comprises a HC comprising SEQ ID NO: 66, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, HCDR2 comprises SEQ ID NO: 2, the HCDR3 comprises SEQ ID NO: 68, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 69, and a VL comprising SEQ ID NO: 35. In some embodiments, the antibody or antigen binding fragment thereof, comprises a HC comprising SEQ ID NO: 70, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 2, the HCDR3 comprises SEQ ID NO: 72, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 73, and a VL comprising SEQ ID NO: 35. In some embodiments, the antibody or antigen binding fragment thereof, comprises a HC comprising SEQ ID NO: 74, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 76, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 77, and a VL comprising SEQ ID NO: 35. In some embodiments, the antibody or antigen binding fragment thereof, comprises a HC comprising SEQ ID NO: 78, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 80, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 81, and a VL comprising SEQ ID NO: 35. In some embodiments, the antibody or antigen binding fragment thereof, comprises a HC comprising SEQ ID NO: 82, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 84, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 85, and a VL comprising SEQ ID NO: 35. In some embodiments, the antibody or antigen binding fragment thereof, comprises a HC comprising SEQ ID NO: 86, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 88, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, the antibody or antigen binding fragment thereof comprises a VH comprising SEQ ID NO: 89, and a VL comprising SEQ ID NO: 35. In some embodiments, the antibody or antigen binding fragment thereof, comprises a HC comprising SEQ ID NO: 90, and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 2, the HCDR3 comprises SEQ ID NO: 72, the LCDR1 comprises SEQ ID NO: 4, the LCDR2 comprises SEQ ID NO: 5, and the LCDR3 comprises SEQ ID NO: 6. In some embodiments, the antibody or antigen binding fragment thereof comprises a VH comprising SEQ ID NO: 73, and a VL comprising SEQ ID NO: 8. In some embodiments, the antibody or antigen binding fragment thereof, comprises a HC comprising SEQ ID NO: 74, and a LC comprising SEQ ID NO: 10.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 2, the HCDR3 comprises SEQ ID NO: 68, the LCDR1 comprises SEQ ID NO: 4, the LCDR2 comprises SEQ ID NO: 5, and the LCDR3 comprises SEQ ID NO: 6. In some embodiments, the antibody or antigen binding fragment thereof comprises a VH comprising SEQ ID NO: 69, and a VL comprising SEQ ID NO: 8. In some embodiments, the antibody or antigen binding fragment thereof, comprises a HC comprising SEQ ID NO: 70, and a LC comprising SEQ ID NO: 10.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 40, SEQ ID NO: 48, SEQ ID NO: 52, SEQ ID NO: 60, SEQ ID NO: 76, SEQ ID NO: 80 or SEQ ID NO: 84, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments the antibody or antigen binding fragment thereof comprises a VH comprising SEQ ID NO: 41, 49, 53, 61, 77, 81 or 85 and the VL comprises SEQ ID NO: 35. In some embodiments, the antibody or antigen binding fragment thereof, comprises a HC comprising SEQ ID NO: 42, 50, 54, 62, 78, 82, or 86 and a LC comprising SEQ ID NO: 37.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 97, the HCDR2 comprises SEQ ID NO: 2, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, $Xaa_2$ of SEQ ID NO: 97 is Valine or Arginine, $Xaa_7$ of SEQ ID NO: 97 is Arginine or Leucine, $Xaa_9$ of SEQ ID NO: 97 is Asparagine or Glycine, $Xaa_{10}$ of SEQ ID NO: 97 is Tyrosine or Isoleucine, $Xaa_{12}$ of SEQ ID NO: 97 is Leucine or Isoleucine, and $Xaa_{13}$ of SEQ ID NO: 97 is Glutamine, Valine or Glycine. In some embodiments the antibody or antigen binding fragment thereof comprises a VH comprising SEQ ID NO: 41, 49, 53, 61, 77, 81 or 85 and the VL comprises SEQ ID NO: 35. In some embodiments, the antibody or antigen binding fragment thereof, comprises a HC comprising SEQ ID NO: 42, 50, 54, 62, 78, 82, or 86 and a LC comprising SEQ ID NO: 37. In such embodiments, the anti-human MCT1 antibodies as disclosed herein have desirable binding and functional activity.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 44 or SEQ ID NO: 88, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments the antibody or antigen binding fragment thereof comprises a VH comprising SEQ ID NO: 45 or 89 and the VL comprises SEQ ID NO: 35. In some embodiments the antibody or antigen binding fragment thereof comprises a HC comprising SEQ ID NO: 46 or 90 and a LC comprising SEQ ID NO: 37. In such embodiments, the anti-human MCT1 antibodies as disclosed have desirable binding and functional activity.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 98, the HCDR3 comprises SEQ ID NO: 32, the LCDR1 comprises SEQ ID NO: 33, the LCDR2 comprises SEQ ID NO: 5, and the LCDR3 comprises SEQ ID NO: 6. In some embodiments, $Xaa_4$ of SEQ ID NO: 98 is Arginine or Serine, and $Xaa_9$ of SEQ ID NO: 98 is Isoleucine or Glutamic Acid, and $Xaa_{13}$ of SEQ ID NO: 98 is Glutamic Acid or Arginine. In some embodiments the antibody or antigen binding fragment thereof comprises a VH comprising SEQ ID NO: 45 or 89 and the VL comprises SEQ ID NO: 35. In some embodiments the antibody or antigen binding fragment thereof comprises a HC comprising SEQ ID NO: 46 or 90 and a LC comprising SEQ ID NO: 37. In such embodiments, the anti-human MCT1 antibodies as disclosed herein have desirable binding and functional activity.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 2, the HCDR3 comprises SEQ ID NO: 56, SEQ ID NO: 64, SEQ ID NO: 68, or SEQ ID NO: 72, the LCDR1 comprises SEQ ID NO: 33, the LCDR2 comprises SEQ ID NO: 5, and the LCDR3 comprises SEQ ID NO: 6. In some embodiments the antibody or antigen binding fragment thereof comprises a VH comprising SEQ ID NO: 57, 65, 69, or 73 and the VL comprises SEQ ID NO: 35. In some embodiments the antibody or antigen binding fragment thereof comprises a HC comprising SEQ ID NO: 58, 66, 70, or 74 and a LC comprising SEQ ID NO: 37. In such embodiments, the anti-human MCT1 antibodies as disclosed herein have desirable binding and functional activity.

In some embodiments, the present disclosure provides an antibody or antigen binding fragment thereof, that specifically binds human MCT1, and comprises a VH and VL, wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 30, the HCDR2 comprises SEQ ID NO: 2, the HCDR3 comprises SEQ ID NO: 99, the LCDR1 comprises SEQ ID NO: 33, the LCDR2 comprises SEQ ID NO: 5, and the LCDR3 comprises SEQ ID NO: 6. In some embodiments, $Xaa_4$ of SEQ ID NO: 99 is Arginine or Leucine, and $Xaa_6$ of SEQ ID NO: 99 is Histidine, Arginine, or Tyrosine, and $Xaa_{20}$ of SEQ ID NO: 99 is Alanine or Proline. In some embodiments the antibody or antigen binding fragment thereof comprises a VH comprising SEQ ID NO: 57, 65, 69, or 73 and the VL comprises SEQ ID NO: 35. In some embodiments the antibody or antigen binding fragment thereof comprises a HC comprising SEQ ID NO: 58, 66, 70, or 74 and a LC comprising SEQ ID NO: 37. In such embodiments, the anti-human MCT1 antibodies as disclosed herein have desirable binding and functional activity.

In some embodiments, the present disclosure provides an antibody comprising a heavy chain (HC) and a light chain (LC), wherein the HC and the LC comprise the following amino acid sequences:
  a. the HC comprises SEQ ID NO: 9 and the LC comprises SEQ ID NO: 10;
  b. the HC comprises SEQ ID NO: 9 and the LC comprises SEQ ID NO: 15;
  c. the HC comprises SEQ ID NO: 19 and the LC comprises SEQ ID NO: 15;
  d. the HC comprises SEQ ID NO: 23 and the LC comprises SEQ ID NO: 24; or
  e. the HC comprises SEQ ID NO: 28 and the LC comprises SEQ ID NO: 24.

In some embodiments, the present disclosure provides an antibody comprising a heavy chain (HC) comprising SEQ ID NO: 9, 19, 23, or 28, and a light chain (LC) comprising SEQ ID NO: 10, 15, or 24. In some embodiments, the present disclosure provides an antibody comprising a heavy chain comprising SEQ ID NO: 9, and a light chain comprising SEQ ID NO: 10. In some embodiments, the present disclosure provides an antibody comprising a heavy chain comprising SEQ ID NO: 9, and a light chain comprising SEQ ID NO: 15. In some embodiments, the present disclosure provides an antibody comprising a heavy chain comprising SEQ ID NO: 19, and a light chain comprising SEQ ID NO: 15. In some embodiments, the present disclosure provides an antibody comprising a heavy chain comprising SEQ ID NO: 23, and a light chain comprising SEQ ID NO: 24. In some embodiments, the present disclosure provides an antibody comprising a heavy chain comprising SEQ ID NO: 28, and a light chain comprising SEQ ID NO: 24.

In some embodiments, the present disclosure provides an antibody comprising a heavy chain variable region (VH) comprising SEQ ID NO: 7, 18, 21, or 27, and a light chain variable region (VL) comprising SEQ ID NO: 8, 13, or 22. In some embodiments, the VH comprises SEQ ID NO: 7 and the VL comprises SEQ ID NO: 8. In some embodiments, the VH comprises SEQ ID NO: 7 and the VL comprises or SEQ ID NO: 13. In some embodiments, the VH comprises SEQ ID NO: 18 and the VL comprises SEQ ID NO: 13. In some embodiments, the VH comprises SEQ ID NO: 21 and a VL comprises SEQ ID NO: 22. In some embodiments, the VH comprises SEQ ID NO: 27 and a VL comprises SEQ ID NO: 22.

In some embodiments, the anti-human MCT1 antibodies as disclosed herein, have modified variable regions. In some embodiments, the modifications are in the VH. In some embodiments, the modifications are in the VL. In some embodiments, the modifications are in the VH and VL. In some embodiments, the anti-human MCT1 antibodies as disclosed herein, have different human framework regions. In some embodiments the VH and the VL of the anti-human MCT1 antibodies as disclosed herein, comprise of a specific combination of framework amino acid sequences to support the particular CDR amino acid sequences as disclosed herein. In some embodiments the VH and the VL of the anti-human MCT1 antibodies as disclosed herein, have a specific combination of framework amino acid sequences, that allow for optimal presentation of the CDR amino acid sequences as disclosed herein. In some embodiments, the specific combination of framework amino acid sequences as provided herein support the particular CDR amino acid sequences provided herein, and allow for optimal presentation of the CDR amino acid sequences, providing desirable binding affinity and functional activity of the antibodies (e.g., inhibition of metabolite transport and B and/or T cell proliferation, and drive regulatory T cell differentiation) and/or developability properties and/or improved patient safety. Accordingly, in some embodiments, the anti-human MCT1 antibodies of the present disclosure have improved developability and/or safety profiles when compared to MCT1 antibodies known in the art, e.g., INX444 as described in WO19136300. In such embodiments, the anti-human MCT1 antibodies as disclosed herein have reduced immunogenicity risk when compared to INX444. In yet other embodiments, the anti-human MCT1 antibodies as disclosed herein have reduced oxidation and in culture degradation when compared to INX444. In yet other embodiments, the anti-human MCT1 antibodies as disclosed herein have eliminated or reduced nonspecific human serum protein binding when compared to INX444. In yet other embodiments, the anti-human MCT1 antibodies as disclosed herein have reduced nonspecific interactions, such as binding to purification column resin, when compared to INX444. In further embodiments, the anti-human MCT1 antibodies as disclosed herein have reduced hydrophobicity, when compared to INX444. As such, the anti-human MCT1 antibodies as disclosed herein have reduced challenges in downstream purification and analytical processes, and/or improved pharmacokinetic profiles when compared to INX444.

In some embodiments, the anti-human MCT1 antibodies as disclosed herein, have a modified human IgG1 or human IgG4 constant region.

In some embodiments, the anti-human MCT1 antibody as disclosed herein, has a modified Fc region (e.g., a modified IgG1, IgG2, IgG3 or IgG4 Fc region) that has reduced or eliminated Fc effector functions. Such anti-human MCT1 antibodies as described herein show reduced or eliminated binding to the FcγR receptors, thus have reduced cytotoxicity, when compared to the antibodies comprising the wild type IgG Fc region. Patient safety can be improved with sufficiently reduced or eliminated effector functions of such anti-human MCT1 antibodies comprising a modified Fc region.

In some embodiments, the anti-human MCT1 antibody has a human IgG1 isotype. In such embodiments, the anti-human MCT1 antibodies described herein have a modified IgG1 Fc region having eliminated Fc effector functions, i.e., IgG1 Fc effector null. For example, such anti-human MCT1 antibodies comprise an IgG1 Fc region comprising amino acid substitutions L234A, L235E, G237A, A330S, and P331S show reduced binding to FcγR and C1q receptors (all amino acid residues are numbered according to the EU Index numbering). In some embodiments the anti-human MCT1 antibodies described herein have a modified human IgG1 Fc region comprising an alanine at residue 234, a glutamic acid at residue 235, an alanine at residue 237, a serine at residue 330, and a serine at residue 331 (all residues are numbered according to the EU Index numbering) also referred to as IgG1EN Fc region. In other embodiments, the anti-human MCT1 antibodies describe herein have a modified human IgG1 Fc region comprising an alanine at residue 234, an alanine at residue 235, an arginine at residue 269, and an alanine at residue 322 (all residues are numbered according to the EU Index numbering) also referred to as INX LALA Fc region.

Different allotypes (polymorphisms) of human IgG1, for example, G1m3, G1m17, G1 ml and G1m2 allotypes, have been described before (Jefferis R., et al., mAbs 1(4): 1-7, 2009; Webster C., et al., mAbs 2016, 8 (2): 253-263). The heavy chain of human IgG1 protein may express as G1m3, G1m17,1 or G1m17,1,2 allotype; no allotypes have been defined for IgG4 (Jefferis R., et al., mAbs 1(4): 1-7, 2009). In some embodiments, the anti-human MCT1 antibodies described herein comprise a heavy chain of the IgG1 G1m3 allotype, which comprises arginine at position 214, glutamate at position 356 and methionine at position 358 (all residues numbered according to the EU Index numbering). In some embodiments, the anti-human MCT1 antibodies described herein comprise a heavy chain of the IgG1 G1m17,1 allotype, which comprises lysine at position 214, aspartate at position 356, and leucine at position 358 (all residues numbered according to the EU Index numbering).

Human MCT1 is expressed on activated T cells and B cells. The anti-human MCT1 antibodies described herein, upon binding to MCT1, reduce, suppress, diminish, or otherwise inhibit the MCT1 functions in MCT1 expressing cells, such as activated T cells and B cells. In such embodiments, the anti-human MCT1 antibody or antigen binding fragment thereof, binds human MCT1 and inhibits MCT1 mediated transport, CD4 and CD8 T cell proliferation and/or B cell proliferation. In some embodiments, the anti-human MCT1 antibody or antigen binding fragment thereof, inhibits MCT1 mediated transport in T cells and leads to changes in T cell differentiation. Such changes in T cell differentiation may further enhance differentiation of regulatory T cells (Tregs). Regulation of regulatory T cells include, but are not limited to FoxP3⁺ and Foxp3⁻ Tregs. In some embodiments, the antibody or antigen binding fragment thereof of the present disclosure binds human MCT1 and inhibits MCT1 mediated transport by about 10%, about 20%, about 30%, about 40%, about 50%, about 60%, about 70%, about 80%, about 90%, or about 100%. In some embodiments, the antibody or antigen binding fragment thereof of the present disclosure binds human MCT1 and inhibits MCT1 mediated metabolite transport by about 10%, about 20%, about 30%, about 40%, about 50%, about 60%, about 70%, about 80%, about 90%, or about 100%. In some embodiments, the antibody or antigen binding fragment thereof of the present disclosure binds human MCT1 and inhibits MCT1 mediated pyruvate transport by about 10%, about 20%, about 30%, about 40%, about 50%, about 60%, about 70%, about 80%, about 90%, or about 100%. In some embodiments, the antibody or antigen binding fragment thereof of the present disclosure binds human MCT1 and inhibits MCT1 mediated lactate transport by about 10%, about 20%, about 30%, about 40%, about 50%, about 60%, about 70%, about 80%, about 90%, or about 100%. In some embodiments, the antibody or antigen binding fragment thereof of the present disclosure binds human MCT1 on T cells and inhibits MCT1 mediated CD4 T cell proliferation by about 10%, about 20%, about 30%, about 40%, about 50%, about 60%, about 70%, about 80%, about 90%, or about 100%. In some embodiments, the antibody or antigen binding fragment thereof of the present disclosure binds human MCT1 on T cells and inhibits MCT1 mediated CD8 T cell proliferation by about 10%, about 20%, about 30%, about 40%, about 50%, about 60%, about 70%, about 80%, about 90%, or about 100%. In some embodiments, the antibody or antigen binding fragment thereof of the present disclosure binds human MCT1 on T cells and inhibits MCT1 mediated CD4 and CD8 T cell proliferation by about 10%, about 20%, about 30%, about 40%, about 50%, about 60%, about 70%, about 80%, about 90%, or about 100%. In some embodiments, the antibody or antigen binding fragment thereof of the present disclosure binds human MCT1 on B cells and inhibits MCT1 mediated B cell proliferation by about 10%, about 20%, about 30%, about 40%, about 50%, about 60%, about 70%, about 80%, about 90%, or about 100%.

In some embodiments, the anti-human MCT1 antibodies of the present disclosure bind human MCT1 and inhibit human MCT1 mediated transport in a conformational dependent manner.

In some embodiments the present disclosure provides nucleic acids encoding a heavy chain or light chain, or a VH or VL, of the novel anti-human MCT1 antibodies, or vectors comprising such nucleic acids.

In some embodiments, the present disclosure provides a nucleic acid comprising a sequence of SEQ ID NO: 11, 20, 25, 29, 38, 43, 47, 51, 55, 59, 63, 67, 71, 75, 79, 83, 87, 91, 12, 17, 26, or 39.

In some embodiments, nucleic acids encoding a heavy chain or light chain of the antibodies specifically binding human MCT1 are provided. In some embodiments nucleic acids comprising a sequence encoding SEQ ID NO: 9, 19, 23, 28, 36, 42, 46, 50, 54, 58, 62, 66, 70, 74, 78, 82, 86, 90, 10, 15, 24, or 37 are provided. In some embodiments, nucleic acids comprising a sequence encoding an antibody heavy chain that comprises SEQ ID NO: 9, 19, 23, 28, 36, 42, 46, 50, 54, 58, 62, 66, 70, 74, 78, 82, 86, or 90 are provided. For example, the nucleic acid can comprise a sequence selected from SEQ ID NO: 11, 20, 25, 29, 38, 43, 47, 51, 55, 59, 63, 67, 71, 75, 79, 83, 87, or 91. In some embodiments, nucleic acids comprising a sequence encoding an antibody light chain that comprises SEQ ID NO: 10, 15, 24, or 37 is provided. For example, the nucleic acid can comprise a sequence selected from SEQ ID NO:12, 17, 26, or 39.

In some embodiments of the present disclosure, nucleic acids encoding a VH or VL of the antibodies specifically binding human MCT1 are provided. In some embodiments, nucleic acids comprising a sequence encoding SEQ ID NO: 7, 18, 21, 27, 34, 41, 45, 49, 53, 57, 61, 65, 69, 73, 77, 81, 85, 89, 8, 13, 22, or 35 are provided. In some embodiments, nucleic acids comprising a sequence encoding an antibody VH that comprises SEQ ID NO: 7, 18, 21, 27, 34, 41, 45, 49, 53, 57, 61, 65, 69, 73, 77, 81, 85, or 89 are provided. In some embodiments, nucleic acids comprising a sequence encoding an antibody VL that comprises SEQ ID NO: 8, 13, 22, or 35 are provided.

Some embodiments of the present disclosure provide vectors comprising a nucleic acid sequence encoding an antibody heavy chain or light chain. For example, such vectors can comprise a nucleic acid sequence encoding SEQ ID NO: 9, 19, 23, 28, 36, 42, 46, 50, 54, 58, 62, 66, 70, 74, 78, 82, 86, or 90. In some embodiments, the vector comprises a nucleic acid sequence encoding SEQ ID NO: 10, 15, 24, or 37.

Provided herein are also vectors comprising a nucleic acid sequence encoding an antibody VH or VL. For example, such vectors can comprise a nucleic acid sequence encoding SEQ ID NO: 7, 18, 21, 27, 34, 41, 45, 49, 53, 57, 61, 65, 69, 73, 77, 81, 85, or 89. In some embodiments, the vector comprises a nucleic acid sequence encoding SEQ ID NO: 8, 13, 22, or 35.

Provided herein are also vectors comprising a first nucleic acid sequence encoding an antibody heavy chain and a second nucleic acid sequence encoding an antibody light chain. In some embodiments, the vector comprises a first nucleic acid sequence encoding SEQ ID NO: 9, 19, 23, 28, 36, 42, 46, 50, 54, 58, 62, 66, 70, 74, 78, 82, 86, or 90. and a second nucleic acid sequence encoding SEQ ID NO: 10, 15, 24, or 37.

In some embodiments, the vector comprises a first nucleic acid sequence encoding SEQ ID NO: 9 and a second nucleic acid sequence encoding SEQ ID NO: 10. In some embodiments, the vector comprises a first nucleic acid sequence encoding SEQ ID NO: 9 and a second nucleic acid sequence encoding SEQ ID NO: 15. In some embodiments, the vector comprises a first nucleic acid sequence encoding SEQ ID NO: 19 and a second nucleic acid sequence encoding SEQ ID NO: 15. In some embodiments, the vector comprises a first nucleic acid sequence encoding SEQ ID NO: 23 and a second nucleic acid sequence encoding SEQ ID NO: 24. In some embodiments, the vector comprises a first nucleic acid sequence encoding SEQ ID NO: 28 and a second nucleic acid sequence encoding SEQ ID NO: 24. In some embodiments, the vector comprises a first nucleic acid sequence encoding SEQ ID NO: 36 and a second nucleic acid sequence encoding SEQ ID NO: 37. In some embodiments, the vector comprises a first nucleic acid sequence encoding SEQ ID NO: 42 and a second nucleic acid sequence encoding SEQ ID NO: 37. In some embodiments, the vector comprises a first nucleic acid sequence encoding SEQ ID NO: 46 and a second nucleic acid sequence encoding SEQ ID NO: 37. In some embodiments, the vector comprises a first nucleic acid sequence encoding SEQ ID NO: 50 and a second nucleic acid sequence encoding SEQ ID NO: 37. In some embodiments, the vector comprises a first nucleic acid sequence encoding SEQ ID NO: 54 and a second nucleic acid sequence encoding SEQ ID NO: 37. In some embodiments, the vector comprises a first nucleic acid sequence encoding SEQ ID NO: 58 and a second nucleic acid sequence encoding SEQ ID NO: 37. In some embodiments, the vector comprises a first nucleic acid sequence encoding SEQ ID NO: 62 and a second nucleic acid sequence encoding SEQ ID NO: 37. In some embodiments, the vector comprises a first nucleic acid sequence encoding SEQ ID NO: 66 and a second nucleic acid sequence encoding SEQ ID NO: 37. In some embodiments, the vector comprises a first nucleic acid sequence encoding SEQ ID NO: 70 and a second nucleic acid sequence encoding SEQ ID NO: 37. In some embodiments, the vector comprises a first nucleic acid sequence encoding SEQ ID NO: 74 and a second nucleic acid sequence encoding SEQ ID NO: 37. In some embodiments, the vector comprises a first nucleic acid sequence encoding SEQ ID NO: 78 and a second nucleic acid sequence encoding SEQ ID NO: 37. In some embodiments, the vector comprises a first nucleic acid sequence encoding SEQ ID NO: 82 and a second nucleic acid sequence encoding SEQ ID NO: 37. In some embodiments, the vector comprises a first nucleic acid sequence encoding SEQ ID NO: 86 and a second nucleic acid sequence encoding SEQ ID NO: 37. In some embodiments, the vector comprises a first nucleic acid sequence encoding SEQ ID NO: 90 and a second nucleic acid sequence encoding SEQ ID NO: 37. In some embodiments, the vector comprises a first nucleic acid sequence encoding SEQ ID NO: 74 and a second nucleic acid sequence encoding SEQ ID NO: 10. In some embodiments, the vector comprises a first nucleic acid sequence encoding SEQ ID NO: 70 and a second nucleic acid sequence encoding SEQ ID NO: 10.

Also provided are compositions comprising a first vector comprising a nucleic acid sequence encoding an antibody heavy chain, and a second vector comprising a nucleic acid sequence encoding an antibody light chain. In some embodiments, the composition comprises a first vector comprising a nucleic acid sequence encoding SEQ ID NO: 9, 19, 23, 28, 36, 42, 46, 50, 54, 58, 62, 66, 70, 74, 78, 82, 86, or 90 and a second nucleic acid sequence encoding SEQ ID NO: 10, 15, 24, or 37.

In some embodiments, the composition comprises a first vector comprising a nucleic acid sequence encoding SEQ ID NO: 9 and a second vector comprising a nucleic acid sequence encoding SEQ ID NO: 10. In some embodiments, the composition comprises a first vector comprising a nucleic acid sequence encoding SEQ ID NO: 9 and a second vector comprising a nucleic acid sequence encoding SEQ ID NO: 15. In some embodiments, the composition comprises a first vector comprising a nucleic acid sequence encoding SEQ ID NO: 19 and a second vector comprising a nucleic acid sequence encoding SEQ ID NO: 15. In some embodiments, the composition comprises a first vector comprising a nucleic acid sequence encoding SEQ ID NO: 23 and a second vector comprising a nucleic acid sequence encoding SEQ ID NO: 24. In some embodiments, the composition comprises a first vector comprising a nucleic acid sequence encoding SEQ ID NO: 28 and a second vector comprising a nucleic acid sequence encoding SEQ ID NO: 24. In some embodiments, the composition comprises a first vector comprising a nucleic acid sequence encoding SEQ ID NO: 36 and a second vector comprising a nucleic acid sequence encoding SEQ ID NO: 37. In some embodiments, the composition comprises a first vector comprising a nucleic acid sequence encoding SEQ ID NO: 42 and a second vector comprising a nucleic acid sequence encoding SEQ ID NO: 37. In some embodiments, the composition comprises a first vector comprising a nucleic acid sequence encoding SEQ ID NO: 46 and a second vector comprising a nucleic acid sequence encoding SEQ ID NO: 37. In some embodiments, the composition comprises a first vector comprising a nucleic acid sequence encoding SEQ ID NO: 50 and a second vector comprising a nucleic acid sequence encoding SEQ ID NO: 37. In some embodiments, the composition comprises a first vector comprising a nucleic acid sequence encoding SEQ ID NO: 54 and a second vector comprising a nucleic acid sequence encoding SEQ ID NO: 37. In some embodiments, the composition comprises a first vector comprising a nucleic acid sequence encoding SEQ ID NO: 58 and a second vector comprising a nucleic acid sequence encoding SEQ ID NO: 37. In some embodiments, the composition comprises a first vector comprising a nucleic acid sequence encoding SEQ ID NO: 62 and a second vector comprising a nucleic acid sequence encoding SEQ ID NO: 37. In some embodiments, the composition comprises a first vector comprising a nucleic acid sequence encoding SEQ ID NO: 66 and a second vector comprising a nucleic acid sequence encoding SEQ ID NO: 37. In some embodiments, the composition comprises a first vector comprising a nucleic acid sequence encoding SEQ ID NO: 70 and a second vector comprising a nucleic acid sequence encoding SEQ ID NO: 37. In some embodiments, the composition comprises a first vector comprising a nucleic acid sequence encoding SEQ ID NO: 74 and a second vector comprising a nucleic acid sequence encoding SEQ ID NO: 37. In some embodiments, the composition comprises a first vector comprising a nucleic acid sequence encoding SEQ ID NO: 78 and a second vector comprising a nucleic acid sequence encoding SEQ ID NO: 37. In some embodiments, the composition comprises a first vector comprising a nucleic acid sequence encoding SEQ ID NO: 82 and a second vector comprising a nucleic acid sequence encoding SEQ ID NO: 37. In some embodiments, the composition comprises a first vector comprising a nucleic acid sequence encoding SEQ ID NO: 86 and a second vector comprising a nucleic acid sequence encoding SEQ ID NO: 37. In some embodiments, the composition comprises a first vector comprising a nucleic acid sequence encoding SEQ ID NO: 90 and a second vector comprising a nucleic acid sequence encoding SEQ ID NO: 37. In some embodiments, the composition comprises a first vector comprising a nucleic acid sequence encoding SEQ ID NO: 74 and a second vector comprising a nucleic acid sequence encoding SEQ ID NO: 10. In some embodiments, the composition comprises a first vector comprising a nucleic acid sequence encoding SEQ ID NO: 70 and a second vector comprising a nucleic acid sequence encoding SEQ ID NO: 10.

Nucleic acids of the present disclosure may be expressed in a host cell, for example, after the nucleic acids have been operably linked to an expression control sequence. Expression control sequences capable of expression of nucleic acids to which they are operably linked are well known in the art. An expression vector may include a sequence that encodes one or more signal peptides that facilitate secretion of the polypeptide(s) from a host cell. Expression vectors containing a nucleic acid of interest (e.g., a nucleic acid encoding a heavy chain or light chain of an antibody) may be transferred into a host cell by well-known methods, e.g., stable or transient transfection, transformation, transduction or infection. Additionally, expression vectors may contain one or more selection markers, e.g., tetracycline, neomycin, and dihydrofolate reductase, to aide in detection of host cells transformed with the desired nucleic acid sequences.

In another aspect, provided herein are cells, e.g., host cells, comprising the nucleic acids, vectors, or nucleic acid compositions described herein. A host cell may be a cell stably or transiently transfected, transformed, transduced or infected with one or more expression vectors expressing all or a portion of an antibody described herein. In some embodiments, a host cell may be stably or transiently transfected, transformed, transduced, or infected with an expression vector expressing HC and LC polypeptides of an antibody of the present disclosure. In some embodiments, a host cell may be stably or transiently transfected, transformed, transduced, or infected with a first vector expressing HC polypeptides and a second vector expressing LC polypeptides of an antibody described herein. Such host cells, e.g., mammalian host cells, can express the antibodies that specifically bind human MCT1 as described herein. Mammalian host cells known to be capable of expressing antibodies include CHO cells, HEK293 cells, COS cells, and NS0 cells.

In some embodiments, the cell, e.g., host cell, comprises a vector comprising a first nucleic acid sequence encoding SEQ ID NO: 9, 19, 23, 28, 36, 42, 46, 50, 54, 58, 62, 66, 70, 74, 78, 82, 86, or 90 and a second nucleic acid sequence encoding SEQ ID NO: 10, 15, 24, or 37.

In some embodiments, the cell, e.g., host cell, comprises a first vector comprising a nucleic acid sequence encoding SEQ ID NO: 9, 19, 23, 28, 36, 42, 46, 50, 54, 58, 62, 66, 70, 74, 78, 82, 86, or 90 and a second vector comprising a nucleic acid sequence encoding SEQ ID NO: 10, 15, 24, or 37.

In some embodiments, the cell comprises a first vector comprising a nucleic acid sequence encoding SEQ ID NO: 9, 70, or 74, and a second vector comprising a nucleic acid sequence encoding SEQ ID NO: 10. In some embodiments the cell comprises a first vector comprising a nucleic acid sequence encoding SEQ ID NO: 9 or 19, and a second vector comprising a nucleic acid sequence encoding SEQ ID NO: 15. In some embodiments, the cell comprises a first vector comprising a nucleic acid sequence encoding SEQ ID NO: 23 or 28, and a second vector comprising a nucleic acid sequence encoding SEQ ID NO: 24. In some embodiments, the cell comprises a first vector comprising a nucleic acid sequence encoding SEQ ID NO: 36, 42, 46, 50, 54, 58, 62, 66, 70, 74, 78, 82, 86, or 90, and a second vector comprising a nucleic acid sequence encoding SEQ ID NO: 37.

The present disclosure further provides a process for producing an antibody or antigen binding fragments thereof that specifically binds human MCT1 described herein by culturing the host cell described above, e.g., a mammalian host cell, under conditions such that the antibody is expressed and recovering the expressed antibody from the culture medium. The culture medium, into which an antibody has been secreted, may be purified by conventional techniques. Various methods of protein purification may be employed, and such methods are known in the art and described, for example, in Deutscher, Methods in Enzymology 182: 83-89 (1990) and Scopes, Protein Purification: Principles and Practice, 3rd Edition, Springer, N.Y. (1994).

The present disclosure further provides antibodies or antigen binding fragments thereof produced by any of the processes described herein.

In another aspect, provided herein are pharmaceutical compositions comprising an antibody, nucleic acid, or vector described herein. Such pharmaceutical compositions can also comprise one or more pharmaceutically acceptable excipient, diluent, or carrier. Pharmaceutical compositions can be prepared by methods well known in the art (e.g., *Remington: The Science and Practice of Pharmacy*, 22nd ed. (2012), A. Loyd et al., Pharmaceutical Press).

In some embodiments, the anti-human MCT1 antibodies, nucleic acids, vectors, or pharmaceutical compositions described herein can be used to inhibit activated T cells and/or B cells and to treat conditions associated with overactive T cells and B cells, such as autoimmunity, allergy, or inflammatory conditions. In some embodiments, the anti-human MCT1 antibodies, nucleic acids, vectors, or pharmaceutical compositions described herein can be used to increase the activity or numbers of regulatory T cells and to treat conditions associated with overactive T cells and B cells, such as autoimmunity, allergy, or inflammatory conditions. Such autoimmune, inflammatory, and allergic conditions include, for example, rheumatoid arthritis (RA), psoriatic arthritis, psoriasis, scleroderma, multiple sclerosis, lupus, inflammatory bowel disease (IBD), immune thrombocytopenia (ITP), diabetes, graft versus host disease (GvHD), sarcoidosis, allergic asthma, and hepatitis-associated hepatotoxicity. These anti-human MCT1 antibodies may also be used for treating transplant or cell therapy recipient by inhibiting unwanted T cell immune responses against transplanted cells, tissues or organs, such as tissue grafts, CAR-T cell therapy or gene therapy constructs or cells containing the constructs.

In some embodiment, the present disclosure provides methods of treating an autoimmune condition in a subject in need thereof, comprising administering to the subject a therapeutically effective amount of an anti-human MCT1 antibody, a nucleic acid encoding such an antibody, a vector comprising such a nucleic acid, or a pharmaceutical composition comprising such an antibody as provided herein. Examples of autoimmune conditions include systemic lupus erythematosus, inflammatory bowel disease, rheumatoid arthritis, psoriasis, or multiple sclerosis. In further embodiment, the present disclosure provides methods of treating an allergic condition, inflammatory condition, metabolic disorder, transplant or cell therapy recipient, MCT1-positive cancer, exercise-induced hyperinsulinism (EIHI) condition, or polycystic kidney disease (ADPKD) in a subject in need thereof, the method comprising administering to the subject a therapeutically effective amount of an antibody, a nucleic acid encoding such an antibody, a vector comprising such a nucleic acid, or a pharmaceutical composition comprising such an antibody as provided herein. The antibodies, nucleic acids, vectors, or pharmaceutical compositions described herein may be administered by parenteral routes (e.g., subcutaneous, and intravenous).

In some embodiment, the present disclosure provides anti-human MCT1 antibodies, nucleic acids, vectors, or pharmaceutical compositions described herein for use in therapy. Furthermore, the present disclosure also provides anti-human MCT1 antibodies, nucleic acids, vectors, cells, or pharmaceutical compositions described herein for use in the treatment of an autoimmune condition, an allergic condition, inflammatory condition, metabolic disorder, transplant, or cell therapy recipient, MCT1 positive cancer, EIHI condition, or ADPKD. In some embodiments, provided herein are anti-human MCT1 antibodies, nucleic acids, vectors, cells, or pharmaceutical compositions described herein for use in the treatment of an autoimmune condition, e.g., systemic lupus erythematosus, inflammatory bowel disease, rheumatoid arthritis, psoriasis or multiple sclerosis.

In some embodiments, the present disclosure provides the use of an anti-human MCT1 antibodies, nucleic acid, vector, cell, or pharmaceutical composition described herein for use in the manufacture of a medicament for the treatment of an autoimmune condition, an allergic condition, inflammatory condition, metabolic disorder, transplant, or cell therapy recipient, MCT1 positive cancer, EIHI condition, or ADPKD.

One potential advantage of the methods and therapeutic uses disclosed herein is the possibility of producing marked and/or prolonged relief in a patient suffering from an autoimmune condition, allergic disease, inflammatory condition, metabolic disorder, transplant or cell therapy recipient, MCT1 positive cancer, EIHI condition, or ADPKD, with an acceptable developability and/or safety profile including acceptable immunogenicity, tolerability, toxicities and/or adverse events, so that the patient benefits from the treatment method overall.

The term "MCT1" as used herein, unless stated otherwise, refers to any native, mature MCT1 that results from processing of an MCT1 precursor protein in a cell. The term includes MCT1 from any vertebrate source, including mammals such as primates (e.g., humans and cynomolgus or rhesus monkeys) and rodents (e.g., mice and rats), unless otherwise indicated. The term also includes naturally occurring variants of MCT1, e.g., splice variants or allelic variants. The amino acid sequence of an example of human MCT1 is known in the art, e.g., NCBI reference sequence number NP_003042.3 (SEQ ID NO: 95). The amino acid sequence of an example of cynomolgus monkey MCT1 is also known in the art, e.g., UniProt accession number A0A2K5VB69 (SEQ ID NO: 96). The term "human MCT1" is used herein to refer collectively to all known human MCT1 isoforms and polymorphic forms.

The term "antibody," as used herein, refers to an immunoglobulin molecule that binds an antigen. Embodiments of an antibody include a monoclonal antibody, polyclonal antibody, human antibody, humanized antibody, chimeric antibody, bispecific or multispecific antibody, or conjugated antibody. The antibodies can be of any class (e.g., IgG, IgE, IgM, IgD, IgA), and any subclass (e.g., IgG1, IgG2, IgG3, IgG4).

An exemplary antibody is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. The heavy chain constant region refers to a region of an antibody, which comprises the Fc region and CH1 domain of the antibody heavy chain. Each light chain is comprised of a light chain variable region (VL) and a light chain constant region. The IgG isotype may be further divided into subclasses (e.g., IgG1, IgG2, IgG3, and IgG4). The numbering of the amino acid residues in the constant region is based on the EU index as in Kabat. Kabat et al, *Sequences of Proteins of Immunological Interest,* 5th edition, Bethesda, MD: U.S. Dept. of Health and Human Services, Public Health Service, National Institutes of Health (1991). The term EU Index numbering or EU numbering is used interchangeably herein.

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on at www.imgt.org; see Lefranc et al., Nucleic Acids Res. 1999; 27:209-212). The CDR regions of the anti-human MCT1 antibodies described herein, are defined by a combination of the definitions described above.

Embodiments of the present disclosure also include antibody fragments or antigen binding fragments, which comprise at least a portion of an antibody retaining the ability to specifically interact with an antigen such as Fab, Fab', F(ab')2, Fv fragments, scFv, scFab, disulfide-linked Fvs (sdFv), a Fd fragment or linear antibodies, which may be for example, fused to an Fc region or an IgG heavy chain constant region.

The term "Fc region" as used herein, refers to a region of an antibody, which comprises the CH2 and CH3 domains of the antibody heavy chain. Optionally, the Fc region may include a portion of the hinge region or the entire hinge region of the antibody heavy chain. Biological activities such as effector function are attributable to the Fc region, which vary with the antibody isotype. Examples of antibody effector functions include, Fc receptor binding, antibody-dependent cell mediated cytotoxicity (ADCC), antibody-dependent cell mediated phagocytosis (ADCP), C1q binding, complement dependent cytotoxicity (CDC), phagocytosis, down regulation of cell surface receptors (e.g. B cell receptor); and B cell activation.

The term "Fc receptor" or "FcR" describes a receptor that binds to the Fc region of an antibody. In some embodiments, the FcR is a native sequence human FcR. An "Fc gamma receptor" or "FcγR" is an FcR that binds an IgG antibody and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have amino acid sequences that differ primarily in the cytoplasmic domains thereof. FcRs are reviewed in Ravetch and Kinet, *Ann. Rev. Immunol.,* 9:457-92 (1991); Capel et al., Immunomethods, 4:25-34 (1994); and de Haas et al, *J. Lab. Clin. Med.,* 126:330-41 (1995).

The terms "bind" and "binds" as used herein, are intended to mean, unless indicated otherwise, the ability of a protein or molecule to form a chemical bond or attractive interaction with another protein or molecule, which results in proximity of the two proteins or molecules as determined by common methods known in the art.

The terms "nucleic acid" as used herein, refer to polymers of nucleotides, including single-stranded and/or doublestranded nucleotide-containing molecules, such as DNA, cDNA, and RNA molecules, incorporating native, modified, and/or analogs of, nucleotides. Polynucleotides of the present disclosure may also include substrates incorporated therein, for example, by DNA or RNA polymerase or a synthetic reaction.

The term "subject" as used herein, refers to a mammal, including, but are not limited to, a human, chimpanzee, ape, monkey, cattle, horse, sheep, goat, swine, rabbit, dog, cat, rat, mouse, guinea pig, and the like. Preferably, the subject is a human.

The term "therapeutically effective amount", as used herein, refers to an amount of a protein or nucleic acid or vector or composition that will elicit the biological or medical response of a subject, for example, reduction or inhibition of an enzyme or a protein activity, or ameliorate symptoms, alleviate conditions, slow or delay disease progression, or prevent a disease, etc. In a non-limiting embodiment, the term "a therapeutically effective amount" refers to the amount necessary (at dosages and for periods of time and for the means of administration) of a protein or nucleic acid or vector or composition that, when administered to a subject, is effective to at least partially alleviate, inhibit, prevent and/or ameliorate a condition, or a disorder or a disease to achieve the desired therapeutic result. A therapeutically effective amount of the protein or nucleic acid or vector or composition may vary according to factors such as the disease state, age, sex, and weight of the individual, and the ability of the protein or nucleic acid or vector or composition to elicit a desired response in the individual. A therapeutically effective amount is also one in which any toxic or detrimental effects of the protein or nucleic acid or vector or composition of the present invention are outweighed by the therapeutically beneficial effects.

The term "inhibits" as used herein, refers to for example, a reduction, lowering, slowing, decreasing, stopping, disrupting, abrogating, antagonizing, or blocking of a biological response or activity, but does not necessarily indicate a total elimination of a biological response.

The term "treatment" or "treating" as used herein, refers to all processes wherein there may be a slowing, controlling, delaying, or stopping of the progression of the disorders or disease disclosed herein, or ameliorating disorder or disease symptoms, but does not necessarily indicate a total elimination of all disorder or disease symptoms. Treatment includes administration of a protein or nucleic acid or vector or composition for treatment of a disease or condition in a patient, particularly in a human.

The term "about" as used herein, means within 5%.

As used herein, the term "a", "an", "the", and similar terms used in the context of the present disclosure (especially in the context of the claims) are to be construed to cover both the singular and plural unless otherwise indicated herein or clearly contradicted by the context.

EXAMPLES

Figure 1:
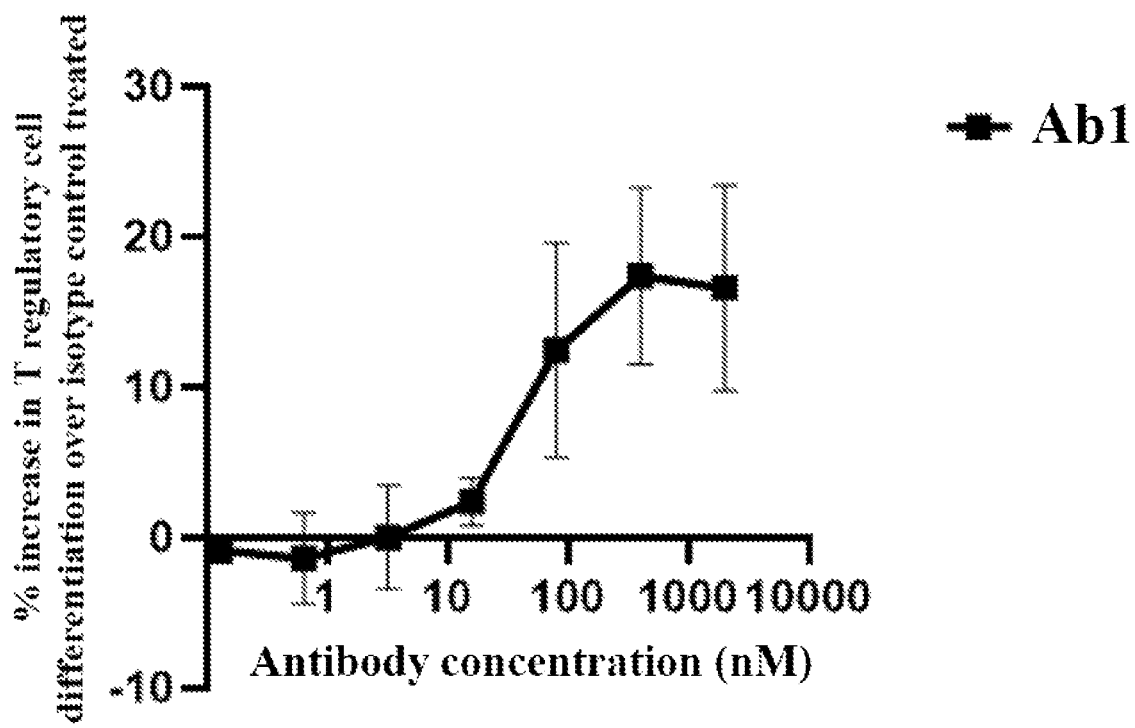
FIG. 1 shows anti-human MCT1 antibody Ab1 binds human MCT1 and increases regulatory T cell differentiation in a concentration dependent manner.

The following examples are offered to illustrate, but not to limit, the claimed invention.

Example 1: Antibody Generation and Engineering of Humanized MCT1 Antibodies (Anti-Human MCT1 Antibodies)

Antibody engineering and generation: Humanized MCT1 antibodies were generated by engineering and empirical testing of anti-MCT1 parental rat monoclonal antibody M1056 (described in WO19136300) through humanization and CDR engineering. Previously described monoclonal antibody INX444 [described in WO19136300] was derived from parent rat antibody M1056 through humanization, CDR engineering, and light chain shuffling. However, analysis of INX444 identified several developability challenges and risk factors. Significant oxidation and clipping were observed in cell culture, instability due to oxidation, were observed for INX444 non-specific interactions with column resin and serum proteins, creating challenges in downstream analytical and manufacturing processes, which impact potential clinical development and or commercial potential of this antibody. Further, rapid clearance and high immunogenicity risk of INX444 were observed. The VH and VL sequences of INX444 each contain at least five non-human framework residues, as well as CDR mutations introduced into the VH parent rat antibody sequence and non-parental VL CDR segments introduced by light chain shuffling. To overcome the developability challenges and immunogenicity disadvantages of INX444, an extensive humanization, and engineering approach was taken to de novo humanize and engineer the parental rat M1056 antibody. Following framework replacement, the newly humanized antibodies (anti-human MCT1 antibodies) were engineered in their CDRs, and IgG constant regions to further improve desired properties.

The anti-human MCT1 antibodies described herein can be synthesized and purified by well-known methods. An appropriate host cell, such as Chinese hamster ovarian cells (CHO), can be either transiently or stably transfected with an expression system for secreting antibodies using a predetermined HC:LC vector ratio if two vectors are used, or a single vector system encoding both heavy chain and light chain. Clarified media, into which the antibody has been secreted, can be purified using the commonly used techniques.

Antibody Framework engineering: To overcome framework and CDR amino acid residues impacting the immunogenicity properties that were observed in the INX444, a different humanization and engineering approach was selected. Briefly, the parental rat antibody M1056 was humanized using a framework library approach. For the framework library, twelve human VH framework germline genes (1-24, 1-46, 1-69, 2-5, 3-15, 3-23, 3-53, 3-72, 4-04, 4-39, 5-51, and 6-01) and eight human VL framework genes (A-19, A-26, A-27, B-2, B-3, L-2, L-12, and O-2) containing M1056's CDRs following two different CDR definitions (generating two 96 HC/LC combination libraries) were synthesized and cloned into heavy and light chain human IgG1 expression vectors. All 192 combinations were generated, and transiently transfected into Chinese Hamster Ovary (CHO) cells. Supernatants from the transfected CHO cells were assessed for functional activity, such as inhibition of MCT1 transporter activity, and in some cases, for MCT1 cell binding, T cell inhibition, stability, and immunogenicity.

Screening of the human framework libraries revealed 21 of the 192 fully human framework antibodies displaying the CDRs derived from the parent rat antibody (M1056) exhibited appreciable functional activity as determined by the bromopyruvate transport assay. The remaining antibodies did not show significant activities. After preliminary assessment for stability and immunogenicity risks, 12 framework antibody combinations were further characterized experimentally to evaluate properties such as cell-based MCT1 binding, functional activity by inhibition of T cell proliferation, biophysical properties, and human serum binding. These analyses led to the selection of five antibodies (namely: Ab1, Ab2, Ab3, Ab4, and Ab5) as shown in Tables 1 and 2, for further in-depth characterization, particularly focusing on immunogenicity assessments. These five framework antibodies showed significant improvements in developability, standard platform purification fitness, and critical readouts evaluating clinical immunogenicity risks. All five framework antibodies were confirmed to specifically and selectively bind MCT1. The described framework engineering (i.e. humanization) process through interrogation of a comprehensive combinatorial library of a representative subset of fully human VH and VL germline sequences having/displaying the parent rodent antibody CDRs to identify productive solutions (or framework replacements) was a critical step in improving the developability of the antibody. All final five selected framework antibodies, each having specific VH/VL combinations of fully human germline frameworks displaying the M1056-derived CDRs, showed significantly improved properties relevant to clinical development, such as process development and immunogenicity.

In addition, a Tryptophan mutation introduced into HCDR3 of INX444 was removed in the humanization process of reverting all 6 CDRs back to the parent CDR sequences, providing significant improvement in oxidation.

Antibody CDR engineering: Humanized Framework antibody Ab1 was selected for further engineering. A site-saturated mutagenesis approach was used to generate a comprehensive library containing all possible natural amino acid substitutions (excluding Cysteine) at every VH and VL CDR amino acid residue of the humanized Framework antibody Ab1. 1444 resulting CDR antibody variants of Ab1 were screened for MCT1 cell binding using a high throughput flow cytometry assay and putative hits were scaled up and confirmed for binding and functional activity. This initial mutagenesis effort revealed, in some cases, a discrepancy in binding and functional activity readouts (for example, certain mutations causing apparent improvements in binding did not translate into improved inhibitory activity, or, in certain cases, even reduced functional activity) suggesting a disconnect in the mechanistic structure-activity requirements for transporter binding and functional transport inhibition of the antibody. Improvements in binding and potency for selected mutations were moderate and a second round of site-saturated mutagenesis was conducted. A critical amino acid change discovered in the initial CDR library screen (HC CDR1 F27R) was determined to improve binding affinity and functional activity (e.g., inhibition of metabolite transport and CD4/CD8 T cell proliferation), was embedded in a new saturated mutagenesis library and, to address the observed differences in structural requirements for binding and inhibition, the screening strategy was modified to integrate parallel high throughput analysis of all new 1444 antibody variants for cell-based binding as well as MCT mediated transport inhibition using a high throughput Bromopyruvate (BP) in vitro transport assay. CDR mutations that significantly improved binding and/or functional activity such as in BP transport and T cell inhibition assays were identified (some as shown in Table 3). The best single amino acid changes were combined in rationally designed combinatorial libraries and the resulting antibodies were screened for functional activity (BP transport and T cell inhibition). A panel of 16 hits (as shown in Tables 1, 2 and 3) referred to as Ab6 to Ab21, from the combinatorial library demonstrating most improved potencies were assessed for developability and immunogenicity to determine high potency therapeutic antibodies with developability and immunogenicity properties enabling clinical development.

Antibody constant region engineering: The human IgG1 effector null backbone with amino acid substitutions at L234A, L235E, G237A, A330S, and P331S show reduced binding to FcγR and C1q receptors (all amino acid residues are numbered according to the EU Index numbering), referred to as IgG1EN was selected for the exemplified anti-human MCT1 antibodies. The INX444 as described in WO19136300, has an Fc region having an alanine at residue 234, an alanine at residue 235, an arginine at residue 269, and an alanine at residue 322, herein referred to as INX444 LALA, was converted to an IgG1EN backbone (referred to as INX444 IgG1EN). No significant differences in effector function activity, developability profiles, or immunogenicity profile were observed with the 2 different backbones on the INX444 i.e., INX444 LALA and INX444 IgG1EN.

TABLE 1

CDR amino acid sequences of exemplified anti-human MCT1 antibodies

| Anti-human MCT1 Antibody | CDR Sequence | | | | | |
|---|---|---|---|---|---|---|
| | HCDR1 | HCDR2 | HCDR3 | LCDR1 | LCDR2 | LCDR3 |
| Ab1, Ab2, Ab3, Ab4, Ab5 | SEQ ID NO: 1 | SEQ ID NO: 2 | SEQ ID NO: 3 | SEQ ID NO: 4 | SEQ ID NO: 5 | SEQ ID NO: 6 |
| Ab6 | SEQ ID NO: 30 | SEQ ID NO: 31 | SEQ ID NO: 32 | SEQ ID NO: 33 | SEQ ID NO: 5 | SEQ ID NO: 6 |
| Ab7 | SEQ ID NO: 40 | SEQ ID NO: 2 | SEQ ID NO: 32 | SEQ ID NO: 33 | SEQ ID NO: 5 | SEQ ID NO: 6 |
| Ab8 | SEQ ID NO: 30 | SEQ ID NO: 44 | SEQ ID NO: 32 | SEQ ID NO: 33 | SEQ ID NO: 5 | SEQ ID NO: 6 |
| Ab9 | SEQ ID NO: 48 | SEQ ID NO: 2 | SEQ ID NO: 32 | SEQ ID NO: 33 | SEQ ID NO: 5 | SEQ ID NO: 6 |
| Ab10 | SEQ ID NO: 52 | SEQ ID NO: 2 | SEQ ID NO: 32 | SEQ ID NO: 33 | SEQ ID NO: 5 | SEQ ID NO: 6 |
| Ab11 | SEQ ID NO: 30 | SEQ ID NO: 2 | SEQ ID NO: 56 | SEQ ID NO: 33 | SEQ ID NO: 5 | SEQ ID NO: 6 |
| Ab12 | SEQ ID NO: 60 | SEQ ID NO: 2 | SEQ ID NO: 32 | SEQ ID NO: 33 | SEQ ID NO: 5 | SEQ ID NO: 6 |
| Ab13 | SEQ ID NO: 30 | SEQ ID NO: 2 | SEQ ID NO: 64 | SEQ ID NO: 33 | SEQ ID NO: 5 | SEQ ID NO: 6 |
| Ab14 | SEQ ID NO: 30 | SEQ ID NO: 2 | SEQ ID NO: 68 | SEQ ID NO: 33 | SEQ ID NO: 5 | SEQ ID NO: 6 |
| Ab15 | SEQ ID NO: 30 | SEQ ID NO: 2 | SEQ ID NO: 72 | SEQ ID NO: 33 | SEQ ID NO: 5 | SEQ ID NO: 6 |
| Ab16 | SEQ ID NO: 76 | SEQ ID NO: 2 | SEQ ID NO: 32 | SEQ ID NO: 33 | SEQ ID NO: 5 | SEQ ID NO: 6 |
| Ab17 | SEQ ID NO: 80 | SEQ ID NO: 2 | SEQ ID NO: 32 | SEQ ID NO: 33 | SEQ ID NO: 5 | SEQ ID NO: 6 |

TABLE 1-continued

CDR amino acid sequences of exemplified anti-human MCT1 antibodies

| Anti-human MCT1 Antibody | CDR Sequence | | | | | |
|---|---|---|---|---|---|---|
| | HCDR1 | HCDR2 | HCDR3 | LCDR1 | LCDR2 | LCDR3 |
| Ab18 | SEQ ID NO: 84 | SEQ ID NO: 2 | SEQ ID NO: 32 | SEQ ID NO: 33 | SEQ ID NO: 5 | SEQ ID NO: 6 |
| Ab19 | SEQ ID NO: 30 | SEQ ID NO: 88 | SEQ ID NO: 32 | SEQ ID NO: 33 | SEQ ID NO: 5 | SEQ ID NO: 6 |
| Ab20 | SEQ ID NO: 30 | SEQ ID NO: 2 | SEQ ID NO: 72 | SEQ ID NO: 4 | SEQ ID NO: 5 | SEQ ID NO: 6 |
| Ab21 | SEQ ID NO: 30 | SEQ ID NO: 2 | SEQ ID NO: 68 | SEQ ID NO: 4 | SEQ ID NO: 5 | SEQ ID NO: 6 |

TABLE 2

Amino Acid sequences of exemplified anti-human MCT1 antibodies

| Anti-human MCT1 Antibody | VH | VL | HC | LC |
|---|---|---|---|---|
| Ab1 | SEQ ID NO: 7 | SEQ ID NO: 8 | SEQ ID NO: 9 | SEQ ID NO: 10 |
| Ab2 | SEQ ID NO: 7 | SEQ ID NO: 13 | SEQ ID NO: 9 | SEQ ID NO: 15 |
| Ab3 | SEQ ID NO: 18 | SEQ ID NO: 13 | SEQ ID NO: 19 | SEQ ID NO: 15 |
| Ab4 | SEQ ID NO: 21 | SEQ ID NO: 22 | SEQ ID NO: 23 | SEQ ID NO: 24 |
| Ab5 | SEQ ID NO: 27 | SEQ ID NO: 22 | SEQ ID NO: 28 | SEQ ID NO: 24 |
| Ab6 | SEQ ID NO: 34 | SEQ ID NO: 35 | SEQ ID NO: 36 | SEQ ID NO: 37 |
| Ab7 | SEQ ID NO: 41 | SEQ ID NO: 35 | SEQ ID NO: 42 | SEQ ID NO: 37 |
| Ab8 | SEQ ID NO: 45 | SEQ ID NO: 35 | SEQ ID NO: 46 | SEQ ID NO: 37 |
| Ab9 | SEQ ID NO: 49 | SEQ ID NO: 35 | SEQ ID NO: 50 | SEQ ID NO: 37 |
| Ab10 | SEQ ID NO: 53 | SEQ ID NO: 35 | SEQ ID NO: 54 | SEQ ID NO: 37 |
| Ab11 | SEQ ID NO: 57 | SEQ ID NO: 35 | SEQ ID NO: 58 | SEQ ID NO: 37 |
| Ab12 | SEQ ID NO: 61 | SEQ ID NO: 35 | SEQ ID NO: 62 | SEQ ID NO: 37 |
| Ab13 | SEQ ID NO: 65 | SEQ ID NO: 35 | SEQ ID NO: 66 | SEQ ID NO: 37 |
| Ab14 | SEQ ID NO: 69 | SEQ ID NO: 35 | SEQ ID NO: 70 | SEQ ID NO: 37 |
| Ab15 | SEQ ID NO: 73 | SEQ ID NO: 35 | SEQ ID NO: 74 | SEQ ID NO: 37 |
| Ab16 | SEQ ID NO: 77 | SEQ ID NO: 35 | SEQ ID NO: 78 | SEQ ID NO: 37 |
| Ab17 | SEQ ID NO: 81 | SEQ ID NO: 35 | SEQ ID NO: 82 | SEQ ID NO: 37 |
| Ab18 | SEQ ID NO: 85 | SEQ ID NO: 35 | SEQ ID NO: 86 | SEQ ID NO: 37 |
| Ab19 | SEQ ID NO: 89 | SEQ ID NO: 35 | SEQ ID NO: 90 | SEQ ID NO: 37 |
| Ab20 | SEQ ID NO: 73 | SEQ ID NO: 8 | SEQ ID NO: 74 | SEQ ID NO: 10 |
| Ab21 | SEQ ID NO: 69 | SEQ ID NO: 8 | SEQ ID NO: 70 | SEQ ID NO: 10 |

TABLE 3

Exemplified anti-human MCT1 antibodies generated from combinatorial engineering of Ab1 (showing CDR differences compared to Ab1)

| Anti-human MCT1 antibody | HCDR and LCDR amino acid differences compared to Ab1 | |
|---|---|---|
| | HCDR | LCDR |
| Ab6 | F27R (HCDR1) + E62R (HCDR2) + S99R (HCDR3) | N30E (LCDR1) |
| Ab7 | F27R (HCDR1) + L29R (HCDR1) + S99R (HCDR3) | N30E (LCDR1) |
| Ab8 | F27R (HCDR1) + E58I (HCDR2) + S99R (HCDR3) | N30E (LCDR1) |
| Ab9 | F27R (HCDR1) + L34I (HCDR1) + S99R (HCDR3) | N30E (LCDR1) |
| Ab10 | F27R (HCDR1)+ N31G (HCDR1) + S99R (HCDR3) | N30E (LCDR1) |
| Ab11 | F27R (HCDR1) + S99R (HCDR3) + Y101H (HCDR3) | N30E (LCDR1) |
| Ab12 | F27R (HCDR1) + Q35V (HCDR1) + S99R (HCDR3) | N30E (LCDR1) |
| Ab13 | F27R (HCDR1) + S99R (HCDR3) + Y101R (HCDR3) | N30E (LCDR1) |
| Ab14 | F27R (HCDR1) + S99R (HCDR3) + A115P (HCDR3) | N30E (LCDR1) |
| Ab15 | F27R (HCDR1) + S99L (HCDR3) | N30E (LCDR1) |
| Ab16 | V24R (HCDR1) + F27R (HCDR1) + S99R (HCDR3) | N30E (LCDR1) |
| Ab17 | F27R (HCDR1) + Y32I (HCDR1) + S99R (HCDR3) | N30E (LCDR1) |
| Ab18 | F27R (HCDR1) + Q35G (HCDR1) + S99R (HCDR3) | N30E (LCDR1) |
| Ab19 | F27R (HCDR1) + S53R (HCDR2) + S99R (HCDR3) | N30E (LCDR1) |
| Ab20 | F27R (HCDR1) + S99L (HCDR3) | no differences |
| Ab21 | F27R (HCDR1) + S99R (HCDR3) + A115P (HCDR3) | no differences |

Example 2: Binding Affinity of the Anti-Human MCT1 Antibodies

Binding affinity for antibody screening at 25° C.: The exemplified anti-human MCT1 antibodies were screened for binding to human MCT1 using a competition Meso Scale Discovery (MSD) binding assay. Briefly, four constant concentrations of each antibody were mixed with a 2 or 3-fold dilution series of HEK WT cells (verified to express MCT1 $1.09 \times 10^6$ receptors/cell) to give a final concentration of: 250, 125, 62.5 and 31.25 µM (n=1) for each antibody and a cell gradient from 60 to 0.0585 million cells per mL. The mix was incubated at 37° C. for 1-2 days. After incubation, the incubated samples were spun down for 5 min at 500×g to remove cells. A 96-well multi-array plate (Meso Scale Diagnostics, Cat. #L15XA-3) was coated at 4° C. overnight with 1 µg/mL of goat anti human FC in phosphate buffered saline (PBS). Following coating, plates were washed 3 times with 150 µL PBST (PBS with 0.05% Tween 20) and blocked with 150 µL/well of PBS 3% blocker A buffer (Cat #R93BA-1) at 25° C. for 1 hr. Plates were then washed 3 times with PBST. 50 µL of the preincubated antibody: cell dilution series was transferred to the wells and incubated at 25° C. with 700 rpm shaking for 1 hr. Plates were washed 3 times with PBST. Then 100 µL of 1 µg/mL anti-human kappa-biotin antibody (Cat. #2060-08) was added, and plates were incubated at 25° C. with 700 rpm shaking for hr. Plates were washed 3 times with PBST, followed by addition of 100 µL of 1 µg/mL MSD Sulfo-tag streptavidin antibody (Meso Scale Diagnostics Cat. #R32 AD1), and plates were incubated at 25° C. with 700 rpm shaking for 1 hr. Plates were washed 3 times with PBST, 150 μL/well of 1× Read Buffer T was added to the wells and analyzed on a SECTOR® Imager 6000 (Meso Scale Diagnostics) 15 min after buffer addition. The apparent KD is determined by fitting a sigmoidal curve to the electrochemiluminescence (ECL) response vs. log (MCT1 receptor concentration) using assay development tool kit graphed with normalized ECL values.

The representative results as demonstrated in Table 4a show the anti-human MCT1 antibodies had desirable binding affinities to human MCT1.

Binding affinity of Ab and Ab6 at 37° C.: The binding affinity of the exemplified anti-human MCT1 antibodies Ab1 and Ab6 to human MCT1 was measured using a competition Meso Scale Discovery (MSD) binding assay. Briefly, two constant concentrations of each antibody was mixed with a dilution series of HEK WT cells (verified to express MCT1 $1.09 \times 10^6$ receptors/cell) to give a final concentration of: 50 μM and 5 μM in triplicate for each antibody and a 3 fold cell gradient from 29 to 0.0044 million cells per mL. The mix was incubated at 37° C. for 36-48 hr with shaking at 300 rpm. After incubation, the incubated samples were spun down for 8 min at 500×g to remove cells. A 96-well multi-array plate (Meso Scale Diagnostics, Cat. #L15XA-3) was coated at 4° C. overnight with 3 μg/mL of goat anti human FC in phosphate buffered saline (PBS). Following coating, plates were washed 3 times with 150 μL PBST (PBS with 0.05% Tween 20) and blocked with 150 μL/well of PBS 3% blocker A buffer (Meso Scale Diagnostics, Cat. #R93BA-1) at 37° C. for 30 min. Plates were then washed 3 times with PBST. 50 μL of the preincubated antibody: cell dilution series was transferred to the wells and incubated at 37° C. with 1000 rpm shaking for 1 hr. Plates were washed 3 times with PBST. Then 100 μL of 1 μg/mL anti-human kappa-biotin antibody (Southern Biotech, Cat. #2060-08) was added, and plates were incubated at 37° C. with 1000 rpm shaking for 30 min. Plates were washed 3 times with PBST, followed by addition of 100 μL of 1 μg/mL MSD Sulfo-tag streptavidin antibody (Meso Scale Diagnostics Cat. #R32AD-1), and plates were incubated at 37° C. with 1000 rpm shaking for 15 min. Plates were washed 3 times with PBST, 150 L/well of 1× Read Buffer T (Meso Scale Diagnostics Cat. #R92TC-1) was added to the wells and analyzed on a SECTOR® Imager 6000 (Meso Scale Diagnostics) 15 min after buffer addition. The apparent $K_D$ is determined by fitting a sigmoidal curve to the electrochemiluminescence (ECL) response vs. log (MCT1 receptor concentration) using Assay development tool kit graphed with normalized ECL values. Each experiment was performed in triplicate as separate independent dilution series and plates. The data reported was the average $K_D$.

The results as demonstrated in Table 4b, show the anti-human MCT1 Ab1 and Ab6 had desirable binding affinities to human MCT1.

TABLE 4a

Binding affinity screening of exemplified anti-human MCT1 antibodies to MCT1 at 25° C.

| MCT1 Antibody | KD value (nM) |
| --- | --- |
| Ab1 | 5.81 |
| Ab6 | 1.27 |
| Ab7 | 0.47 |
| Ab8 | 0.55 |
| Ab9 | 4.56 |
| Ab10 | 0.85 |
| Ab11 | 1.91 |

TABLE 4a-continued

Binding affinity screening of exemplified anti-human MCT1 antibodies to MCT1 at 25° C.

| MCT1 Antibody | KD value (nM) |
| --- | --- |
| Ab12 | 1.64 |
| Ab13 | 2.82 |
| Ab14 | 1.31 |
| Ab15 | 1.96 |
| Ab16 | 0.71 |
| Ab17 | 1.04 |
| Ab18 | 5.14 |
| Ab19 | 0.46 |
| Ab20 | 0.64 |
| Ab21 | 0.85 |

TABLE 4b

Binding affinity of exemplified anti-human MCT1 antibodies Ab1 and Ab6 to human MCT1 at 37° C.

| MCT1 Antibody | $K_D$ value (nM) |
| --- | --- |
| Ab1 | 1.23 |
| Ab6 | 0.59 |

Example 3: Functional Characterization of the Anti-Human MCT1 Antibodies

Inhibition of MCT1 mediated transport: An in vitro bromopyruvate functional transport assay was used to assess ability of the exemplified anti-human MCT1 antibodies to inhibit MCT1 mediated transport activity. HEK293T cells expressing MCT1 were pre-treated with exemplified anti-human MCT1 antibodies or a small molecule MCT1 inhibitor at 37° C. for 1 h. Cells were then incubated with a cytotoxic reagent 3-bromopyruvate (3-BrPy) at concentrations ranging from 25 to 500 mM for 2 to 6 h. ATP from dying cells was quantified using a commercial viability kit (ATPlite, PerkinElmer) in a 96-well plate and viability measured using luminescence. Reduction of ATP production indicated functional activity of the antibody. The mouse or chimeric antibody before humanization was used as a positive control antibody. MCT1/CD147 double knockout 293T cells were used as a negative control cell line.

The results as demonstrated in Table 5, show that the exemplified anti-human MCT1 antibodies inhibit MCT1 receptor mediated transport in the bromopyruvate assay, and can thus also be identified as antagonistic anti-human MCT1 antibodies.

TABLE 5

Inhibition of MCT1 mediated transport by exemplified anti-human MCT1 antibodies.

| MCT1 Antibody | $IC_{50}$ value [nM] |
| --- | --- |
| Ab1 | 164 |
| Ab6 | 25 |
| Ab7 | 28 |
| Ab8 | 21 |
| Ab9 | 35 |
| Ab10 | 39 |
| Ab11 | 35 |
| Ab12 | 39 |
| Ab13 | 42 |
| Ab14 | 40 |
| Ab15 | 48 |

TABLE 5-continued

Inhibition of MCT1 mediated transport by exemplified anti-human MCT1 antibodies.

| MCT1 Antibody | IC$_{50}$ value [nM] |
|---|---|
| Ab16 | 31 |
| Ab17 | 38 |
| Ab18 | 41 |
| Ab19 | 35 |
| Ab20 | 83 |
| Ab21 | 50 |

Inhibition of CD4/CD8 T-cell Proliferation: Inhibition of T cell proliferation by the exemplified anti-human MCT1 antibodies was assessed in primary T cells isolated from human PBMCs. Human PBMCs were isolated from human blood samples by standard Ficoll-Paque™ plus (GE HEALTHCARE) density gradient centrifugation methods, and primary T cells were isolated from the PBMC suspension by negative selection with EasySep™ Human T cell Enrichment kit according to the manufacturer's protocol (STEMCELL™ Technologies). Isolated human primary T cells were labeled with Cell Trace Violet dye (Thermo Fisher) and resuspended at 1×10$^6$ cells/ml, and plated in polystyrene 96-well, u-bottom plates in complete medium (RPMI-1640 containing 10% Fetal bovine serum, 1×MEM-nonessential amino acids, 1 mM sodium pyruvate, 1× penicillin-streptomycin solution (all from Corning®) and 1× GlutaMAX™ Gibco™), 0.1% β-mercaptoethanol (LIFE TECHNOLOGIES). Anti-human MCT1 antibodies or isotype control antibodies were added at 300 µg/mL diluted 4-fold and 11-point titration. Cells were stimulated with Human CD3/CD28 dynabeads (GIBCO) for 3 days at 37° C. and 5% CO$_2$. T cell proliferation was analyzed by FACS as a dilution of cell trace violet dye.

The results showed that the exemplified anti-human MCT1 antibodies inhibited CD4 and CD8 T cell proliferation in a dose dependent manner. Table 6 shows the IC$_{50}$ values of the CD4 and CD8 T cell proliferation inhibition by the exemplified anti-human MCT1 antibodies.

TABLE 6

Inhibition of T cell proliferation by exemplified anti-human MCT1 antibodies

| MCT1 Antibody | CD4 T cells IC$_{50}$ [nM] | CD8 T cells IC$_{50}$ [nM] |
|---|---|---|
| Ab1 | 59 | 42 |
| Ab6 | 3 | 3 |
| Ab7 | 2 | 4 |
| Ab8 | 3 | 3 |
| Ab9 | 4 | 5 |
| Ab10 | 3 | 7 |
| Ab11 | 4 | 5 |
| Ab12 | 4 | 5 |
| Ab13 | 3 | 4 |
| Ab14 | 5 | 6 |
| Ab15 | 5 | 8 |
| Ab16 | 5 | 3 |
| Ab17 | 5 | 2 |
| Ab18 | 6 | 2 |
| Ab19 | 5 | 3 |
| Ab20 | 13 | 6 |
| Ab21 | 6 | 4 |

In vitro T regulatory cell differentiation: Enhancement of the expansion of induced Regulatory T (Treg) cells by exemplified anti-human MCT1 antibodies was assessed in primary naive CD4 T cells isolated from PBMCs. Human PBMCs were isolated from human blood samples by standard Ficoll-Paque™ plus (GE HEALTHCARE) density gradient centrifugation methods, and primary naïve CD4 T cells were isolated from the PBMC suspension by negative selection according to the manufacturer's protocol (StemCell). Isolated human primary naive CD4 T cells were resuspended at 1×10$^6$ cells/mL and plated in polystyrene 96-well, u-bottom plates in complete medium (RPMI-1640 containing 10% Fetal bovine serum, 1×MEM-nonessential amino acids, 1 mM sodium pyruvate, 1× penicillin-streptomycin solution (all from Corning®) and 1× GlutaMAX™ (Gibco™), 0.1% β-mercaptoethanol (LIFE TECHNOLOGIES). Exemplified anti-human MCT1 antibodies or isotype control antibodies were added at different concentrations. Cells were stimulated with anti-CD3/CD28 dymane beads (Gibco) and hrTGFb (R&D) and hrIL-2 (R&D) for 3 days at 37° C. and 5% CO$_2$. Treg differentiation is analyzed by FACS as % of FoxP3+/CD25+ cells.

The results as demonstrated in FIG. 1 and Tables 7 and 8 show that the anti-human MCT1 antibodies Ab1 and Ab6 increased regulatory T cell differentiation in a concentration dependent manner as compared to the isotype control. These results showed an unexpected benefit of the anti-human MCT1 antibodies, suggesting that treatment with Ab1 or Ab6 may enhance differentiation of regulatory T cells which subsequently inhibit autoimmune responses.

TABLE 7

Percent increase in regulatory T cell differentiation upon treatment upon treatment with anti-human MCT1 antibody Ab1 over isotype control

| Concentration (nM) | % Treg cell increase with Ab1 treatment over isotype control |
|---|---|
| 2000 | 16.5 (+/−6.8) |
| 400 | 17.3(+/−5.8) |
| 80 | 12.4 (+/−7.2) |
| 16 | 2.4 (+/−1.6) |
| 3.2 | 0 |
| 0.64 | −1.4 (+/−3.0) |
| 0.128 | −0.8 (+/−0.2) |

TABLE 8

Percent increase in regulatory T cell differentiation upon treatment with anti-human MCT1 antibody Ab6 or isotype control

| Concentration (µg/mL) | % Treg cell increase with Ab6 treatment | % Treg cell increase with isotype control treatment |
|---|---|---|
| 300 | 14.39 | 0.07 |
| 60 | 10.81 | 3.09 |
| 12 | 8.78 | 4.99 |
| 2.4 | 2.95 | 0.63 |
| 0.48 | −5.82 | 2.24 |
| 0.096 | −3.16 | 3.37 |
| 0.0192 | 1.05 | 2.10 |

B cell proliferation: Inhibition of B cell proliferation by the exemplified anti-human MCT1 antibodies was assessed in primary B cells isolated from human PBMCs. Human PBMCs were isolated from human blood samples by standard Ficoll-Paque™ plus (GE HEALTHCARE) density gradient centrifugation methods, and primary B cells were isolated from the PBMC suspension by positive selection with CD19 microbeads according to the manufacturer's protocol (Miltenyi Biotec). Isolated human primary B cells were labeled with Cell Trace Violet dye (Thermo Fisher) and resuspended at 1×10$^6$ cells/mL and plated in polystyrene 96-well, u-bottom plates in complete medium (RPMI-1640 containing 10% Fetal bovine serum, 1×MEM-nonessential amino acids, 1 mM sodium pyruvate, 1× penicillin-streptomycin solution (all from Corning®) and 1× GlutaMAX™ (Gibco™), 0.1% β-mercaptoethanol (LIFE TECHNOLOGIES). Exemplified anti-human MCT1 antibodies or isotype control antibodies were added at 300 μg/mL diluted 4-fold and 11-point titration. Cells were stimulated with Human MEGACD40L protein (ENZO) and rhIL-4 (R&D) for 5 days at 37° C. and 5% $CO_2$. B cell proliferation is analyzed by FACS as a dilution of cell trace violet dye.

The results showed that the exemplified anti-human MCT1 antibody Ab6 inhibited B cell proliferation in a dose dependent manner, with an average $IC_{50}$ of 2.95 nM from 3 donors as shown in Table 9.

TABLE 9

Inhibition of B cell proliferation by exemplified anti-human MCT1 antibody Ab6

|  | Donor1 | Donor2 | Donor3 | Average |
|---|---|---|---|---|
| IC50 (nM) | 3.06 | 2.40 | 3.38 | 2.95 |

Example 4: Fcv Receptor Binding and Effector Function Activity of the Anti-Human MCT1 Antibodies In vitro Human Fcγ receptor (FcγR) binding and effector function activity was conducted to confirm that the anti-human MCT1 antibodies lack detectable FcγR binding, complement-dependent cytotoxicity (CDC), antibody-dependent cellular cytotoxicity (ADCC), and antibody-dependent cellular phagocytosis (ADCP) activity.

Human Fcγ receptor binding. Biacore T100 (Cytiva), Biacore reagents, and Scrubber2 Biacore Evaluation Software (Biologics 2008) were used for the SPR binding analysis of the MCT1 antibodies. Further, the IgGEN and LALA IgG backbones were also compared for binding to Fcγ Receptors. A series S CM5 chip (Cytiva P/N BR100530) was prepared using the manufacturer's EDC/NHS amine coupling method (Cytiva P/N BR100050). Briefly, the surfaces of all 4 flow cells (FC) were activated by injecting a 1:1 mixture of EDC/NHS for 7 minutes at 10 μL/minute. Protein A (Calbiochem P/N 539202) was diluted to 100 μg/mL in 10 mM acetate, pH 4.5 buffer, and immobilized for approximately 4000 RU onto all 4 FCs by 7 minute injection at a flow rate of 10 μL/minute. Unreacted sites were blocked with a 7 minute injection of ethanolamine at 10 μL/minute. Injections of 2×10 μL of glycine, pH 1.5, were used to remove any noncovalently associated protein. Running buffer was 1×HBS-EP+ (TEKNOVA, P/N H8022). The FcγR extracellular domains (ECDs)-FcγRI (CD64), FcγRIIA_131R, and Fc-RIIA_131H (CD32a), Fc-RIIIA_158V, FcγRIIIA_158F (CD16a), and Fc-RIIb (CD32b) were produced from stable CHO cell expression. All FcγR ECDs were purified using IgG Sepharose and size exclusion chromatography (SEC). For FcγRI binding, antibodies were diluted to 2.5 μg/mL in running buffer, and approximately 150 RU of each antibody was captured in FCs 2 through 4 (RU captured). FC1 was the reference FC, therefore no antibody was captured in FC1. FcγRI ECD was diluted to 200 nM in running buffer and then two-fold serially diluted in running buffer to 0.78 nM. At least duplicate injections of each concentration were injected over all FCs at 40 μL/minute for 120 seconds followed by a 1200 second dissociation phase. Regeneration was performed by injecting 15 μL of 10 mM glycine, pH 1.5, at 30 μL/minute over all FCs. Reference-subtracted data was collected as FC2FC1, FC3-FC1, and FC4-FC1. The measurements were obtained at 25° C. The affinity ($K_D$) was calculated using either steady state equilibrium analysis with the Scrubber 2 Biacore Evaluation Software or a "1:1 (Langmuir) binding" model in BIA Evaluation. For FcγRIIa, FcγRIIb, and FcγRIIIa binding, antibodies were diluted to 5 μg/mL in running buffer, and approximately 500 RU of each antibody was captured in FCs 2 through 4 (RUcaptured). FC1 was again the reference FC. Fcγ receptor ECDs were diluted to 10 μM in running buffer and then 2-fold serially diluted in running buffer to 39 nM. Duplicate injections of each concentration were injected over all FCs at 40 μL/minute for 60 seconds followed by a 120 second dissociation phase. Regeneration was performed by injecting 15 μL of 10 mM glycine, pH 1.5, at 30 μL/minutes over all FCs. Reference-subtracted data was collected as FC2-FC1, FC3-FC1, and FC4-FC1. The measurements were obtained at 25° C. The affinity ($K_D$) was calculated using the steady state equilibrium analysis with the Scrubber 2 Biacore Evaluation Software.

The results as demonstrated in Table 10, show that the IgG1EN Fc and LALA Fc backbones do not bind the Fcγ receptors.

TABLE 10

Binding affinities of anti-human MCT1 antibodies to Human Fcγ Receptors

| Human FcγR receptors | Human WT IgG1 Fc $K_D$ ± SD | INX444 IgG1EN $K_D$ | INX444 LALA $K_D$ |
|---|---|---|---|
| FcγRI | 42.6 ± 3.5 pM | No binding | >200 nM |
| FcγRIIA_131H | 0.5 ± 0.0 uM | >10 uM | >10 uM |
| FcγRIIA_131R | 0.5 ± 0.0 uM | >10 uM | >10 uM |
| FcγRIIb | 1.9 ± 0.0 uM | >10 uM | >10 uM |
| FcγRIIIA_V158 | 0.1 ± 0.0 uM | >10 uM | >10 uM |
| FcγRIIIA_F158 | 0.9 ± 0.0 uM | >10 uM | >10 uM |

C1q binding. A 96-well microplate was coated with 100 μL/well of each antibody diluted in DPBS (Dulbecco's HyClone) with a concentration range of 10 μg/mL to 0.19 μg/mL. Testing was performed in duplicate wells. The plate was sealed and incubated overnight at 4° C. The coating reagent was removed, and 200 μL/well of casein blocking reagent (Thermo) was added. The plate was sealed and incubated for 2 hours at room temperature (RT). Plate was washed 3 times with wash buffer (1×TBE with 0.05% Tween 20) and 100 μL/well of Human C1q (MS Biomedical) at 10 μg/mL diluted in casein blocking reagent was added and incubated for 3 hours at RT. The plate was then washed three times with wash buffer and 100 μL/well of a 1:800 times dilution of Sheep anti-human C1q-HRP (Abcam #ab46191) in casein blocker was added and incubated for 1 hour at RT. The plate was washed 6 times with wash buffer, and 100 μL/well of TMB Substrate (Pierce) was added to each well and incubated for 7 minutes. 100 μL of 1 N HCl was added to each well to stop the reaction. Optical density was immediately measured using a colorimetric microplate reader set to 450 nm. The data was analyzed using SoftMax Pro 7.1 Data Acquisition and Analysis Software.

The results (not shown) showed that the exemplified anti-human MCT1 antibody Ab6 and IgG1EN control did not bind the complement component C1q when compared to the human IgG1 positive control antibody which bound in a dose dependent manner.

In vitro ADCC, ADCP, and CDC activity. Raji cells expressing MCT1 and CD20 were used as target cells for the 3 assays. For the ADCC assay, Jurkat FcγRIIIa (V158)-NFAT-Luc cell line stably co-expressing human FcγRIIIa (V158), human FcεRγ-chain and NFAT luciferase reporter gene (Eli Lilly and Company) was used as the effector cell line. For the ADCP assay, Jurkat FcγRIIa-NFAT-Luc cell line stably co-expressing human FcγRIIa (H131) and NFAT luciferase reporter gene (G988A, Promega) was used as the effector cell line. Briefly, test samples were serially diluted 4-fold in duplicates and 50 μL/well of the diluted test compound or assay buffer was added to 96-well plates (Costar 3917). Raji cells were diluted in assay medium to a final cell density of $1.0 \times 10^6$ cells/mL and a volume of 50 μL cells/well was added to the ADCC, ADCP and CDC assay plates which have 50 μL/well of the serially diluted test samples. ADCC, ADCP and CDC assay plates were gently agitation on a plate shaker for 30 seconds at 200 rpm, then incubated for 1 h at 37° C. The stably transfected Jurkat V158 cells or Jurkat H131 cells were diluted to a concentration of $3 \times 10^6$ cells/mL and 50 IL/well was added to the respective ADCC and ADCP assay plates containing the serially diluted test samples and Raji cells, and the plate was mixed by gentle agitation on a plate shaker for 30 seconds at 200 rpm, then incubated for 4 hrs at 37° C. Pre-diluted complement from human serum (Quidel A113) was added to the CDC plate (50 μL/well) containing the serially diluted test samples and Raji cells, and the plate was mixed by gentle agitation on a plate shaker for 30 seconds at 200 rpm, then incubated for 2 h at 37° C. After incubation, the ADCC, ADCP, and CDC plates were brought to room temperature for 10 minutes followed by addition of 100 μL of One-glo Ex (E8130, Promega) to the ADCC and ADCP assay plates and the Cell-Titer Glo (G7571, Promega) to the CDC assay plates. The luminescence was read using an Envision 11 multi-mode plate reader using 0.2 cps integration. The results were analyzed using Prism v8.2 (Graph pad).

In vitro neutrophil activation. Heparin-treated human whole blood obtained from three independent healthy donors was used. Blood was diluted at 1:1 with assay media and plated at 100 μL/well in 96-well plates. Test antibodies were titrated into the diluted whole blood starting at 300 μg/mL, following by 1:5 serial dilutions. R848 (TLR7 agonist) was used as a positive control, at a final concentration of 1 μg/mL. All conditions were performed in triplicate. Samples were incubated for 1 h or overnight, after that red blood cells were lysed using ACK buffer, cells were washed and stained with the cocktail of following antibodies: anti-CD3-BV785 (Cat #317330, Biolegend), anti-CD45-BV421 (Cat #563879, BD Bioscience), CD66b-FITC (Cat #555724, BD Bioscience), CD11b-PE-Cy7 (Cat #552850 BD Bioscience). Cells were stained for 30 min at RT, washed and acquired using Fortessa X-20, data was analyzed using FlowJo and plotted in Prism GraphPad. Neutrophils were identified based on their size and granularity and expression of following makers: CD45+/CD3−/CD66b+/CD11b+. Expression of CD66b and CD11b was analyzed as gMFI (geometric mean fluorescent intensity) of CD45+/CD3−/CD66b+/CD11b+ cells.

Figure 2A:
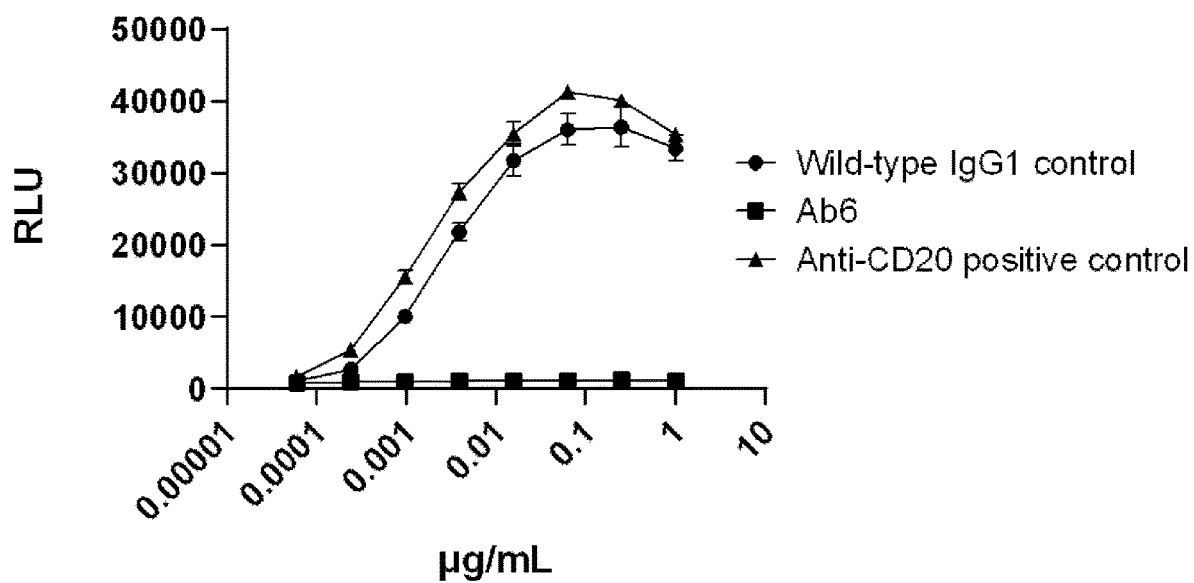
FIGS. 2A, 2B, and 2C shows anti-human MCT1 antibody Ab6 does not significantly elicit ADCC (2A) or ADCP (2B) Fc-mediated effector function activity, or CDC (2C) activity.
Figure 2B:
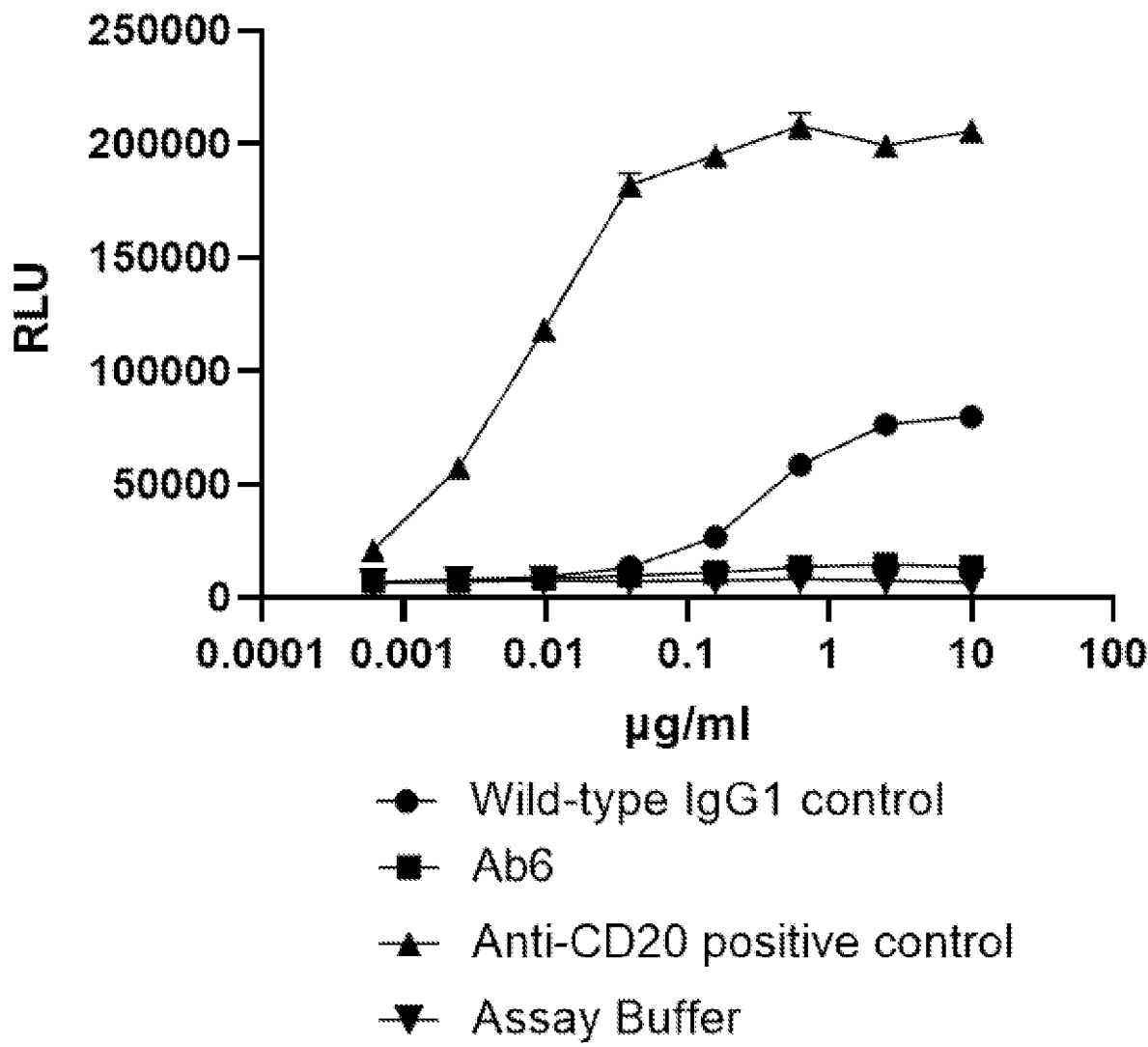
Figure 2C:
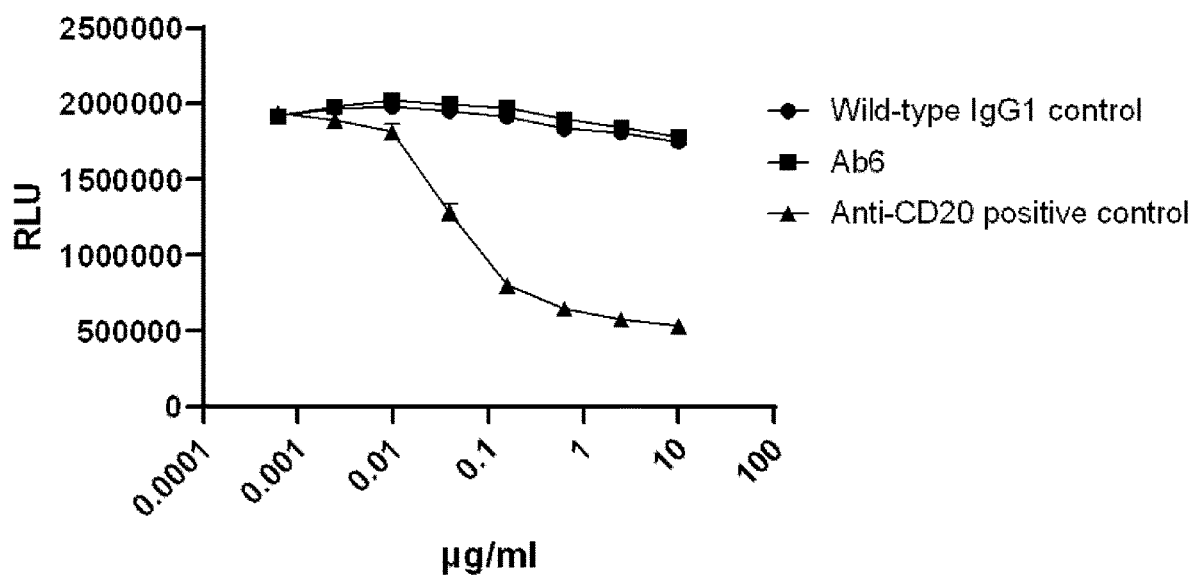

The results in FIG. 2A showed that the exemplified anti-human MCT1 antibody Ab6 did not elicit ADCC activity at all concentrations tested when compared to the positive control wild type IgG1 anti-human MCT1 antibody and a CD20 antibody which elicited ADCC activity in a dose dependent manner. The results in FIG. 2B showed that the exemplified anti-human MCT1 antibody Ab6 did not significantly elicit ADCP activity at all concentrations tested when compared to the positive control wild type IgG1 anti-human MCT1 antibody and a CD20 antibody which elicited ADCP activity in a dose dependent manner. The results for the neutrophil activation assay (not shown) confirmed a lack of FcγRIIa activation by the anti-human MCT1 antibody Ab6 at all timepoints and concentrations tested. These results cumulatively showed that Ab6 is unlikely to elicit Fc-mediated effector function activity in vivo. The results in FIG. 2C showed that neither the exemplified anti-human MCT1 antibody Ab6 or the wild-type IgG1 control antibody elicited CDC activity, when compared to an anti-CD20 positive control which elicited CDC activity in a dose dependent manner.

Example 5: Developability Properties of Anti-Human MCT1 Antibodies

Biophysical and chemical properties of the anti-human MCT1 antibodies were evaluated to determine the developability profile of the antibodies.

In culture oxidation and degradation: In-culture oxidation and degradation of the exemplified anti-human MCT1 antibodies was assessed. The exemplified anti-human MCT1 antibodies were expressed in CHO cells and subjected to the Protein A capture method which follows. The capture column (MabSelect™ SuRe™ Protein A) was neutralized by washing with 2 column volumes of 50 mM Tris pH 8.0, then equilibrated with 20 mM Tris pH 7.0. Cell-free bioreactor harvest containing the antibody was then loaded onto the column. Following sample load, the column was washed with 20 mM Tris pH 7.0, then two column volumes of 20 mM Tris pH 7.0+1M NaCl, then 20 mM Tris pH 7.0. MCT1 antibody was then eluted from the column using 20 mM acetatic acid+5 mM citric acid buffer (pH 2.9). Eluate fractions were collected by UV absorbance (>200 mAu) and pooled together. This pool was then adjusted to pH 5 with 1M Tris pH 8.0 and allowed to incubate at room temperature while stirring for 15 min. The elution then sat at room temp for a total of 1 hr. The sample pool was spun down at 20° C., 3000×g, for 5 minutes to remove host cell protein (HCP) precipitate. The sample supernatant was then filtered with a 0.22 micron steri-flip PDVF filter (Millipore) and then subjected to preparative SEC (see FIGS. 3A and 3B).

Figure 3A:
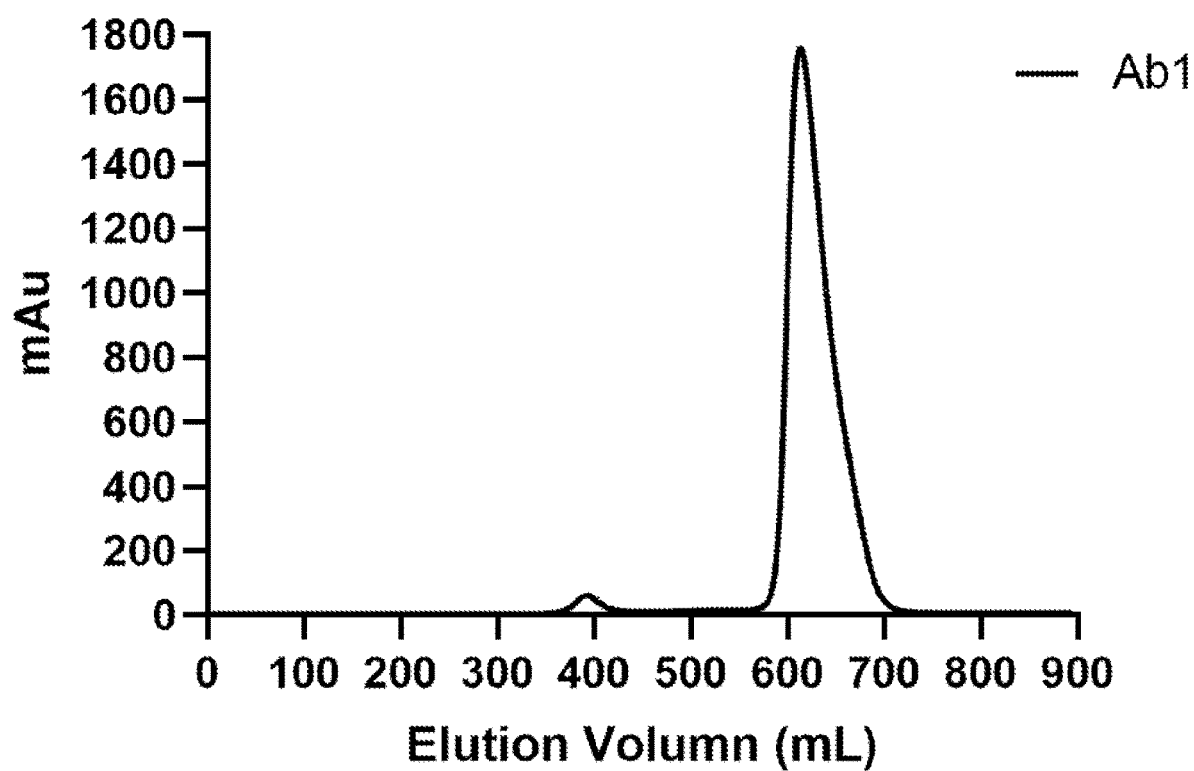
FIGS. 3A and 3B show the preparative size exclusion chromatography (SEC) chromatograms of anti-human MCT1 antibody Ab1 (3A) and INX444 antibodies (3B) after cell culture and affinity capture.
Figure 3B:
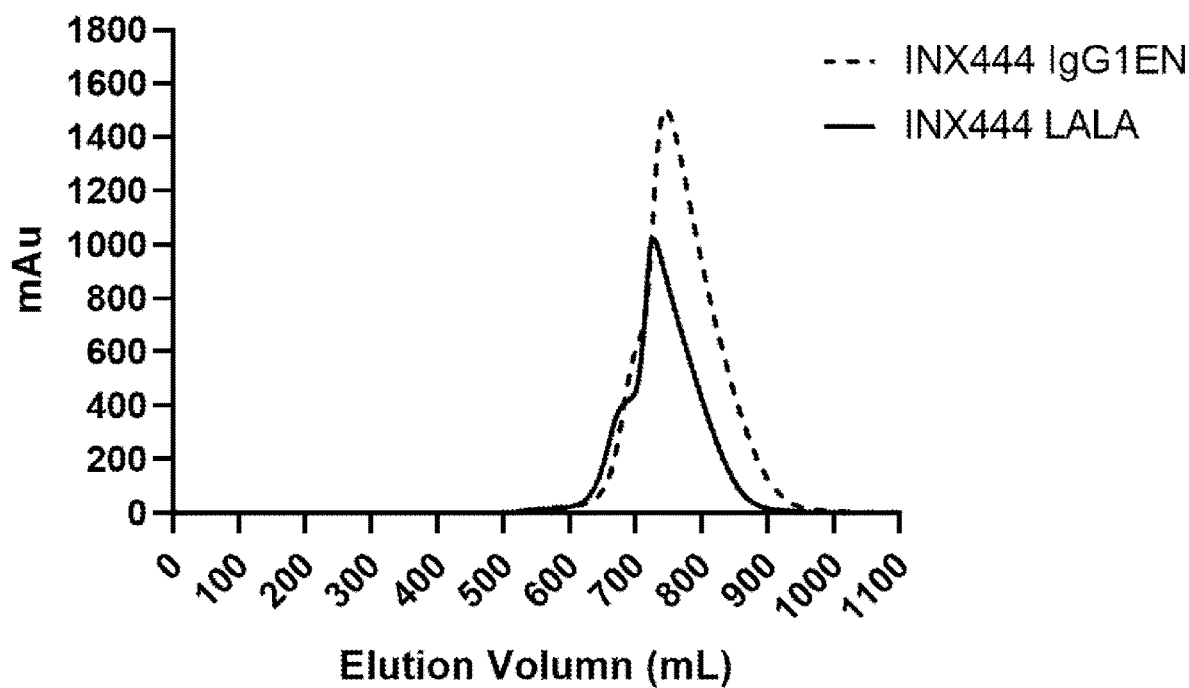

The results as demonstrated in FIGS. 3A and 3B, indicate that the exemplified anti-human MCT1 antibodies had desirable developability oxidation and degradation profile. Specifically, the SEC profile for Ab1 (FIG. 3A) showed a narrow single peak without any shoulder peaks, indicating reduced degradation (e.g., in-culture clipping), or oxidation of the antibody compared to INX444, providing desirable developability properties and reducing potentially complex and costly changes in downstream analytical and manufacturing processes (such as allowing for collection of high purity material by standard purification procedures). The SEC profile for INX444 antibodies (FIG. 3B) showed a front shoulder peak in the elution profile. Further analysis of the INX444 antibodies by LC/MS/MS identified the front shoulder peak as attributable to in-culture antibody clipping (CH1 multiple clipping sites) and oxidation (majority observed at amino acid residue W105). Application of standard platform purification procedures were not suitable for removing these impurities from the INX444 antibodies, and thus provided challenges to downstream purification processes and developability.

Interaction with analytical size exclusion column: 3 μg of the exemplified anti-human MCT1 antibodies (greater than 96% purity) were injected onto an analytical size exclusion column (TOSOH TSKgel-UP-SW3000, Fisher scientific, Cat. 50-104-9800) on an Agilent HPLC system with a mobile phase flow rate of 0.35 mL/min. The UV signals were detected at 214 nm.

Figure 4:
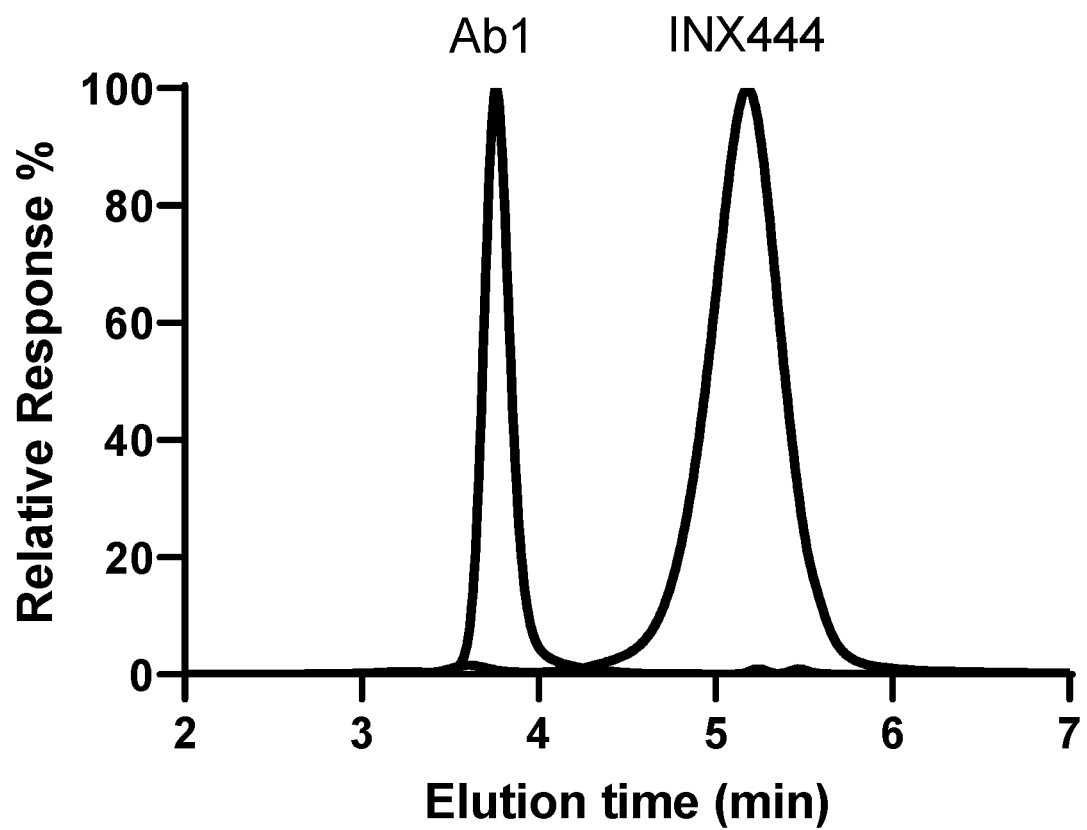
FIG. 4 shows an overlay of analytical SEC chromatograms comparing the retention times of anti-human MCT1 antibody Ab1 and INX444 IgG1EN.

The results as demonstrated in Table 11 and FIG. 4, show that the retention time of exemplified anti-human MCT1 antibodies on an analytical size exclusion column was significantly reduced (ranged from 3.78 to 4.04 minutes), when compared to INX444 (5.18 minutes). Specifically, these results indicated that there was reduced interaction between the column resins and the exemplified anti-human MCT1 antibodies, when compared to the INX444 antibody (this is also demonstrated by the peak widths of the Ab1 and INX444 in FIG. 4). Strong interactions of an antibody with column resins poses challenges in analytical method development to detect soluble high molecular weight species and requires modifications in downstream analytical processes.

TABLE 11

Size exclusion column retention times of exemplified anti-human MCT1 antibodies

| MCT1 Antibody | Retention Time [minutes] |
|---|---|
| Ab1 | 3.78 |
| Ab6 | 3.91 |
| Ab7 | 3.90 |
| Ab8 | 3.91 |
| Ab9 | 3.90 |
| Ab10 | 3.91 |
| Ab11 | 3.91 |
| Ab12 | 3.90 |
| Ab13 | 3.88 |
| Ab14 | 3.90 |
| Ab15 | 3.89 |
| Ab16 | 3.91 |
| Ab17 | 3.90 |
| Ab18 | 4.04 |
| Ab19 | 4.04 |
| Ab20 | 4.08 |
| Ab21 | 4.09 |
| INX444 IgG1EN | 5.18 |

Hydrophobic interaction chromatography (HIC): 20 μg of IgG samples (1 mg % mL) were diluted 1:1 with 2× Buffer A concentrate (2 M ammonium sulfate, 0.1 M sodium phosphate at pH 6.8) to achieve a final ammonium sulfate concentration of 1 M prior to analysis. A TSKgel butyl-NPR (4.6 mm ID×10 cm, 2.5 um, Tosoh #42168) column was used, with a 2-minute hold in mobile phase A (1M ammonium sulfate, 50 mM sodium phosphate. pH 6.8), followed by a linear gradient (0-100% B) of mobile phase A and mobile phase B (50 mM sodium phosphate. pH 6.8) over 23 minutes at a flow rate of 1 mL/minute. A final hold of 5 minutes in 100% mobile phase B was used to remove any remaining protein, with UV absorbance monitoring at 280 nm and 215 nm.

The results as demonstrated in Table 12, show that the exemplified anti-human MCT1 antibodies Ab6 to Ab21 had a lower retention times on a hydrophobic interaction column (ranged from 6.53 min to 8.46 min) indicating low hydrophobicity, when compared to INX444 which had a retention time of 12 min. Antibody hydrophobicity can create downstream manufacturing concerns such as poor expression and protein aggregation.

TABLE 12

Hydrophobic interaction chromatography data on exemplified anti-human MCT1 antibodies

| MCT1 Antibody | HIC RT [min] |
|---|---|
| Ab1 | 11.9 |
| Ab6 | 7.4 |
| Ab7 | 6.53 |
| Ab8 | 7.31 |
| Ab9 | 7.21 |
| Ab10 | 7.71 |
| Ab11 | 7.08 |
| Ab12 | 7.53 |
| Ab13 | 6.92 |
| Ab14 | 7.32 |
| Ab15 | 8 |
| Ab16 | 6.64 |
| Ab17 | 6.66 |
| Ab18 | 7.82 |
| Ab19 | 7.12 |
| Ab20 | 8.46 |
| Ab21 | 7.84 |
| INX444 IgG1EN | 12 |

Cross-interaction chromatography: The cross-interaction chromatography (CIC) IgG column was prepared by coupling ~30 mg of human serum polyclonal antibodies (I4506; Sigma) to a 1-mL HiTrap NHS-activated column (17-0716-01; GE Healthcare), followed by quenching with ethanolamine and Tris. The blank column (control column without the IgG) was prepared by deactivating with ethanolamine and Tris. 20 μg of each antibody was injected onto each column (IgG and Blank) with a constant flow rate of 0.2 mL/min using 10 mM sodium phosphate, 10 mM NaCl, pH 6.5 as the mobile phase on an Agilent 1260 series HPLC system. Retention times (RT) obtained by both IgG and blank columns were used to calculate K' (ratio of the retention time, calculated as IgG K'=[IgG column RT−blank column RT]/blank column RT). In addition, due to peak tailing in some samples, peak width at 50% height is also obtained to monitor "stickiness" of test antibodies.

The results as demonstrated in Table 13, show that the exemplified anti-human MCT1 antibodies did not exhibit significant nonspecific binding to serum IgG or the blank column as shown by the IgG column retention time (ranged from 5.07 to 5.41 min) and the blank peak width (ranged from 4.81 to 5.01 min) when compared to INX444 (IgG RT of 11 min, blank peak width of 6.81 min). Furthermore, the exemplified antibodies IgG peak width ranged from 1.36 to 1.94 min and the blank peak width ranged from 0.88 to 1.2 min, indicating low IgG and column resin interaction when compared to INX444 (IgG peak width of 8 min, blank peak width of 2 min). Low IgG retention times on a CIC column indicate potentially improved solubility of an antibody.

TABLE 13

CIC analysis of exemplified anti-human MCT1 antibodies

| MCT1 Antibody | IgG column RT [min] | Blank column RT [min] | IgG column peak width [min] | Blank column peak width [min] | IgG K' (column retention time ratio) |
|---|---|---|---|---|---|
| Ab1 | 5.07 | 4.81 | 1.5 | 1.2 | 0.05 |
| Ab6 | 5.31 | 4.97 | 1.45 | 1 | 0.07 |
| Ab7 | 5.38 | 5 | 1.79 | 0.88 | 0.08 |
| Ab8 | 5.34 | 4.98 | 1.55 | 1.02 | 0.07 |
| Ab9 | 5.28 | 4.94 | 1.46 | 1.08 | 0.07 |
| Ab10 | 5.27 | 4.96 | 1.44 | 1.08 | 0.06 |
| Ab11 | 5.33 | 5.01 | 1.57 | 0.91 | 0.06 |

TABLE 13-continued

CIC analysis of exemplified anti-human MCT1 antibodies

| MCT1 Antibody | IgG column RT [min] | Blank column RT [min] | IgG column peak width [min] | Blank column peak width [min] | IgG K' (column retention time ratio) |
|---|---|---|---|---|---|
| Ab12 | 5.29 | 4.95 | 1.46 | 1.08 | 0.07 |
| Ab13 | 5.33 | 4.98 | 1.63 | 0.94 | 0.07 |
| Ab14 | 5.29 | 4.95 | 1.51 | 1.06 | 0.07 |
| Ab15 | 5.27 | 4.83 | 1.55 | 1.17 | 0.09 |
| Ab16 | 5.4 | 5 | 1.89 | 0.89 | 0.08 |
| Ab17 | 5.19 | 4.92 | 1.36 | 1.1 | 0.05 |
| Ab18 | 5.35 | 4.98 | 1.64 | 1.04 | 0.08 |
| Ab19 | 5.41 | 5 | 1.94 | 0.88 | 0.08 |
| INX444 IgG1EN | 11 | 6.81 | 8 | 3 | 0.615 |

Solubility: Solubility was assessed by concentrating 100 mg of the exemplified anti-human MCT1 antibodies with a 30 kDa molecular weight cut-off centrifugal filter (for example, Amicon U.C. filters, Millipore, catalog #UFC903024) to a volume of approximately 0.5 mL. The final concentration of the sample was measured by using a Solo VPE spectrophotometer (C Technologies, Inc). The results showed that the exemplified anti-human MCT1 antibodies had high solubility.

Thermal Stability: Differential Scanning Calorimetry (DSC) was used to evaluate the stability of exemplified anti-human MCT1 antibodies against thermal denaturation. DSC was run using a Malvern MircoCal VP-DSC instrument. Samples were heated from 20° C. to 110° C. at a constant rate of 60° C./hour. Analysis methods were performed using the MicroCal VP-Capillary DSC Automated Analysis program. Baseline corrections were performed, and T onset and TMs were determined. The results showed that the exemplified anti-human MCT1 antibodies had comparable Tm and acceptable thermal stability for development.

Chemical Stability: Stability of the exemplified MCT1 antibodies is assessed at a high concentration (approximately 100 mg/mL) in an acceptable buffer. Concentrated samples are incubated for a period of 4 weeks at 5° C. and 35° C. Following incubation, samples are analyzed for the percentage of main peak loss (Δ% MainPeak) with size exclusion chromatography (SEC), for fragmentation by capillary electrophoresis (CE-SDS), and for chemical modification (for example deamidation, isomerization, or oxidation) by LCMS peptide mapping.

Freeze/thaw stability: Freeze/thaw stability is evaluated at a high concentration (approximately 100 mg/mL), using a slow 3 repeat, controlled temperature cycle which mimics the freeze/thaw conditions of large volumes of bulk drug substance placed at −70° C.

Example 6: Immunogenicity Risk Profiling of the Exemplified Anti-Human MCT1 Antibodies Immunogenicity T-cell proliferation assay: The ability of the exemplified anti-human MCT1 antibodies or test candidate MAPPS peptides to activate CD4+ T cells by inducing cellular proliferation was assessed. CD8+ T cell depleted PBMC's were prepared and labeled with Carboxyfluorescein Diacetate Succinimidyl Ester (CFSE). Each sample was tested with media control, keyhole limpet haemocyanin (KLH; positive control), the respective therapeutic control (positive clinical benchmark antibody or peptide immunogenic control), exemplified antibodies, or test candidate MAPPS peptides. Cells were cultured and incubated for 7 days. On day 7, samples were analyzed by flow cytometry for a CD4+ T cell proliferative response. A median cellular division index (CDI) was calculated. 9 donors were assessed. Donors that produced a CDI≥2.5 were considered as positive responders. A percent donor frequency across all donors was evaluated.

The results as demonstrated in Table 14, show that the exemplified anti-human MCT1 antibodies tested, had significantly reduced T cell proliferation (ranging from 0% to 22% positive donor response) from the 9 donors tested, indicating low immunogenicity risk when compared to the positive control anti-CXCR4 antibody which demonstrated a 78% positive donor response. These results indicate a low immunogenicity risk profile for the exemplified anti-human MCT1 antibodies. The INX444 showed 89% positive donor response in the T cell proliferation assay, indicating a high immunogenicity risk profile.

TABLE 14

T cell proliferation assay to assess immunogenicity risk for the exemplified anti-human MCT1 antibodies

| Antibody | % Positive donor response |
|---|---|
| KLH | 100 |
| anti-CXCR4 | 78 |
| INX444 IgG1EN | 89 |
| Ab1 | 0 |
| Ab2 | 11 |
| Ab3 | 0 |
| Ab4 | 11 |
| Ab5 | 22 |
| Ab6 | 10 |
| Ab15 | 9 |
| Ab20 | 20 |
| Ab21 | 10 |

Serum protein binding: To further assess immunogenicity risk profile of the exemplified anti-human MCT1 antibodies serum protein binding was determined using mass spectrometry (MS). Antibodies diluted in PBS were coated at 4° C. overnight on Nunc MaxiSorp (or Immulon 4 HBX) microplates at 3 µg/well. Next day plates were washed 3× with 200 µL of cold PBS, and blocked with 100 µL of PBS/1% BSA at RT for 3 hrs. Blocking solution was removed, and plates were washed 3× again. 100 µL of human serum sample (pooled serum from eight donors, diluted 1:1 with PBS/protease inhibitors) was added to the wells, and plates were incubated at 4° C. overnight. Next day samples were removed, and plates were washed ten times with 200 µL cold PBS. Bound proteins were eluted with 1% acidic acid, reduced, alkylated, and digested with trypsin. Tryptic peptides were analyzed by nano LC/MS using a Thermo QE-HFX (or LUMOS) mass spectrometer. Peptide and protein identifications were generated by an internal proteomics pipeline using search algorithms with tryptic enzyme and a human database with test antibody sequences appended. Ions were quantified by internal proteomics tools (Chrom-Alignment, Meta-consense and Quant) and analyzed in JMP using Oneway analysis/Each Pair, Student's t test (or All pairs, Tukey HSD) platform. Ions with p<0.05 and difference >1 were considered as enriched.

The results of the MS analysis showed that the exemplified anti-human MCT1 antibodies did not have detectable binding to serum proteins. This lack of binding indicates a reduced immunogenicity risk and a reduced risk of faster clearance, thus providing a potentially desirable safety immunogenicity risk and PK profile for the exemplified anti-human MCT1 antibodies. The results further showed that INX444 bound to multiple apolipoproteins in the serum, indicating a higher immunogenicity risk and potentially faster clearance.

Example 7: In Vivo Characterization of the Anti-Human MCT1 Abs

Graft versus Host Disease (GvHD) assay: Female NSG™ mice (NOD.Cg-Prkdc$^{scid}$ Il2rg$^{tm1Wjl}$/SzJ, JAX Labs, Stock #05557) were housed 3/cage at 72° C. under a 12 h light: dark cycle and allowed food and water ad libitum (n=33). Human PBMC's were isolated from LRS tubes obtained from the San Diego Blood Bank (San Diego CA) using SepMate 50 Ficol preparation tubes according to manufacturer's instructions (StemCell Technologies, Vancouver, BC). Freshly isolated PBMC's were suspended in PBS at 1.2×10$^8$ cells/mL and mice were engrafted with 100 μL PBMC's suspension intravenously on day 0 (1.2×10$^7$/cells/mouse, n=29); 4 mice were not engrafted with PBMC's as non-engrafted controls. On day 1, mice were divided into weight matched groups and dosed subcutaneously with a human IgG1EN isotype control antibody, or Ab1 or Ab6. Dosing continued once weekly for the remainder of the experiment. Health checks and body weight measurements were performed routinely. Spleen cells at the end of the study for the Ab6 treated mice were further evaluated for T regulatory cells expansion.

Figure 5:
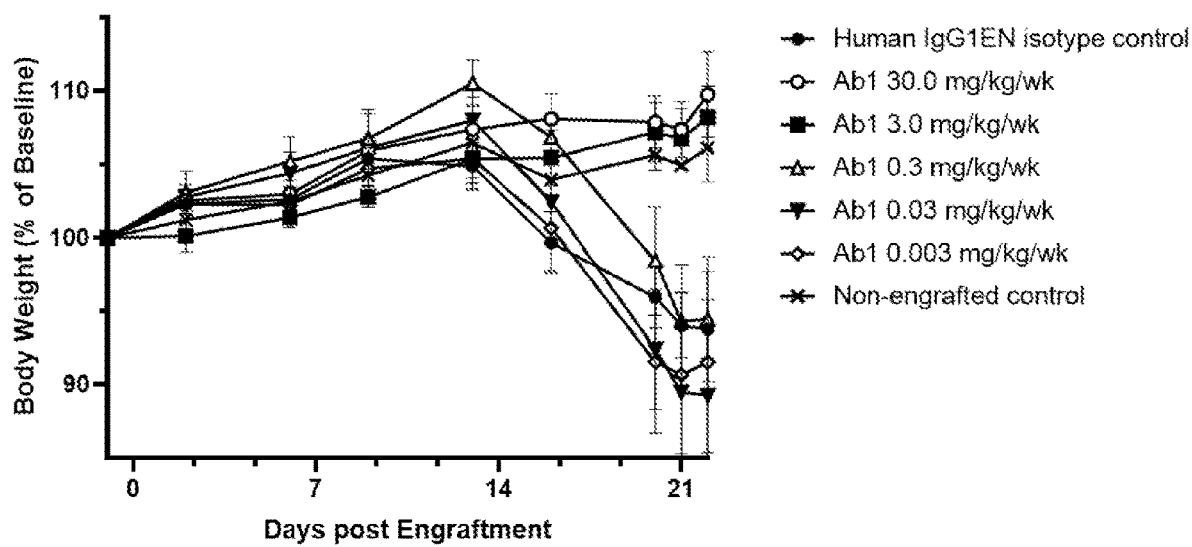
FIG. 5 shows anti-human MCT1 antibody Ab1 treated mice exhibit protection from weight loss in a GvHD mouse model.
Figure 6:
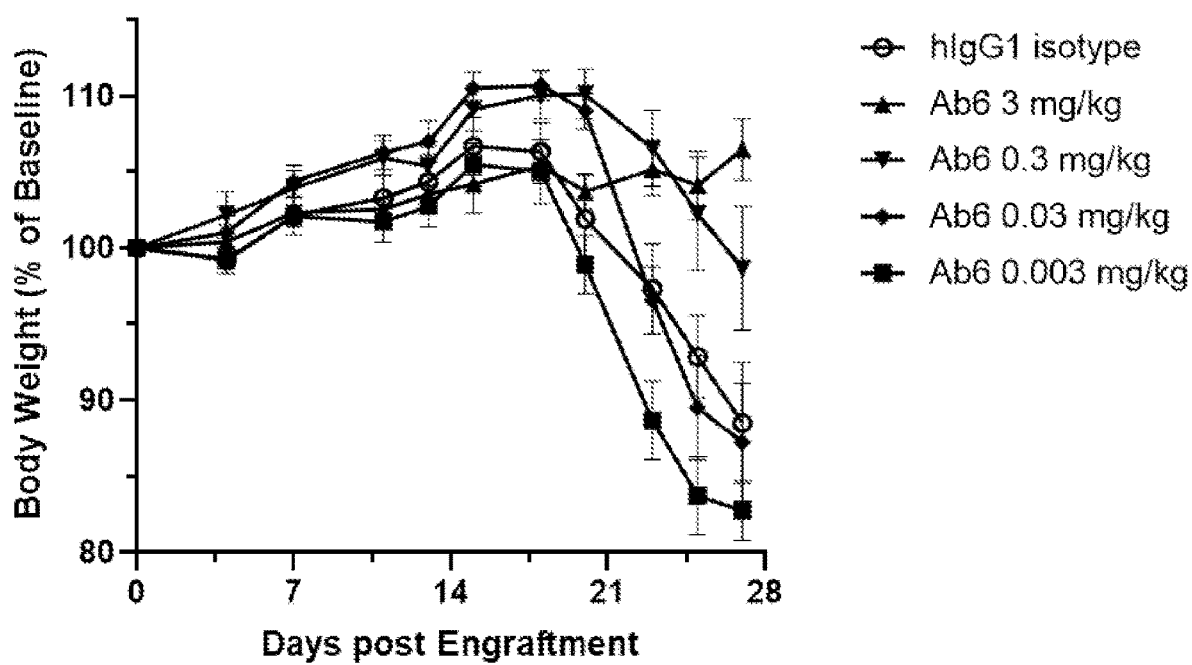
FIG. 6. shows anti-human MCT1 antibody Ab6 treated mice exhibit protection from weight loss in a GvHD mouse model.

The results as demonstrated in FIGS. 5 and 6 showed that treatment with Ab1 or Ab6 respectively could achieve full protection from weight loss, similar to the non-engrafted control group at specific doses. Surprisingly, as shown in Table 15, treatment with the anti-human MCT1 antibody Ab6 showed an expansion of FoxP3$^+$ regulatory T cells in the spleen cells at the end of the study when compared to the control. These results suggest that expansion of regulatory T cells induced by Ab6 may also contribute to the protection from weight loss.

TABLE 15

Increase in number of FoxP3+ regulatory T cells upon treatment with anti-human MCT1 antibody Ab6

| Concentration (nM) | Increase in average # of FoxP3+ Treg cells | Standard Deviation |
|---|---|---|
| human IgG1EN control | 21188 | 31304 |
| Ab6 3 mg/kg | 170708 | 104709 |
| Ab6 0.3 mg/kg | 25940 | 19596 |
| Ab6 0.03 mg/kg | 63008 | 95784 |
| Ab6 0.003 mg/kg | 14260 | 14443 |

SEQUENCES

Ab1

SEQ ID NO: 1 HCDR1 for Ab1, Ab2, Ab3, Ab4, and Ab5
TVSGFSLTNYHLQ

SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS SEQ ID NO: 3 HCDR3 for Ab1, Ab2, Ab3, Ab4, and Ab5
ARNSWYHGTYYSPGYYVMDA SEQ ID NO: 4 LCDR1 for Ab1, Ab2, Ab3, Ab4, Ab5, Ab20, and Ab21
KGSQNINNYLA SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YQYSDGYT SEQ ID NO: 7 VH for Ab1 and Ab2
QVQLVQSGAEVKKPGASVKVSCTVSGFSLTNYHLQWVRQAPGQGLEWMGFIRSSGNT
EYNSEFKSRVTMTRDTSTSTVYMELSSLRSEDTAVYYCARNSWYHGTYYSPGYYVMD
AWGQGTLVTVSS SEQ ID NO: 8 VL for Ab1, Ab20, and Ab21
EIVLTQSPGTLSLSPGERATLSCKGSQNINNYLAWYQQKPGQAPRLLIYNRHNLQTGIPD
RFSGSGSGTDFTLTISRLEPEDFAVYYCYQYSDGYTFGGGTKVEIK SEQ ID NO: 9 HC for Ab1 and Ab2
QVQLVQSGAEVKKPGASVKVSCTVSGFSLTNYHLQWVRQAPGQGLEWMGFIRSSGNT
EYNSEFKSRVTMTRDTSTSTVYMELSSLRSEDTAVYYCARNSWYHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK

| SEQUENCES |
|---|
| SEQ ID NO: 10 LC for Ab1, Ab20, and Ab21<br>EIVLTQSPGTLSLSPGERATLSCKGSQNINNYLAWYQQKPGQAPRLLIYNRHNLQTGIPD<br>RFSGSGSGTDFTLTISRLEPEDFAVYYCYQYSDGYTFGGGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC<br><br>SEQ ID NO: 11 HC DNA for Ab1 and Ab2<br>CAAGTCCAACTGGTGCAATCTGGGGCAGAGGTAAAGAAGCCTGGCGCATCAGTAAA<br>GGTAAGTTGCACTGTAAGCGGGTTCTCACTCACAAACTACCATCTGCAATGGGTTCG<br>ACAAGCTCCAGGGCAAGGCTTGGAATGGATGGGGTTCATAAGGAGCTCCGGGAACA<br>CAGAATATAACAGCGAGTTCAAGTCACGAGTCACAATGACACGGGACACCTCAACC<br>TCAACAGTTTACATGGAATTGTCTTCATTGCGTAGTGAGGACACCGCCGTTTACTAC<br>TGTGCTAGGAACTCCTGGTATCACGGTACCTACTATTCTCCTGGCTATTATGTAATGG<br>ATGCTTGGGGCCAGGGGACTCTGGTAACCGTTTCCTCCGCCTCCACCAAGGGCCCAT<br>CGGTCTTCCCCCTGGCACCCTCCTCCAAGAGCACCTCTGGGGGCACAGCGGCCCTGG<br>GCTGCCTGGTCAAGGACTACTTCCCCGAACCGGTGACGGTGTCGTGGAACTCAGGC<br>GCACTGACCAGCGGCGTGCACACCTTCCCGGCTGTCCTACAGTCCTCAGGACTCTAC<br>TCCCTCAGCAGCGTGGTGACCGTGCCCTCCAGCAGCTTGGGCACCCAGACCTACATC<br>TGCAACGTGAATCACAAGCCCAGCAACACCAAGGTGGACAAGAGAGTTGAGCCCAA<br>ATCTTGTGACAAAACTCACACATGCCCACCGTGCCCAGCACCTGAAGCCGAGGGGG<br>CACCGTCAGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAGGTCAAG<br>TTCAACTGGTATGTGGACGGCGTGGAGGTGCATAATGCCAAGACAAAGCCGCGGGA<br>GGAGCAGTACAACAGCACGTACCGTGTGGTCAGCGTCCTCACCGTCCTGCACCAAG<br>ACTGGCTGAATGGCAAGGAGTACAAGTGCAAGGTCTCCAACAAAGCCCTCCCATCC<br>TCCATCGAGAAAACCATCTCCAAAGCCAAAGGGCAGCCCCGAGAACCACAGGTGTA<br>CACCCTGCCCCCATCCCGGGAGGAGATGACCAAGAACCAAGTCAGCCTGACCTGCC<br>TGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTC<br>CTCTATTCCAAGCTCACCGTGGACAAGAGCAGGTGGCAGCAGGGGAACGTCTTCTC<br>ATGCTCCGTGATGCATGAGGCTCTGCACAACCACTACACGCAGAAGAGCCTCTCCCT<br>GTCTCCGGGCAAA<br><br>SEQ ID NO: 12 LC DNA for Ab1, Ab20, and Ab21<br>GAGATCGTCCTCACCCAGTCTCCCGGCACATTGAGTTTGAGTCCAGGTGAAAGAGCA<br>ACACTGAGCTGCAAAGGTAGCCAGAACATCAATAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGGAGGGACAAAAGTGGAAATAAAGCGAACCGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |

| Ab2 |
|---|
| SEQ ID NO: 1 HCDR1 for Ab1, Ab2, Ab3, Ab4, and Ab5<br>TVSGFSLTNYHLQ<br><br>SEQ ID NO: 2 HCDR2 for Ab1, Ab2, Ab3, Ab4, Ab5, Ab7, Ab9, Ab10, Ab11, Ab12, Ab13,<br>Ab14, Ab15, Ab16, Ab17, Ab18, Ab20, and Ab21<br>FIRSSGNTEYNSEFKS<br><br>SEQ ID NO: 3 HCDR3 for Ab1, Ab2, Ab3, Ab4, and Ab5<br>ARNSWYHGTYYSPGYYVMDA<br><br>SEQ ID NO: 4 LCDR1 for Ab1, Ab2, Ab3, Ab4, Ab5, Ab20, and Ab21<br>KGSQNINNYLA<br><br>SEQ ID NO: 5 LCDR2 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YNRHNLQT<br><br>SEQ ID NO: 6 LCDR3 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YQYSDGYT<br><br>SEQ ID NO: 7 VH for Ab1 and Ab2<br>QVQLVQSGAEVKKPGASVKVSCTVSGFSLTNYHLQWVRQAPGQGLEWMGFIRSSGNT<br>EYNSEFKSRVTMTRDTSTSTVYMELSSLRSEDTAVYYCARNSWYHGTYYSPGYYVMD<br>AWGQGTLVTVSS |

SEQUENCES

SEQ ID NO: 13 VL for Ab2 and Ab3
DIQMTQSPSTLSASVGDRVTITCKGSQNINNYLAWYQQKPGKAPKLLIYNRHNLQTGVP
SRFSGSGSGTEFTLTISSLQPDDFATYYCYQYSDGYTFGGGTKVEIK SEQ ID NO: 9 HC for Ab1 and Ab2
QVQLVQSGAEVKKPGASVKVSCTVSGFSLTNYHLQWVRQAPGQGLEWMGFIRSSGNT
EYNSEFKSRVTMTRDTSTSTVYMELSSLRSEDTAVYYCARNSWYHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 15 LC for Ab2 and Ab3
DIQMTQSPSTLSASVGDRVTITCKGSQNINNYLAWYQQKPGKAPKLLIYNRHNLQTGVP
SRFSGSGSGTEFTLTISSLQPDDFATYYCYQYSDGYTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC SEQ ID NO: 11 HC DNA for Ab1 and Ab2
CAAGTCCAACTGGTGCAATCTGGGGCAGAGGTAAAGAAGCCTGGCGCATCAGTAAA
GGTAAGTTGCACTGTAAGCGGGTTCTCACTCACAAACTACCATCTGCAATGGGTTCG
ACAAGCTCCAGGGCAAGGCTTGGAATGGATGGGGTTCATAAGGAGCTCCGGGAACA
CAGAATATAACAGCGAGTTCAAGTCACGAGTCACAATGACACGGGACACCTCAACC
TCAACAGTTTACATGGAATTGTCTTCATTGCGTAGTGAGGACACCGCCGTTTACTAC
TGTGCTAGGAACTCCTGGTATCACGGTACCTACTATTCTCCTGGCTATTATGTAATGG
ATGCTTGGGGCCAGGGGACTCTGGTAACCGTTTCCTCCGCCTCCACCAAGGGCCCAT
CGGTCTTCCCCCTGGCACCCTCCTCCAAGAGCACCTCTGGGGGCACAGCGGCCCTGG
GCTGCCTGGTCAAGGACTACTTCCCCGAACCGGTGACGGTGTCGTGGAACTCAGGC
GCACTGACCAGCGGCGTGCACACCTTCCCGGCTGTCCTACAGTCCTCAGGACTCTAC
TCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAA
ATCTTGTGACAAAACTCACACATGCCCACCGTGCCCAGCACCTGAAGCCGAGGGGG
CACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAG
TTCAACTGGTATGTGGACGGCGTGGAGGTGCATAATGCCAAGACAAAGCCGCGGGA
GGAGCAGTACAACAGCACGTACCGTGTGGTCAGCGTCCTCACCGTCCTGCACCAAG
ACTGGCTGAATGGCAAGGAGTACAAGTGCAAGGTCTCCAACAAAGCCCTCCCATCC
TCCATCGAGAAAACCATCTCCAAAGCCAAAGGGCAGCCCCGAGAACCACAGGTGTA
CACCCTGCCCCCATCCCGGGAGGAGATGACCAAGAACCAAGTCAGCCTGACCTGCC
TGGTCAAAGGCTTCTATCCCAGCGACATCGCCGTGGAGTGGGAGAGCAATGGGCAG
CCGGAGAACAACTACAAGACCACGCCTCCCGTGCTGGACTCCGACGGCTCCTTCTTC
CTCTATTCCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCT
GTCTCCGGGCAAA SEQ ID NO: 17 LC DNA for Ab2 and Ab3
GATATTCAGATGACACAGAGCCCTTCCACCCTGAGCGCCAGTGTAGGCGACCGGGT
AACTATAACATGTAAAGGCTCACAAAACATCAATAACTATTTGGCCTGGTATCAGCA
AAAGCCAGGAAAAGCTCCTAAACTCTTGATATACAACAGACATAACTTGCAAACTG
GGGTGCCAAGTCGCTTCAGCGGGAGTGGCTCAGGTACAGAGTTTACTCTTACCATTT
CCTCCCTGCAACCTGACGATTTTGCCACCTACTATTGCTACCAATATTCCGATGGATA
CACTTTCGGGGGTGGTACTAAAGTTGAGATTAAGCGAACCGTGGCTGCACCATCTGT
CTTCATCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGATAACGC
CCTCCAATCGGGTAACTCCCAGGAGAGTGTCACAGAGCAGGACAGCAAGGACAGCA
CCTACAGCCTCAGCAGCACCCTGACGCTGAGCAAAGCAGACTACGAGAAACACAAA
GTCTACGCCTGCGAAGTCACCCATCAGGGCCTGAGCTCGCCCGTCACAAAGAGCTTC
AACAGGGGAGAGTGC

Ab3

SEQ ID NO: 1 HCDR1 for Ab1, Ab2, Ab3, Ab4, and Ab5
TVSGFSLTNYHLQ

SEQ ID NO: 2 HCDR2 for Ab1, Ab2, Ab3, Ab4, Ab5, Ab7, Ab9, Ab10, Ab11, Ab12, Ab13,
Ab14, Ab15, Ab16, Ab17, Ab18, Ab20, and Ab21
FIRSSGNTEYNSEFKS SEQ ID NO: 3 HCDR3 for Ab1, Ab2, Ab3, Ab4, and Ab5
ARNSWYHGTYYSPGYYVMDA SEQ ID NO: 4 LCDR1 for Ab1, Ab2, Ab3, Ab4, Ab5, Ab20, and Ab21
KGSQNINNYLA

| SEQUENCES |
| --- |
| SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21<br>YNRHNLQT |
| SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21<br>YQYSDGYT |
| SEQ ID NO: 18 VH for Ab3<br>EVQLVESGGGLVQPGGSLRLSCTVSGFSLTNYHLQWVRQAPGKGLEWVGFIRSSGNTE<br>YNSEFKSRFTISRDDSKNSLYLQMNSLKTEDTAVYYCARNSWYHGTYYSPGYYVMDA<br>WGQGTLVTVSS |
| SEQ ID NO: 13 VL for Ab2 and Ab3<br>DIQMTQSPSTLSASVGDRVTITCKGSQNINNYLAWYQQKPGKAPKLLIYNRHNLQTGVP<br>SRFSGSGSGTEFTLTISSLQPDDFATYYCYQYSDGYTFGGGTKVEIK |
| SEQ ID NO: 19 HC for Ab3<br>EVQLVESGGGLVQPGGSLRLSCTVSGFSLTNYHLQWVRQAPGKGLEWVGFIRSSGNTE<br>YNSEFKSRFTISRDDSKNSLYLQMNSLKTEDTAVYYCARNSWYHGTYYSPGYYVMDA<br>WGQGTLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKRVEPKSCDKTHT<br>CPPCPAPEAEGAPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPSSIEKTISKAKGQ<br>PREPQVYTLPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO: 15 LC for Ab2 and Ab3<br>DIQMTQSPSTLSASVGDRVTITCKGSQNINNYLAWYQQKPGKAPKLLIYNRHNLQTGVP<br>SRFSGSGSGTEFTLTISSLQPDDFATYYCYQYSDGYTFGGGTKVEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC |
| SEQ ID NO: 20 HC DNA for Ab3<br>GAAGTCCAACTTGTAGAATCTGGGGGAGGACTGGTCCAACCTGGCGGCAGCCTGCG<br>ACTGTCTTGCACTGTCAGTGGATTTTCCTCACCAACTACCATCTTCAATGGGTCCGA<br>CAAGCCCCCGGAAAAGGACTGGAATGGGTGGGCTTCATAAGATCAAGTGGTAACAC<br>AGAGTACAACTCAGAATTCAAGTCACGTTTTACCATAAGCCGCGATGACAGCAAAA<br>ATAGCTTGTACCTTCAAATGAACTCTCTCAAGACCGAGGATACCGCCGTGTATTACT<br>GCGCTCGGAATAGCTGGTACCACGGAACATATTACTCTCCCGGTTACTATGTTATGG<br>ACGCTTGGGGGCAGGGTACATTGGTTACCGTCTCCAGCGCCTCCACCAAGGGCCCAT<br>CGGTCTTCCCCCTGGCACCCTCCTCCAAGAGCACCTCTGGGGGCACAGCGGCCCTGG<br>GCTGCCTGGTCAAGGACTACTTCCCCGAACCGGTGACGGTGTCGTGGAACTCAGGC<br>GCACTGACCAGCGGCGTGCACACCTTCCCGGCTGTCCTACAGTCCTCAGGACTCTAC<br>TCCCTCAGCAGCGTGGTGACCGTGCCCTCCAGCAGCTTGGGCACCCAGACCTACATC<br>TGCAACGTGAATCACAAGCCCAGCAACACCAAGGTGGACAAGAGAGTTGAGCCCAA<br>ATCTTGTGACAAAACTCACACATGCCCACCGTGCCCAGCACCTGAAGCCGAGGGGG<br>CACCGTCAGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAGGTCAAG<br>TTCAACTGGTATGTGGACGGCGTGGAGGTGCATAATGCCAAGACAAAGCCGCGGGA<br>GGAGCAGTACAACAGCACGTACCGTGTGGTCAGCGTCCTCACCGTCCTGCACCAAG<br>ACTGGCTGAATGGCAAGGAGTACAAGTGCAAGGTCTCCAACAAAGCCCTCCCATCC<br>TCCATCGAGAAAACCATCTCCAAAGCCAAAGGGCAGCCCCGAGAACCACAGGTGTA<br>CACCCTGCCCCCATCCCGGGAGGAGATGACCAAGAACCAAGTCAGCCTGACCTGCC<br>TGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTC<br>CTCTATTCCAAGCTCACCGTGGACAAGAGCAGGTGGCAGCAGGGGAACGTCTTCTC<br>ATGCTCCGTGATGCATGAGGCTCTGCACAACCACTACACGCAGAAGAGCCTCTCCCT<br>GTCTCCGGGCAAA |
| SEQ ID NO: 17 LC DNA for Ab2 and Ab3<br>GATATTCAGATGACACAGAGCCCTTCCACCCTGAGCGCCAGTGTAGGCGACCGGGT<br>AACTATAACATGTAAAGGCTCACAAAACATCAATAACTATTTGGCCTGGTATCAGCA<br>AAAGCCAGGAAAAGCTCCTAAACTCTTGATATACAACAGACATAACTTGCAAACTG<br>GGGTGCCAAGTCGCTTCAGCGGGAGTGGCTCAGGTACAGAGTTTACTCTTACCATTT<br>CCTCCCTGCAACCTGACGATTTTGCCACCTACTATTGCTACCAATATTCCGATGGATA<br>CACTTTCGGGGGTGGTACTAAAGTTGAGATTAAGCGAACCGTGGCTGCACCATCTGT<br>CTTCATCTTCCCGCCATCTGATGAGCAGTTGAAATCTGGAACTGCCTCTGTTGTGTGC<br>CTGCTGAATAACTTCTATCCCAGAGAGGCCAAAGTACAGTGGAAGGTGGATAACGC<br>CCTCCAATCGGGTAACTCCCAGGAGAGTGTCACAGAGCAGGACAGCAAGGACAGCA<br>CCTACAGCCTCAGCAGCACCCTGACGCTGAGCAAAGCAGACTACGAGAAACACAAA<br>GTCTACGCCTGCGAAGTCACCCATCAGGGCCTGAGCTCGCCCGTCACAAAGAGCTTC<br>AACAGGGGAGAGTGC |

| SEQUENCES |
| --- |
| Ab4 |

SEQ ID NO: 1 HCDR1 for Ab1, Ab2, Ab3, Ab4, and Ab5
TVSGFSLTNYHLQ

SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS SEQ ID NO: 3 HCDR3 for Ab1, Ab2, Ab3, Ab4, and Ab5
ARNSWYHGTYYSPGYYVMDA SEQ ID NO: 4 LCDR1 for Ab1, Ab2, Ab3, Ab4, Ab5, Ab20, and Ab21
KGSQNINNYLA SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YQYSDGYT SEQ ID NO: 21 VH for Ab4
EVQLVESGGGLVKPGGSLRLSCTVSGFSLTNYHLQWVRQAPGKGLEWVGFIRSSGNTE
YNSEFKSRFTISRDDSKNTLYLQMNSLKTEDTAVYYCARNSWYHGTYYSPGYYVMDA
WGQGTLVTVSS SEQ ID NO: 22 VL for Ab4 and Ab5
DIQMTQSPSSLSASVGDRVTITCKGSQNINNYLAWYQQKPGKAPKLLIYNRHNLQTGVP
SRFSGSGSGTDFTLTISSLQPEDFATYYCYQYSDGYTFGGGTKVEIK SEQ ID NO: 23 HC for Ab4
EVQLVESGGGLVKPGGSLRLSCTVSGFSLTNYHLQWVRQAPGKGLEWVGFIRSSGNTE
YNSEFKSRFTISRDDSKNTLYLQMNSLKTEDTAVYYCARNSWYHGTYYSPGYYVMDA
WGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHT
CPPCPAPEAEGAPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPSSIEKTISKAKGQ
PREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID NO: 24 LC for Ab4 and Ab5
DIQMTQSPSSLSASVGDRVTITCKGSQNINNYLAWYQQKPGKAPKLLIYNRHNLQTGVP
SRFSGSGSGTDFTLTISSLQPEDFATYYCYQYSDGYTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC SEQ ID NO: 25 HC DNA for Ab4
GAAGTCCAGCTGGTAGAATCTGGTGGTGGGTTGGTCAAACCCGGCGGGAGCCTTAG
ACTGTCATGTACTGTATCAGGTTTTTCATTGACAAATTATCATCTCCAGTGGGTACGA
CAAGCCCCTGGAAAGGGGCTCGAATGGGTAGGTTTTATCAGAAGTTCAGGCAACAC
AGAATACAACTCAGAGTTCAAGTCTCGTTTTACCATAAGCCGCGATGACTCTAAAAA
CACACTGTACCTTCAGATGAACTCTCTCAAGACCGAAGACACCGCCGTCTACTATTG
CGCTAGAAATAGTTGGTACCATGGTACATACTACTCCTGGATATTACGTCATGGA
CGCCTGGGGCCAGGGGACTCTTGTGACAGTTTCCTCCGCCTCCACCAAGGGCCCATC
GGTCTTCCCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTCAGGCGC
ACTGACCAGCGGCGTGCACACCTTCCCGGCTGTCCTACAGTCCTCAGGACTCTACTC
CCTCAGCAGCGTGGTGACCGTGCCCTCCAGCAGCTTGGGCACCCAGACCTACATCTG
CAACGTGAATCACAAGCCCAGCAACACCAAGGTGGACAAGAGAGTTGAGCCCAAAT
CTTGTGACAAAACTCACACATGCCCACCGTGCCCAGCACCTGAAGCCGAGGGGGCA
CCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTT
CAACTGGTATGTGGACGGCGTGGAGGTGCATAATGCCAAGACAAAGCCGCGGGAGG
AGCAGTACAACAGCACGTACCGTGTGGTCAGCGTCCTCACCGTCCTGCACCAAGACT
GGCTGAATGGCAAGGAGTACAAGTGCAAGGTCTCCAACAAAGCCCTCCCATCCTCC
ATCGAGAAAACCATCTCCAAAGCCAAAGGGCAGCCCCGAGAACCACAGGTGTACAC
CCTGCCCCCATCCCGGGAGGAGATGACCAAGAACCAAGTCAGCCTGACCTGCCTGG
TCAAAGGCTTCTATCCCAGCGACATCGCCGTGGAGTGGGAGAGCAATGGGCAGCCG
GAGAACAACTACAAGACCACGCCTCCCGTGCTGGACTCCGACGGCTCCTTCTTCCTC
TATTCCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTGTC
TCCGGGCAAA

| SEQUENCES |
|---|
| SEQ ID NO: 26 LC DNA for Ab4 and Ab5<br>GATATTCAAATGACACAATCTCCCTCCAGCCTGTCAGCCTCTGTTGGAGACAGGGTA<br>ACTATAACATGCAAAGGCTCCCAAAACATAAATAATTACTTGGCCTGGTATCAACAG<br>AAACCTGGTAAGGCACCTAAGCTGCTCATCTACAATAGGCATAACCTTCAGACTGGC<br>GTTCCTTCTAGGTTTAGCGGGTCAGGGTCCGGTACCGATTTTACCCTCACAATATCCA<br>GTCTTCAACCCGAGGACTTCGCAACATATTATTGTTATCAGTATTCTGATGGTTACAC<br>CTTCGGAGGGGGAACTAAGGTGGAGATCAAGCGAACCGTGGCTGCACCATCTGTCT<br>TCATCTTCCCGCCATCTGATGAGCAGTTGAAATCTGGAACTGCCTCTGTTGTGTGCCT<br>GCTGAATAACTTCTATCCCAGAGAGGCCAAAGTACAGTGGAAGGTGGATAACGCCC<br>TCCAATCGGGTAACTCCCAGGAGAGTGTCACAGAGCAGGACAGCAAGGACAGCACC<br>TACAGCCTCAGCAGCACCCTGACGCTGAGCAAAGCAGACTACGAGAAACACAAAGT<br>CTACGCCTGCGAAGTCACCCATCAGGGCCTGAGCTCGCCCGTCACAAAGAGCTTCA<br>ACAGGGGAGAGTGC |

| Ab5 |
|---|
| SEQ ID NO: 1 HCDR1 for Ab1, Ab2, Ab3, Ab4, and Ab5<br>TVSGFSLTNYHLQ<br><br>SEQ ID NO: 2 HCDR2 for Ab1, Ab2, Ab3, Ab4, Ab5, Ab7, Ab9, Ab10, Ab11, Ab12, Ab13,<br>Ab14, Ab15, Ab16, Ab17, Ab18, Ab20, and Ab21<br>FIRSSGNTEYNSEFKS<br><br>SEQ ID NO: 3 HCDR3 for Ab1, Ab2, Ab3, Ab4, and Ab5<br>ARNSWYHGTYYSPGYYVMDA<br><br>SEQ ID NO: 4 LCDR1 for Ab1, Ab2, Ab3, Ab4, Ab5, Ab20, and Ab21<br>KGSQNINNYLA<br><br>SEQ ID NO: 5 LCDR2 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YNRHNLQT<br><br>SEQ ID NO: 6 LCDR3 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YQYSDGYT<br><br>SEQ ID NO: 27 VH for Ab5<br>EVQLVQSGAEVKKPGESLKISCTVSGFSLTNYHLQWVRQMPGKGLEWMGFIRSSGNTE<br>YNSEFKSQVTISADKSISTAYLQWSSLKASDTAMYYCARNSWYHGTYYSPGYYVMDA<br>WGQGTLVTVSS<br><br>SEQ ID NO: 22 VL for Ab4 and Ab5<br>DIQMTQSPSSLSASVGDRVTITCKGSQNINNYLAWYQQKPGKAPKLLIYNRHNLQTGVP<br>SRFSGSGSGTDFTLTISSLQPEDFATYYCYQYSDGYTFGGGTKVEIK<br><br>SEQ ID NO: 28 HC for Ab5<br>EVQLVQSGAEVKKPGESLKISCTVSGFSLTNYHLQWVRQMPGKGLEWMGFIRSSGNTE<br>YNSEFKSQVTISADKSISTAYLQWSSLKASDTAMYYCARNSWYHGTYYSPGYYVMDA<br>WGQGTLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKRVEPKSCDKTHT<br>CPPCPAPEAEGAPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPSSIEKTISKAKGQ<br>PREPQVYTLPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK<br><br>SEQ ID NO: 24 LC for Ab4 and Ab5<br>DIQMTQSPSSLSASVGDRVTITCKGSQNINNYLAWYQQKPGKAPKLLIYNRHNLQTGVP<br>SRFSGSGSGTDFTLTISSLQPEDFATYYCYQYSDGYTFGGGTKVEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 29 HC DNA for Ab5<br>GAGGTCCAACTTGTTCAGTCCGGTGCTGAGGTGAAAAAGCCTGGAGAATCACTGAA<br>AATTAGTTGCACCGTATCTGGCTTTTCTCTTACCAACTACCACCTCCAATGGGTAAGA<br>CAGATGCCAGGGAAAGGTTTGGAGTGGATGGGTTTCATCCGGTCCTCCGGCAACAC<br>CGAATATAACAGTGAGTTTAAAAGTCAGGTTACTATTTCCGCCGATAAGAGCATTTC<br>AACCGCCTACCTTCAGTGGTCCAGTTTGAAGGCATCTGACACAGCAATGTATTATTG<br>TGCTCGAAACTCCTGGTATCATGGAACATACTATTCACCAGGGTACTACGTGATGGA<br>TGCATGGGGTCAGGGTACCCTCGTCACAGTAAGCTCTGCCTCCACCAAGGGCCCATC<br>GGTCTTCCCCCTGGCACCCTCCTCCAAGAGCACCTCTGGGGGCACAGCGGCCCTGGG<br>CTGCCTGGTCAAGGACTACTTCCCCGAACCGGTGACGGTGTCGTGGAACTCAGGCGC<br>ACTGACCAGCGGCGTGCACACCTTCCCGGCTGTCCTACAGTCCTCAGGACTCTACTC<br>CCTCAGCAGCGTGGTGACCGTGCCCTCCAGCAGCTTGGGCACCCAGACCTACATCTG<br>CAACGTGAATCACAAGCCCAGCAACACCAAGGTGGACAAGAGAGTTGAGCCCAAAT<br>CTTGTGACAAAACTCACACATGCCCACCGTGCCCAGCACCTGAAGCCGAGGGGGCA<br>CCGTCAGTCTTCCTCTTCCCCCCAAAACCCAAGGACACCCTCATGATCTCCCGGACC |

| SEQUENCES |
|---|
| CCTGAGGTCACATGCGTGGTGGTGGACGTGAGCCACGAAGACCCTGAGGTCAAGTT<br>CAACTGGTATGTGGACGGCGTGGAGGTGCATAATGCCAAGACAAAGCCGCGGGAGG<br>AGCAGTACAACAGCACGTACCGTGTGGTCAGCGTCCTCACCGTCCTGCACCAAGACT<br>GGCTGAATGGCAAGGAGTACAAGTGCAAGGTCTCCAACAAAGCCCTCCCATCCTCC<br>ATCGAGAAAACCATCTCCAAAGCCAAAGGGCAGCCCCGAGAACCACAGGTGTACAC<br>CCTGCCCCCATCCCGGGAGGAGATGACCAAGAACCAAGTCAGCCTGACCTGCCTGG<br>TCAAAGGCTTCTATCCCAGCGACATCGCCGTGGAGTGGGAGAGCAATGGGCAGCCG<br>GAGAACAACTACAAGACCACGCCTCCCGTGCTGGACTCCGACGGCTCCTTCTTCCTC<br>TATTCCAAGCTCACCGTGGACAAGAGCAGGTGGCAGCAGGGGAACGTCTTCTCATG<br>CTCCGTGATGCATGAGGCTCTGCACAACCACTACACGCAGAAGAGCCTCTCCCTGTC<br>TCCGGGCAAA |

SEQ ID NO: 26 LC DNA for Ab4 and Ab5
GATATTCAAATGACACAATCTCCCTCCAGCCTGTCAGCCTCTGTTGGAGACAGGGTA
ACTATAACATGCAAAGGCTCCCAAAACATAAATAATTACTTGGCCTGGTATCAACAG
AAACCTGGTAAGGCACCTAAGCTGCTCATCTACAATAGGCATAACCTTCAGACTGGC
GTTCCTTCTAGGTTTAGCGGGTCAGGGTCCGGTACCGATTTTACCCTCACAATATCCA
GTCTTCAACCCGAGGACTTCGCAACATATTATTGTTATCAGTATTCTGATGGTTACAC
CTTCGGAGGGGGAACTAAGGTGGAGATCAAGCGAACCGTGGCTGCACCATCTGTCT
TCATCTTCCCGCCATCTGATGAGCAGTTGAAATCTGGAACTGCCTCTGTTGTGTGCCT
GCTGAATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACAGCACC
TACAGCCTCAGCAGCACCCTGACGCTGAGCAAAGCAGACTACGAGAAACACAAAGT
CTACGCCTGCGAAGTCACCCATCAGGGCCTGAGCTCGCCCGTCACAAAGAGCTTCA
ACAGGGGAGAGTGC

| Ab6 |
|---|

SEQ ID NO: 30 HCDR1 for Ab6, Ab8, Ab11, Ab13, Ab14, Ab15, Ab19, Ab20, and Ab21
TVSGRSLTNYHLQ SEQ ID NO: 31 HCDR2 for Ab6
FIRSSGNTEYNSRFKS SEQ ID NO: 32 HCDR3 for Ab6, Ab7, Ab8, Ab9, Ab10, Ab12, Ab16, Ab17, Ab18, and Ab19
ARNRWYHGTYYSPGYYVMDA SEQ ID NO: 33 LCDR1 for Ab6, Ab7, Ab8, Ab9, Ab10, Ab11, Ab12, Ab13, Ab14, Ab15, Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YQYSDGYT SEQ ID NO: 34 VH for Ab6
QVQLVQSGAEVKKPGASVKVSCTVSGRSLTNYHLQWVRQAPGQGLEWMGFIRSSGNT
EYNSRFKSRVTMTRDTSTSTVYMELSSLRSEDTAVYYCARNRWYHGTYYSPGYYVMD
AWGQGTLVTVSS SEQ ID NO: 35 VL for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 36 HC for Ab6
QVQLVQSGAEVKKPGASVKVSCTVSGRSLTNYHLQWVRQAPGQGLEWMGFIRSSGNT
EYNSRFKSRVTMTRDTSTSTVYMELSSLRSEDTAVYYCARNRWYHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC

| SEQUENCES |
|---|
| SEQ ID NO: 38 HC DNA for Ab6<br>CAAGTGCAGCTGGTGCAGTCCGGTGCCGAAGTCAAGAAGCCCGGTGCTTCGGTGAA<br>AGTGTCATGTACCGTGTCCGGACGCTCCTTGACGAACTACCATCTCCAATGGGTAG<br>ACAGGCGCCTGGACAGGGACTGGAATGGATGGGCTTCATCCGGTCCTCGGGGAATA<br>CCGAGTACAACAGCCGGTTCAAGTCCCGCGTGACCATGACTCGGGACACCAGCACC<br>TCAACCGTGTACATGGAGCTTAGCAGCCTGCGCTCTGAGGACACTGCCGTGTACTAC<br>TGCGCCCGGAACAGATGGTACCACGGGACCTACTACTCGCCGGGCTATTACGTGAT<br>GGATGCATGGGGACAGGGCACTCTGGTCACTGTGTCCTCCGCTAGCACCAAGGGCC<br>CATCGGTCTTCCCCCTGGCACCCTCCTCCAAGAGCACCTCTGGGGGCACAGCGGCCC<br>TGGGCTGCCTGGTCAAGGACTACTTCCCCGAACCGGTGACGGTGTCGTGGAACTCAG<br>GCGCACTGACCAGCGGCGTGCACACCTTCCCGGCTGTCCTACAGTCCTCAGGACTCT<br>ACTCCCTCAGCAGCGTGGTGACCGTGCCCTCCAGCAGCTTGGGCACCCAGACCTACA<br>TCTGCAACGTGAATCACAAGCCCAGCAACACCAAGGTGGACAAGAGAGTTGAGCCC<br>AAATCTTGTGACAAAACTCACACATGCCCACCGTGCCCAGCACCTGAAGCCGAGGG<br>GGCACCGTCAGTCTTCCTCTTCCCCCCAAAACCCAAGGACACCCTCATGATCTCCCG<br>GACCCCTGAGGTCACATGCGTGGTGGTGGACGTGAGCCACGAAGACCCTGAGGTCA<br>AGTTCAACTGGTATGTGGACGGCGTGGAGGTGCATAATGCCAAGACAAAGCCGCGG<br>GAGGAGCAGTACAACAGCACGTACCGTGTGGTCAGCGTCCTCACCGTCCTGCACCA<br>AGACTGGCTGAATGGCAAGGAGTACAAGTGCAAGGTTTCCAACAAAGCCCTCCCAT<br>CCTCCATCGAGAAAACCATCTCCAAAGCCAAAGGGCAGCCCCGAGAACCACAGGTG<br>TACACCCTGCCCCCATCCCGGGAGGAGATGACCAAGAACCAAGTCAGCCTGACCTG<br>CCTGGTCAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGCTCCTTCT<br>TCCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA |
| SEQ ID NO: 39 LC DNA for Ab6, Ab7, Ab8, Ab9, Ab10, Ab11, Ab12, Ab13, Ab14, Ab15, Ab16, Ab17, Ab18, and Ab19<br>GAGATCGTCCTCACCCAGTCTCCCGGCACATTGAGTTTGAGTCCAGGTGAAAGAGCA<br>ACACTGAGCTGCAAAGGTAGCCAGAACATCGAGAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |

Ab7

SEQ ID NO: 40 HCDR1 for Ab7
TVSGRSRTNYHLQ

SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS SEQ ID NO: 32 HCDR3 for Ab6, Ab7, Ab8, Ab9, Ab10, Ab12, Ab16, Ab17, Ab18, and Ab19
ARNRWYHGTYYSPGYYVMDA SEQ ID NO: 33 LCDR1 for Ab6, Ab7, Ab8, Ab9, Ab10, Ab11, Ab12, Ab13, Ab14, Ab15, Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YQYSDGYT SEQ ID NO: 41 VH for Ab7
QVQLVQSGAEVKKPGASVKVSCTVSGRSRTNYHLQWVRQAPGQGLEWMGFIRSSGNT
EYNSEFKSRVTMTRDTSTSTVYMELSSLRSEDTAVYYCARNRWYHGTYYSPGYYVMD
AWGQGTLVTVSS SEQ ID NO: 35 VL for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK

SEQUENCES

SEQ ID NO: 42 HC for Ab7
QVQLVQSGAEVKKPGASVKVSCTVSGRSRTNYHLQWVRQAPGQGLEWMGFIRSSGNT
EYNSEFKSRVTMTRDTSTSTVYMELSSLRSEDTAVYYCARNRWYHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 43 HC DNA for Ab7
CAAGTGCAGCTGGTGCAGTCCGGTGCCGAAGTCAAGAAGCCCGGTGCTTCGGTGAA
AGTGTCATGTACCGTGTCCGGACGCTCCAGGACGAACTACCATCTCCAATGGGTCAG
ACAGGCGCCTGGACAGGGACTGGAATGGATGGGCTTCATCCGGTCCTCGGGGAATA
CCGAGTACAACAGCGAATTCAAGTCCCGCGTGACCATGACTCGGGACACCAGCACC
TCAACCGTGTACATGGAGCTTAGCAGCCTGCGCTCTGAGGACACTGCCGTGTACTAC
TGCGCCCGGAACAGATGGTACCACGGGACCTACTACTCGCCGGGCTATTACGTGAT
GGATGCATGGGGACAGGGCACTCTGGTCACTGTGTCCTCCGCTAGCACCAAGGGCC
CATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT
TCCTCTATTCCAAGCTCACCGTGGACAAGAGCAGGTGGCAGCAGGGGAACGTCTTCT
CATGCTCCGTGATGCATGAGGCTCTGCACAACCACTACACGCAGAAAAGCCTCTCCC
TGTCTCCGGGCAAA SEQ ID NO: 39 LC DNA for Ab6, Ab7, Ab8, Ab9, Ab10, Ab11, Ab12, Ab13, Ab14, Ab15,
Ab16, Ab17, Ab18, and Ab19
GAGATCGTCCTCACCCAGTCTCCCGGCACATTGAGTTTGAGTCCAGGTGAAAGAGCA
ACACTGAGCTGCAAAGGTAGCCAGAACATCGAGAATTATCTTGCATGGTACCAGCAG
GAAACCTGGGCAGGCACCCAGGCTCTTGATCTACAATAGGCATAACCTGCAGACAG
GCATTCCTGATAGATTTTCTGGATCAGGTAGTGGTACCGACTTTACCCTTACCATCTC
ACGACTGGAGCCTGAAGATTTTGCCGTCTATTACTGTTATCAATACAGCGATGGTTA
CACTTTCGGGGAGGGACAAAAGTGGAAATAAAGCGAACTGTGGCTGCACCATCTG
TCTTCATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGATAACG
CCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTT
CAACAGGGGAGAGTGC

Ab8

SEQ ID NO: 30 HCDR1 for Ab6, Ab8, Ab11, Ab13, Ab14, Ab15, Ab19, Ab20, and Ab21
TVSGRSLTNYHLQ SEQ ID NO: 44 HCDR2 for Ab8
FIRSSGNTIYNSEFKS SEQ ID NO: 32 HCDR3 for Ab6, Ab7, Ab8, Ab9, Ab10, Ab12, Ab16, Ab17, Ab18, and
Ab19
ARNRWYHGTYYSPGYYVMDA SEQ ID NO: 33 LCDR1 for Ab6, Ab7, Ab8, Ab9, Ab10, Ab11, Ab12, Ab13, Ab14, Ab15,
Ab16, Ab17, Ab18, and Ab19
KGSQNIENYLA

| SEQUENCES |
| --- |
| SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21<br>YNRHNLQT<br><br>SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21<br>YQYSDGYT<br><br>SEQ ID NO: 45 VH for Ab8<br>QVQLVQSGAEVKKPGASVKVSCTVSGRSLTNYHLQWVRQAPGQGLEWMGFIRSSGNTI<br>YNSEFKSRVTMTRDTSTSTVYMELSSLRSEDTAVYYCARNRWYHGTYYSPGYYVMDA<br>WGQGTLVTVSS<br><br>SEQ ID NO: 35 VL for Ab6, Ab7, Ab8, Ab9, Ab10, Ab11, Ab12, Ab13, Ab14, Ab15, Ab16, Ab17, Ab18, and Ab19<br>EIVLTQSPGTLSLSPGERATLSCKGSQNIENYLAWYQQKPGQAPRLLIYNRHNLQTGIPD<br>RFSGSGSGTDFTLTISRLEPEDFAVYYCYQYSDGYTFGGGTKVEIK<br><br>SEQ ID NO: 46 HC for Ab8<br>QVQLVQSGAEVKKPGASVKVSCTVSGRSLTNYHLQWVRQAPGQGLEWMGFIRSSGNTI<br>YNSEFKSRVTMTRDTSTSTVYMELSSLRSEDTAVYYCARNRWYHGTYYSPGYYVMDA<br>WGQGTLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKRVEPKSCDKTHT<br>CPPCPAPEAEGAPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPSSIEKTISKAKGQ<br>PREPQVYTLPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK<br><br>SEQ ID NO: 37 LC for Ab6, Ab7, Ab8, Ab9, Ab10, Ab11, Ab12, Ab13, Ab14, Ab15, Ab16, Ab17, Ab18, and Ab19<br>EIVLTQSPGTLSLSPGERATLSCKGSQNIENYLAWYQQKPGQAPRLLIYNRHNLQTGIPD<br>RFSGSGSGTDFTLTISRLEPEDFAVYYCYQYSDGYTFGGGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC<br><br>SEQ ID NO: 47 HC DNA for Ab8<br>CAAGTGCAGCTGGTGCAGTCCGGTGCCGAAGTCAAGAAGCCCGGTGCTTCGGTGAA<br>AGTGTCATGTACCGTGTCCGGACGCTCCTTGACGAACTACCATCTCCAATGGGTCAG<br>ACAGGCGCCTGGACAGGGACTGGAATGGATGGGCTTCATCCGGTCCTCGGGGAATA<br>CCATCTACAACAGCGAATTCAAGTCCCGCGTGACCATGACTCGGGACACCAGCACC<br>TCAACCGTGTACATGGAGCTTAGCAGCCTGCGCTCTGAGGACACTGCCGTGTACTAC<br>TGCGCCCGGAACAGATGGTACCACGGGACCTACTACTCGCCGGGCTATTACGTGAT<br>GGATGCATGGGGACAGGGCACTCTGGTCACTGTGTCCTCCGCTAGCACCAAGGGCC<br>CATCGGTCTTCCCCCTGGCACCCTCCTCCAAGAGCACCTCTGGGGGCACAGCGGCCC<br>TGGGCTGCCTGGTCAAGGACTACTTCCCCGAACCGGTGACGGTGTCGTGGAACTCAG<br>GCGCACTGACCAGCGGCGTGCACACCTTCCCGGCTGTCCTACAGTCCTCAGGACTCT<br>ACTCCCTCAGCAGCGTGGTGACCGTGCCCTCCAGCAGCTTGGGCACCCAGACCTACA<br>TCTGCAACGTGAATCACAAGCCCAGCAACACCAAGGTGGACAAGAGAGTTGAGCCC<br>AAATCTTGTGACAAAACTCACACATGCCCACCGTGCCCAGCACCTGAAGCCGAGGG<br>GGCACCGTCAGTCTTCCTCTTCCCCCCAAAACCCAAGGACACCCTCATGATCTCCCG<br>GACCCCTGAGGTCACATGCGTGGTGGTGGACGTGAGCCACGAAGACCCTGAGGTCA<br>AGTTCAACTGGTATGTGGACGGCGTGGAGGTGCATAATGCCAAGACAAAGCCGCGG<br>GAGGAGCAGTACAACAGCACGTACCGTGTGGTCAGCGTCCTCACCGTCCTGCACCA<br>AGACTGGCTGAATGGCAAGGAGTACAAGTGCAAGGTTTCCAACAAAGCCCTCCCAT<br>CCTCCATCGAGAAAACCATCTCCAAAGCCAAAGGGCAGCCCCGAGAACCACAGGTG<br>TACACCCTGCCCCCATCCCGGGAGGAGATGACCAAGAACCAAGTCAGCCTGACCTG<br>CCTGGTCAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGCTCCTTCT<br>TCCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA<br><br>SEQ ID NO: 39 LC DNA for Ab6, Ab7, Ab8, Ab9, Ab10, Ab11, Ab12, Ab13, Ab14, Ab15, Ab16, Ab17, Ab18, and Ab19<br>GAGATCGTCCTCACCCAGTCTCCCGGCACATTGAGTTTGAGTCCAGGTGAAAGAGCA<br>ACACTGAGCTGCAAAGGTAGCCAGAACATCGAGAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |

-continued

| SEQUENCES |
|---|
| Ab9 |

SEQ ID NO: 48 HCDR1 for Ab9
TVSGRSLTNYHIQ

SEQ ID NO: 2 HCDR2 for Ab1, Ab2, Ab3, Ab4, Ab5, Ab7, Ab9, Ab10, Ab11, Ab12, Ab13,
Ab14, Ab15, Ab16, Ab17, Ab18, Ab20, and Ab21
FIRSSGNTEYNSEFKS SEQ ID NO: 32 HCDR3 for Ab6, Ab7, Ab8, Ab9, Ab10, Ab12, Ab16, Ab17, Ab18, and
Ab19
ARNRWYHGTYYSPGYYVMDA SEQ ID NO: 33 LCDR1 for Ab6, Ab7, Ab8, Ab9, Ab10, Ab11, Ab12, Ab13, Ab14, Ab15,
Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YQYSDGYT SEQ ID NO: 49 VH for Ab9
QVQLVQSGAEVKKPGASVKVSCTVSGRSLTNYHIQWVRQAPGQGLEWMGFIRSSGNTE
YNSEFKSRVTMTRDTSTSTVYMELSSLRSEDTAVYYCARNRWYHGTYYSPGYYVMDA
WGQGTLVTVSS SEQ ID NO: 35 VL for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 50 HC for Ab9
QVQLVQSGAEVKKPGASVKVSCTVSGRSLTNYHIQWVRQAPGQGLEWMGFIRSSGNTE
YNSEFKSRVTMTRDTSTSTVYMELSSLRSEDTAVYYCARNRWYHGTYYSPGYYVMDA
WGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHT
CPPCPAPEAEGAPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPSSIEKTISKAKGQ
PREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 51 HC DNA for Ab9
CAAGTGCAGCTGGTGCAGTCCGGTGCCGAAGTCAAGAAGCCCGGTGCTTCGGTGAA
AGTGTCATGTACCGTGTCCGGACGCTCCCTCACGAACTACCATATTCAATGGGTCAG
ACAGGCGCCTGGACAGGGACTGGAATGGATGGGCTTCATCCGGTCCTCGGGGAATA
CCGAGTACAACAGCGAATTCAAGTCCCGCGTGACCATGACTCGGGACACCAGCACC
TCAACCGTGTACATGGAGCTTAGCAGCCTGCGCTCTGAGGACACTGCCGTGTACTAC
TGCGCCCGGAACAGATGGTACCACGGGACCTACTACTCGCCGGGCTATTACGTGAT
GGATGCATGGGGACAGGGCACTCTGGTCACTGTGTCCTCCGCTAGCACCAAGGGCC
CATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT

| SEQUENCES |
|---|
| TCCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA<br><br>SEQ ID NO: 39 LC DNA for Ab6, Ab7, Ab8, Ab9, Ab10, Ab11, Ab12, Ab13, Ab14, Ab15,<br>Ab16, Ab17, Ab18, and Ab19<br>GAGATCGTCCTCACCCAGTCTCCCGGCACATTGAGTTTGAGTCCAGGTGAAAGAGCA<br>ACACTGAGCTGCAAAGGTAGCCAGAACATCGAGAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |

| Ab10 |
|---|
| SEQ ID NO: 52 HCDR1 for Ab10<br>TVSGRSLTGYHLQ<br><br>SEQ ID NO: 2 HCDR2 for Ab1, Ab2, Ab3, Ab4, Ab5, Ab7, Ab9, Ab10, Ab11, Ab12, Ab13,<br>Ab14, Ab15, Ab16, Ab17, Ab18, Ab20, and Ab21<br>FIRSSGNTEYNSEFKS<br><br>SEQ ID NO: 32 HCDR3 for Ab6, Ab7, Ab8, Ab9, Ab10, Ab12, Ab16, Ab17, Ab18, and<br>Ab19<br>ARNRWYHGTYYSPGYYVMDA<br><br>SEQ ID NO: 33 LCDR1 for Ab6, Ab7, Ab8, Ab9, Ab10, Ab11, Ab12, Ab13, Ab14, Ab15,<br>Ab16, Ab17, Ab18, and Ab19<br>KGSQNIENYLA<br><br>SEQ ID NO: 5 LCDR2 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YNRHNLQT<br><br>SEQ ID NO: 6 LCDR3 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YQYSDGYT<br><br>SEQ ID NO: 53 VH for Ab10<br>QVQLVQSGAEVKKPGASVKVSCTVSGRSLTGYHLQWVRQAPGQGLEWMGFIRSSGNT<br>EYNSEFKSRVTMTRDTSTSTVYMELSSLRSEDTAVYYCARNRWYHGTYYSPGYYVMD<br>AWGQGTLVTVSS<br><br>SEQ ID NO: 35 VL for Ab6, Ab7, Ab8, Ab9, Ab10, Ab11, Ab12, Ab13, Ab14, Ab15, Ab16,<br>Ab17, Ab18, and Ab19<br>EIVLTQSPGTLSLSPGERATLSCKGSQNIENYLAWYQQKPGQAPRLLIYNRHNLQTGIPD<br>RFSGSGSGTDFTLTISRLEPEDFAVYYCYQYSDGYTFGGGTKVEIK<br><br>SEQ ID NO: 54 HC for Ab10<br>QVQLVQSGAEVKKPGASVKVSCTVSGRSLTGYHLQWVRQAPGQGLEWMGFIRSSGNT<br>EYNSEFKSRVTMTRDTSTSTVYMELSSLRSEDTAVYYCARNRWYHGTYYSPGYYVMD<br>AWGQGTLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKRVEPKSCDKTH<br>TCPPCPAPEAEGAPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPSSIEKTISKAKG<br>QPREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK<br><br>SEQ ID NO: 37 LC for Ab6, Ab7, Ab8, Ab9, Ab10, Ab11, Ab12, Ab13, Ab14, Ab15, Ab16,<br>Ab17, Ab18, and Ab19<br>EIVLTQSPGTLSLSPGERATLSCKGSQNIENYLAWYQQKPGQAPRLLIYNRHNLQTGIPD<br>RFSGSGSGTDFTLTISRLEPEDFAVYYCYQYSDGYTFGGGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC<br><br>SEQ ID NO: 55 HC DNA for Ab10<br>CAAGTGCAGCTGGTGCAGTCCGGTGCCGAAGTCAAGAAGCCCGGTGCTTCGGTGAA<br>AGTGTCATGTACCGTGTCCGGACGCTCCTTGACGGGCTACCATCTCCAATGGGTCAG<br>ACAGGCGCCTGGACAGGGACTGGAATGGATGGGCTTCATCCGGTCCTCGGGGAATA<br>CCGAGTACAACAGCGAATTCAAGTCCCGCGTGACCATGACTCGGGACACCAGCACC<br>TCAACCGTGTACATGGAGCTTAGCAGCCTGCGCTCTGAGGACACTGCCGTGTACTAC |

SEQUENCES

TGCGCCCGGAACAGATGGTACCACGGGACCTACTACTCGCCGGGCTATTACGTGAT
GGATGCATGGGACAGGGCACTCTGGTCACTGTGTCCTCCGCTAGCACCAAGGGCC
CATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT
TCCTCTATTCCAAGCTCACCGTGGACAAGAGCAGGTGGCAGCAGGGGAACGTCTTCT
CATGCTCCGTGATGCATGAGGCTCTGCACAACCACTACACGCAGAAAAGCCTCTCCC
TGTCTCCGGGCAAA

SEQ ID NO: 39 LC DNA for Ab6, Ab7, Ab8, Ab9, Ab10, Ab11, Ab12, Ab13, Ab14, Ab15, Ab16, Ab17, Ab18, and Ab19
GAGATCGTCCTCACCCAGTCTCCCGGCACATTGAGTTTGAGTCCAGGTGAAAGAGCA
ACACTGAGCTGCAAAGGTAGCCAGAACATCGAGAATTATCTTGCATGGTACCAGCA
GAAACCTGGGCAGGCACCCAGGCTCTTGATCTACAATAGGCATAACCTGCAGACAG
GCATTCCTGATAGATTTTCTGGATCAGGTAGTGGTACCGACTTTACCCTTACCATCTC
ACGACTGGAGCCTGAAGATTTTGCCGTCTATTACTGTTATCAATACAGCGATGGTTA
CACTTTCGGGGGAGGGACAAAAGTGGAAATAAAGCGAACTGTGGCTGCACCATCTG
TCTTCATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGATAACG
CCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTT
CAACAGGGGAGAGTGC

Ab11

SEQ ID NO: 30 HCDR1 for Ab6, Ab8, Ab11, Ab13, Ab14, Ab15, Ab19, Ab20, and Ab21
TVSGRSLTNYHLQ SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS SEQ ID NO: 56 HCDR3 for Ab11
ARNRWHHGTYYSPGYYVMDA SEQ ID NO: 33 LCDR1 for Ab6, Ab7, Ab8, Ab9, Ab10, Ab11, Ab12, Ab13, Ab14, Ab15, Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YQYSDGYT SEQ ID NO: 57 VH for Ab11
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNRWHHGTYYSPGYYVMD
AWGQGTLVTVSS SEQ ID NO: 35 VL for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 58 HC for Ab11
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNRWHHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG

| SEQUENCES |
|---|
| QPREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK<br><br>SEQ ID NO: 37 LC for Ab6, Ab7, Ab8, Ab9, Ab10, Ab11, Ab12, Ab13, Ab14, Ab15, Ab16,<br>Ab17, Ab18, and Ab19<br>EIVLTQSPGTLSLSPGERATLSCKGSQNIENYLAWYQQKPGQAPRLLIYNRHNLQTGIPD<br>RFSGSGSGTDFTLTISRLEPEDFAVYYCYQYSDGYTFGGGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC<br><br>SEQ ID NO: 59 HC DNA for Ab11<br>CAAGTGCAGCTGGTGCAGTCCGGTGCCGAAGTCAAGAAGCCCGGTGCTTCGGTGAA<br>AGTGTCATGTACCGTGTCCGGACGCTCCTTGACGAACTACCATCTCCAATGGGTCAG<br>ACAGGCGCCTGGACAGGGACTGGAATGGATGGGCTTCATCCGGTCCTCGGGGAATA<br>CCGAGTACAACAGCGAATTCAAGTCCCGCGTGACCATGACTCGGGACACCAGCACC<br>TCAACCGTGTACATGGAGCTTAGCAGCCTGCGCTCTGAGGACACTGCCGTGTACTAC<br>TGCGCCCGGAACAGATGGCACCACGGGACCTACTACTCGCCGGGCTATTACGTGAT<br>GGATGCATGGGGACAGGGCACTCTGGTCACTGTGTCCTCCGCTAGCACCAAGGGCC<br>CATCGGTCTTCCCCCTGGCACCCTCCTCCAAGAGCACCTCTGGGGGCACAGCGGCCC<br>TGGGCTGCCTGGTCAAGGACTACTTCCCCGAACCGGTGACGGTGTCGTGGAACTCAG<br>GCGCACTGACCAGCGGCGTGCACACCTTCCCGGCTGTCCTACAGTCCTCAGGACTCT<br>ACTCCCTCAGCAGCGTGGTGACCGTGCCCTCCAGCAGCTTGGGCACCCAGACCTACA<br>TCTGCAACGTGAATCACAAGCCCAGCAACACCAAGGTGGACAAGAGAGTTGAGCCC<br>AAATCTTGTGACAAAACTCACACATGCCCACCGTGCCCAGCACCTGAAGCCGAGGG<br>GGCACCGTCAGTCTTCCTCTTCCCCCCAAAACCCAAGGACACCCTCATGATCTCCCG<br>GACCCCTGAGGTCACATGCGTGGTGGTGGACGTGAGCCACGAAGACCCTGAGGTCA<br>AGTTCAACTGGTATGTGGACGGCGTGGAGGTGCATAATGCCAAGACAAAGCCGCGG<br>GAGGAGCAGTACAACAGCACGTACCGTGTGGTCAGCGTCCTCACCGTCCTGCACCA<br>AGACTGGCTGAATGGCAAGGAGTACAAGTGCAAGGTTTCCAACAAAGCCCTCCCAT<br>CCTCCATCGAGAAAACCATCTCCAAAGCCAAAGGGCAGCCCCGAGAACCACAGGTG<br>TACACCCTGCCCCCATCCCGGGAGGAGATGACCAAGAACCAAGTCAGCCTGACCTG<br>CCTGGTCAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGCTCCTTCT<br>TCCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA<br><br>SEQ ID NO: 39 LC DNA for Ab6, Ab7, Ab8, Ab9, Ab10, Ab11, Ab12, Ab13, Ab14, Ab15,<br>Ab16, Ab17, Ab18, and Ab19<br>GAGATCGTCCTCACCCAGTCTCCCGGCACATTGAGTTTGAGTCCAGGTGAAAGAGCA<br>ACACTGAGCTGCAAAGGTAGCCAGAACATCGAGAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |
| Ab12 |
| SEQ ID NO: 60 HCDR1 for Ab12<br>TVSGRSLTNYHLV<br><br>SEQ ID NO: 2 HCDR2 for Ab1, Ab2, Ab3, Ab4, Ab5, Ab7, Ab9, Ab10, Ab11, Ab12, Ab13,<br>Ab14, Ab15, Ab16, Ab17, Ab18, Ab20, and Ab21<br>FIRSSGNTEYNSEFKS<br><br>SEQ ID NO: 32 HCDR3 for Ab6, Ab7, Ab8, Ab9, Ab10, Ab12, Ab16, Ab17, Ab18, and<br>Ab19<br>ARNRWYHGTYYSPGYYVMDA<br><br>SEQ ID NO: 33 LCDR1 for Ab6, Ab7, Ab8, Ab9, Ab10, Ab11, Ab12, Ab13, Ab14, Ab15,<br>Ab16, Ab17, Ab18, and Ab19<br>KGSQNIENYLA<br><br>SEQ ID NO: 5 LCDR2 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YNRHNLQT<br><br>SEQ ID NO: 6 LCDR3 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YQYSDGYT |

-continued

SEQUENCES

SEQ ID NO: 61 VH for Ab12
QVQLVQSGAEVKKPGASVKVSCTVSGRSLTNYHLVWVRQAPGQGLEWMGFIRSSGNT
EYNSEFKSRVTMTRDTSTSTVYMELSSLRSEDTAVYYCARNRWYHGTYYSPGYYVMD
AWGQGTLVTVSS SEQ ID NO: 35 VL for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 62 HC for Ab12
QVQLVQSGAEVKKPGASVKVSCTVSGRSLTNYHLVWVRQAPGQGLEWMGFIRSSGNT
EYNSEFKSRVTMTRDTSTSTVYMELSSLRSEDTAVYYCARNRWYHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 63 HC DNA for Ab12
CAAGTGCAGCTGGTGCAGTCCGGTGCCGAAGTCAAGAAGCCCGGTGCTTCGGTGAA
AGTGTCATGTACCGTGTCCGGACGCTCCTTGACGAACTACCATCTCGTCTGGGTCAG
ACAGGCGCCTGGACAGGGACTGGAATGGATGGGCTTCATCCGGTCCTCGGGGAATA
CCGAGTACAACAGCGAATTCAAGTCCCGCGTGACCATGACTCGGGACACCAGCACC
TCAACCGTGTACATGGAGCTTAGCAGCCTGCGCTCTGAGGACACTGCCGTGTACTAC
TGCGCCCGGAACAGATGGTACCACGGGACCTACTACTCGCCGGGCTATTACGTGAT
GGATGCATGGGGACAGGGCACTCTGGTCACTGTGTCCTCCGCTAGCACCAAGGGCC
CATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT
TCCTCTATTCCAAGCTCACCGTGGACAAGAGCAGGTGGCAGCAGGGGAACGTCTTCT
CATGCTCCGTGATGCATGAGGCTCTGCACAACCACTACACGCAGAAAAGCCTCTCCC
TGTCTCCGGGCAAA SEQ ID NO: 39 LC DNA for Ab6, Ab7, Ab8, Ab9, Ab10, Ab11, Ab12, Ab13, Ab14, Ab15, Ab16, Ab17, Ab18, and Ab19
GAGATCGTCCTCACCCAGTCTCCCGGCACATTGAGTTTGAGTCCAGGTGAAAGAGCA
ACACTGAGCTGCAAAGGTAGCCAGAACATCGAGAATTATCTTGCATGGTACCAGCA
GAAACCTGGGCAGGCACCCAGGCTCTTGATCTACAATAGGCATAACCTGCAGACAG
GCATTCCTGATAGATTTTCTGGATCAGGTAGTGGTACCGACTTTACCCTTACCATCTC
ACGACTGGAGCCTGAAGATTTTGCCGTCTATTACTGTTATCAATACAGCGATGGTTA
CACTTTCGGGGGAGGGACAAAAGTGGAAATAAAGCGAACTGTGGCTGCACCATCTG
TCTTCATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGATAACG
CCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTT
CAACAGGGGAGAGTGC

Ab13

SEQ ID NO: 30 HCDR1 for Ab6, Ab8, Ab11, Ab13, Ab14, Ab15, Ab19, Ab20, and Ab21
TVSGRSLTNYHLQ SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS -continued

SEQUENCES

SEQ ID NO: 64 HCDR3 for Ab13
ARNRWRHGTYYSPGYYVMDA

SEQ ID NO: 33 LCDR1 for Ab6, Ab7, Ab8, Ab9, Ab10, Ab11, Ab12, Ab13, Ab14, Ab15,
Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YQYSDGYT SEQ ID NO: 65 VH for Ab13
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNRWRHGTYYSPGYYVMD
AWGQGTLVTVSS SEQ ID NO: 35 VL for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 66 HC for Ab13
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNRWRHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 67 HC DNA for Ab13
CAAGTGCAGCTGGTGCAGTCCGGTGCCGAAGTCAAGAAGCCCGGTGCTTCGGTGAA
AGTGTCATGTACCGTGTCCGGACGCTCCTTGACGAACTACCATCTCCAATGGGTCAG
ACAGGCGCCTGGACAGGGACTGGAATGGATGGGCTTCATCCGGTCCTCGGGGAATA
CCGAGTACAACAGCGAATTCAAGTCCCGCGTGACCATGACTCGGGACACCAGCACC
TCAACCGTGTACATGGAGCTTAGCAGCCTGCGCTCTGAGGACACTGCCGTGTACTAC
TGCGCCCGGAACAGATGGCGGCACGGGACCTACTACTCGCCGGGCTATTACGTGAT
GGATGCATGGGGACAGGGCACTCTGGTCACTGTGTCCTCCGCTAGCACCAAGGGCC
CATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT
TCCTCTATTCCAAGCTCACCGTGGACAAGAGCAGGTGGCAGCAGGGGAACGTCTTCT
CATGCTCCGTGATGCATGAGGCTCTGCACAACCACTACACGCAGAAAAGCCTCTCCC
TGTCTCCGGGCAAA SEQ ID NO: 39 LC DNA for Ab6, Ab7, Ab8, Ab9, Ab10, Ab11, Ab12, Ab13, Ab14, Ab15,
Ab16, Ab17, Ab18, and Ab19
GAGATCGTCCTCACCCAGTCTCCCGGCACATTGAGTTTGAGTCCAGGTGAAAGAGCA
ACACTGAGCTGCAAAGGTAGCCAGAACATCGAGAATTATCTTGCATGGTACCAGCA
GAAACCTGGGCAGGCACCCAGGCTCTTGATCTACAATAGGCATAACCTGCAGACAG
GCATTCCTGATAGATTTTCTGGATCAGGTAGTGGTACCGACTTTACCCTTACCATCTC
ACGACTGGAGCCTGAAGATTTTGCCGTCTATTACTGTTATCAATACAGCGATGGTTA

| SEQUENCES |
|---|
| CACTTTCGGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |
| Ab14 |

SEQ ID NO: 30 HCDR1 for Ab6, Ab8, Ab11, Ab13, Ab14, Ab15, Ab19, Ab20, and Ab21
TVSGRSLTNYHLQ SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS SEQ ID NO: 68 HCDR3 for Ab14 and Ab21
ARNRWYHGTYYSPGYYVMDP SEQ ID NO: 33 LCDR1 for Ab6, Ab7, Ab8, Ab9, Ab10, Ab11, Ab12, Ab13, Ab14, Ab15, Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YQYSDGYT SEQ ID NO: 69 VH for Ab14 and Ab21
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNRWYHGTYYSPGYYVMD
PWGQGTLVTVSS SEQ ID NO: 35 VL for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 70 HC for Ab14 and Ab21
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNRWYHGTYYSPGYYVMD
PWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 71 HC DNA for Ab14 and Ab21
CAAGTGCAGCTGGTGCAGTCCGGTGCCGAAGTCAAGAAGCCCGGTGCTTCGGTGAA
AGTGTCATGTACCGTGTCCGGACGCTCCTTGACGAACTACCATCTCCAATGGGTCAG
ACAGGCGCCTGGACAGGGACTGGAATGGATGGGCTTCATCCGGTCCTCGGGGAATA
CCGAGTACAACAGCGAATTCAAGTCCCGCGTGACCATGACTCGGGACACCAGCACC
TCAACCGTGTACATGGAGCTTAGCAGCCTGCGCTCTGAGGACACTGCCGTGTACTAC
TGCGCCCGGAACAGATGGTACCACGGGACCTACTACTCGCCGGGCTATTACGTGAT
GGATCCATGGGGACAGGGCACTCTGGTCACTGTGTCCTCCGCTAGCACCAAGGGCC
CATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA

| SEQUENCES |
|---|
| AGACTGGCTGAATGGCAAGGAGTACAAGTGCAAGGTTTCCAACAAAGCCCTCCCAT<br>CCTCCATCGAGAAAACCATCTCCAAAGCCAAAGGGCAGCCCCGAGAACCACAGGTG<br>TACACCCTGCCCCCATCCCGGGAGGAGATGACCAAGAACCAAGTCAGCCTGACCTG<br>CCTGGTCAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGCTCCTTCT<br>TCCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA<br><br>SEQ ID NO: 39 LC DNA for Ab6, Ab7, Ab8, Ab9, Ab10, Ab11, Ab12, Ab13, Ab14, Ab15,<br>Ab16, Ab17, Ab18, and Ab19<br>GAGATCGTCCTCACCCAGTCTCCCGGCACATTGAGTTTGAGTCCAGGTGAAAGAGCA<br>ACACTGAGCTGCAAAGGTAGCCAGAACATCGAGAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGGACAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |

| Ab15 |
|---|

SEQ ID NO: 30 HCDR1 for Ab6, Ab8, Ab11, Ab13, Ab14, Ab15, Ab19, Ab20, and Ab21
TVSGRSLTNYHLQ SEQ ID NO: 2 HCDR2 for Ab1, Ab2, Ab3, Ab4, Ab5, Ab7, Ab9, Ab10, Ab11, Ab12, Ab13,
Ab14, Ab15, Ab16, Ab17, Ab18, Ab20, and Ab21
FIRSSGNTEYNSEFKS SEQ ID NO: 72 HCDR3 for Ab15 and Ab20
ARNLWYHGTYYSPGYYVMDA SEQ ID NO: 33 LCDR1 for Ab6, Ab7, Ab8, Ab9, Ab10, Ab11, Ab12, Ab13, Ab14, Ab15,
Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YQYSDGYT SEQ ID NO: 73 VH for Ab15 and Ab20
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNLWYHGTYYSPGYYVMD
AWGQGTLVTVSS SEQ ID NO: 35 VL for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 74 HC for Ab15 and Ab20
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNLWYHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC

| SEQUENCES |
|---|
| SEQ ID NO: 75 HC DNA for Ab15 and Ab20<br>CAAGTGCAGCTGGTGCAGTCCGGTGCCGAAGTCAAGAAGCCCGGTGCTTCGGTGAA<br>AGTGTCATGTACCGTGTCCGGACGCTCCTTGACGAACTACCATCTCCAATGGGTCAG<br>ACAGGCGCCTGGACAGGGACTGGAATGGATGGGCTTCATCCGGTCCTCGGGGAATA<br>CCGAGTACAACAGCGAATTCAAGTCCCGCGTGACCATGACTCGGGACACCAGCACC<br>TCAACCGTGTACATGGAGCTTAGCAGCCTGCGCTCTGAGGACACTGCCGTGTACTAC<br>TGCGCCCGGAACCTCTGGTACCACGGGACCTACTACTCGCCGGGCTATTACGTGATG<br>GATGCATGGGGACAGGGCACTCTGGTCACTGTGTCCTCCGCTAGCACCAAGGGCCC<br>ATCGGTCTTCCCCCTGGCACCCTCCTCCAAGAGCACCTCTGGGGGCACAGCGGCCCT<br>GGGCTGCCTGGTCAAGGACTACTTCCCCGAACCGGTGACGGTGTCGTGGAACTCAG<br>GCGCACTGACCAGCGGCGTGCACACCTTCCCGGCTGTCCTACAGTCCTCAGGACTCT<br>ACTCCCTCAGCAGCGTGGTGACCGTGCCCTCCAGCAGCTTGGGCACCCAGACCTACA<br>TCTGCAACGTGAATCACAAGCCCAGCAACACCAAGGTGGACAAGAGAGTTGAGCCC<br>AAATCTTGTGACAAAACTCACACATGCCCACCGTGCCCAGCACCTGAAGCCGAGGG<br>GGCACCGTCAGTCTTCCTCTTCCCCCCAAAACCCAAGGACACCCTCATGATCTCCCG<br>GACCCCTGAGGTCACATGCGTGGTGGTGGACGTGAGCCACGAAGACCCTGAGGTCA<br>AGTTCAACTGGTATGTGGACGGCGTGGAGGTGCATAATGCCAAGACAAAGCCGCGG<br>GAGGAGCAGTACAACAGCACGTACCGTGTGGTCAGCGTCCTCACCGTCCTGCACCA<br>AGACTGGCTGAATGGCAAGGAGTACAAGTGCAAGGTTTCCAACAAAGCCCTCCCAT<br>CCTCCATCGAGAAAACCATCTCCAAAGCCAAAGGGCAGCCCCGAGAACCACAGGTG<br>TACACCCTGCCCCCATCCCGGGAGGAGATGACCAAGAACCAAGTCAGCCTGACCTG<br>CCTGGTCAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGCTCCTTCT<br>TCCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA<br><br>SEQ ID NO: 39 LC DNA for Ab6, Ab7, Ab8, Ab9, Ab10, Ab11, Ab12, Ab13, Ab14, Ab15, Ab16, Ab17, Ab18, and Ab19<br>GAGATCGTCCTCACCCAGTCTCCCGGCACATTGAGTTTGAGTCCAGGTGAAAGAGCA<br>ACACTGAGCTGCAAAGGTAGCCAGAACATCGAGAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |

| Ab16 |
|---|

SEQ ID NO: 76 HCDR1 for Ab16
TRSGRSLTNYHLQ

SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS SEQ ID NO: 32 HCDR3 for Ab6, Ab7, Ab8, Ab9, Ab10, Ab12, Ab16, Ab17, Ab18, and Ab19
ARNRWYHGTYYSPGYYVMDA SEQ ID NO: 33 LCDR1 for Ab6, Ab7, Ab8, Ab9, Ab10, Ab11, Ab12, Ab13, Ab14, Ab15, Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YQYSDGYT SEQ ID NO: 77 VH for Ab16
QVQLVQSGAEVKKPGASVKVSCTRSGRSLTNYHLQWVRQAPGQGLEWMGFIRSSGNT
EYNSEFKSRVTMTRDTSTSTVYMELSSLRSEDTAVYYCARNRWYHGTYYSPGYYVMD
AWGQGTLVTVSS SEQ ID NO: 35 VL for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK

| SEQUENCES |
| --- |

SEQ ID NO: 78 HC for Ab16
QVQLVQSGAEVKKPGASVKVSCTRSGRSLTNYHLQWVRQAPGQGLEWMGFIRSSGNT
EYNSEFKSRVTMTRDTSTSTVYMELSSLRSEDTAVYYCARNRWYHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16, Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 79 HC DNA for Ab16
CAAGTGCAGCTGGTGCAGTCTGGTGCAGAAGTCAAGAAGCCGGGCGCTTCAGTGAA
AGTGTCCTGCACTCGGTCGGGACGGTCCTTGACGAACTACCATCTTCAATGGGTCAG
ACAGGCCCCCGGTCAAGGACTGGAATGGATGGGGTTCATCCGGTCCTCCGGGAACA
CTGAGTACAACTCCGAGTTCAAGAGCAGAGTGACCATGACTCGCGACACCTCCACC
TCGACCGTGTACATGGAACTGTCAAGCCTGAGGAGCGAGGATACCGCCGTGTACTA
CTGTGCGCGCAATCGCTGGTACCACGGCACCTATTACTCGCCTGGCTACTACGTGAT
GGACGCCTGGGGACAGGGAACCCTCGTGACTGTCAGCTCCGCTAGCACCAAGGGCC
CATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT
TCCTCTATTCCAAGCTCACCGTGGACAAGAGCAGGTGGCAGCAGGGGAACGTCTTCT
CATGCTCCGTGATGCATGAGGCTCTGCACAACCACTACACGCAGAAAAGCCTCTCCC
TGTCTCCGGGCAAA SEQ ID NO: 39 LC DNA for Ab6, Ab7, Ab8, Ab9, Ab10, Ab11, Ab12, Ab13, Ab14, Ab15, Ab16, Ab17, Ab18, and Ab19
GAGATCGTCCTCACCCAGTCTCCCGGCACATTGAGTTTGAGTCCAGGTGAAAGAGCA
ACACTGAGCTGCAAAGGTAGCCAGAACATCGAGAATTATCTTGCATGGTACCAGCA
GAAACCTGGGCAGGCACCCAGGCTCTTGATCTACAATAGGCATAACCTGCAGACAG
GCATTCCTGATAGATTTTCTGGATCAGGTAGTGGTACCGACTTTACCCTTACCATCTC
ACGACTGGAGCCTGAAGATTTTGCCGTCTATTACTGTTATCAATACAGCGATGGTTA
CACTTTCGGGGGAGGGACAAAAGTGGAAATAAAGCGAACTGTGGCTGCACCATCTG
TCTTCATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGATAACG
CCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTT
CAACAGGGGAGAGTGC

| Ab17 |
| --- |

SEQ ID NO: 80 HCDR1 for Ab17
TVSGRSLTNIHLQ

SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS SEQ ID NO: 32 HCDR3 for Ab6, Ab7, Ab8, Ab9, Ab10, Ab12, Ab16, Ab17, Ab18, and Ab19
ARNRWYHGTYYSPGYYVMDA SEQ ID NO: 33 LCDR1 for Ab6, Ab7, Ab8, Ab9, Ab10, Ab11, Ab12, Ab13, Ab14, Ab15, Ab16, Ab17, Ab18, and Ab19
KGSQNIENYLA -continued

SEQUENCES

SEQ ID NO: 5 LCDR2 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YQYSDGYT SEQ ID NO: 81 VH for Ab17
QVQLVQSGAEVKKPGASVKVSCTVSGRSLTNIHLQWVRQAPGQGLEWMGFIRSSGNTE
YNSEFKSRVTMTRDTSTSTVYMELSSLRSEDTAVYYCARNRWYHGTYYSPGYYVMDA
WGQGTLVTVSS SEQ ID NO: 35 VL for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 82 HC for Ab17
QVQLVQSGAEVKKPGASVKVSCTVSGRSLTNIHLQWVRQAPGQGLEWMGFIRSSGNTE
YNSEFKSRVTMTRDTSTSTVYMELSSLRSEDTAVYYCARNRWYHGTYYSPGYYVMDA
WGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHT
CPPCPAPEAEGAPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPSSIEKTISKAKGQ
PREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 83 HC DNA for Ab17
CAAGTGCAGCTGGTGCAGTCGGGAGCAGAAGTCAAGAAGCCTGGAGCCTCAGTGAA
AGTGTCCTGCACCGTCAGCGGTCGGAGCCTGACCAACATCCACCTTCAGTGGGTCAG
ACAGGCTCCCGGACAAGGCCTCGAATGGATGGGCTTCATTCGCTCGTCCGGAAACA
CGGAGTACAACTCTGAGTTCAAGTCCCGCGTGACCATGACTAGGGACACCAGCACC
TCGACCGTGTACATGGAACTGTCCAGCCTGAGATCCGAGGACACTGCCGTGTATTAC
TGTGCGCGGAATCGGTGGTACCATGGGACTTACTACTCCCCGGGCTACTACGTGATG
GATGCCTGGGGTCAAGGGACCCTCGTGACTGTGTCATCCGCTAGCACCAAGGGCCC
ATCGGTCTTCCCCCTGGCACCCTCCTCCAAGAGCACCTCTGGGGGCACAGCGGCCCT
GGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT
TCCTCTATTCCAAGCTCACCGTGGACAAGAGCAGGTGGCAGCAGGGGAACGTCTTCT
CATGCTCCGTGATGCATGAGGCTCTGCACAACCACTACACGCAGAAAAGCCTCTCCC
TGTCTCCGGGCAAA SEQ ID NO: 39 LC DNA for Ab6, Ab7, Ab8, Ab9, Ab10, Ab11, Ab12, Ab13, Ab14, Ab15,
Ab16, Ab17, Ab18, and Ab19
GAGATCGTCCTCACCCAGTCTCCCGGCACATTGAGTTTGAGTCCAGGTGAAAGAGCA
ACACTGAGCTGCAAAGGTAGCCAGAACATCGAGAATTATCTTGCATGGTACCAGCA
GAAACCTGGGCAGGCACCCAGGCTCTTGATCTACAATAGGCATAACCTGCAGACAG
GCATTCCTGATAGATTTTCTGGATCAGGTAGTGGTACCGACTTTACCCTTACCATCTC
ACGACTGGAGCCTGAAGATTTTGCCGTCTATTACTGTTATCAATACAGCGATGGTTA
CACTTTCGGGGGAGGGACAAAAGTGGAAATAAAGCGAACTGTGGCTGCACCATCTG
TCTTCATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGATAACG
CCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTT
CAACAGGGGAGAGTGC -continued

| SEQUENCES |
|---|
| Ab18 |

SEQ ID NO: 84 HCDR1 for Ab18
TVSGRSLTNYHLG

SEQ ID NO: 2 HCDR2 for Ab1, Ab2, Ab3, Ab4, Ab5, Ab7, Ab9, Ab10, Ab11, Ab12, Ab13,
Ab14, Ab15, Ab16, Ab17, Ab18, Ab20, and Ab21
FIRSSGNTEYNSEFKS SEQ ID NO: 32 HCDR3 for Ab6, Ab7, Ab8, Ab9, Ab10, Ab12, Ab16, Ab17, Ab18, and
Ab19
ARNRWYHGTYYSPGYYVMDA SEQ ID NO: 33 LCDR1 for Ab6, Ab7, Ab8, Ab9, Ab10, Ab11, Ab12, Ab13, Ab14, Ab15,
Ab16, Ab17, Ab18, and Ab19
KGSQNIENYLA SEQ ID NO: 5 LCDR2 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11,
Ab12, Ab13, Ab14, Ab15, Ab16, Ab17, Ab18, Ab19, Ab20, and Ab21
YQYSDGYT SEQ ID NO: 85 VH for Ab18
QVQLVQSGAEVKKPGASVKVSCTVSGRSLTNYHLGWVRQAPGQGLEWMGFIRSSGNT
EYNSEFKSRVTMTRDTSTSTVYMELSSLRSEDTAVYYCARNRWYHGTYYSPGYYVMD
AWGQGTLVTVSS SEQ ID NO: 35 VL for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIK SEQ ID NO: 86 HC for Ab18
QVQLVQSGAEVKKPGASVKVSCTVSGRSLTNYHLGWVRQAPGQGLEWMGFIRSSGNT
EYNSEFKSRVTMTRDTSTSTVYMELSSLRSEDTAVYYCARNRWYHGTYYSPGYYVMD
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 37 LC for Ab6, Ab7, Ab8, Ab9, Ab10, Ab11, Ab12, Ab13, Ab14, Ab15, Ab16,
Ab17, Ab18, and Ab19
EIVLTQSPGTLSLSPGERATLSCKGSQNIENYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 87 HC DNA for Ab18
CAAGTGCAGTTGGTGCAGTCCGGTGCCGAAGTCAAGAAGCCGGGAGCTTCCGTGAA
AGTGTCGTGCACTGTGTCCGGTCGGAGCCTGACCAACTACCACCTGGGCTGGGTCAG
ACAGGCACCTGGCCAAGGACTGGAATGGATGGGCTTCATCCGGAGCTCAGGAAACA
CCGAGTACAACTCGGAGTTCAAGTCGCGCGTGACTATGACGCGGGACACTTCAACC
AGCACTGTCTACATGGAACTTAGCTCTCTGAGGTCCGAGGACACCGCCGTGTACTAC
TGTGCCCGCAATAGATGGTACCATGGGACCTACTACTCCCCCGGCTATTACGTGATG
GATGCGTGGGGACAGGGGACCCTCGTGACCGTGTCCTCCGCTAGCACCAAGGGCCC
ATCGGTCTTCCCCCTGGCACCCTCCTCCAAGAGCACCTCTGGGGGCACAGCGGCCCT
GGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT

| SEQUENCES |
|---|
| TCCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA<br><br>SEQ ID NO: 39 LC DNA for Ab6, Ab7, Ab8, Ab9, Ab10, Ab11, Ab12, Ab13, Ab14, Ab15,<br>Ab16, Ab17, Ab18, and Ab19<br>GAGATCGTCCTCACCCAGTCTCCCGGCACATTGAGTTTGAGTCCAGGTGAAAGAGCA<br>ACACTGAGCTGCAAAGGTAGCCAGAACATCGAGAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTTCGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |
| Ab19 |
| SEQ ID NO: 30 HCDR1 for Ab6, Ab8, Ab11, Ab13, Ab14, Ab15, Ab19, Ab20, and Ab21<br>TVSGRSLTNYHLQ<br><br>SEQ ID NO: 88 HCDR2 for Ab19<br>FIRRSGNTEYNSEFKS<br><br>SEQ ID NO: 32 HCDR3 for Ab6, Ab7, Ab8, Ab9, Ab10, Ab12, Ab16, Ab17, Ab18, and<br>Ab19<br>ARNRWYHGTYYSPGYYVMDA<br><br>SEQ ID NO: 33 LCDR1 for Ab6, Ab7, Ab8, Ab9, Ab10, Ab11, Ab12, Ab13, Ab14, Ab15,<br>Ab16, Ab17, Ab18, and Ab19<br>KGSQNIENYLA<br><br>SEQ ID NO: 5 LCDR2 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YNRHNLQT<br><br>SEQ ID NO: 6 LCDR3 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YQYSDGYT<br><br>SEQ ID NO: 89 VH for Ab19<br>QVQLVQSGAEVKKPGASVKVSCTVSGRSLTNYHLQWVRQAPGQGLEWMGFIRRSGNT<br>EYNSEFKSRVTMTRDTSTSTVYMELSSLRSEDTAVYYCARNRWYHGTYYSPGYYVMD<br>AWGQGTLVTVSS<br><br>SEQ ID NO: 35 VL for Ab6, Ab7, Ab8, Ab9, Ab10, Ab11, Ab12, Ab13, Ab14, Ab15, Ab16,<br>Ab17, Ab18, and Ab19<br>EIVLTQSPGTLSLSPGERATLSCKGSQNIENYLAWYQQKPGQAPRLLIYNRHNLQTGIPD<br>RFSGSGSGTDFTLTISRLEPEDFAVYYCYQYSDGYTFGGGTKVEIK<br><br>SEQ ID NO: 90 HC for Ab19<br>QVQLVQSGAEVKKPGASVKVSCTVSGRSLTNYHLQWVRQAPGQGLEWMGFIRRSGNT<br>EYNSEFKSRVTMTRDTSTSTVYMELSSLRSEDTAVYYCARNRWYHGTYYSPGYYVMD<br>AWGQGTLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKRVEPKSCDKTH<br>TCPPCPAPEAEGAPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPSSIEKTISKAKG<br>QPREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK<br><br>SEQ ID NO: 37 LC for Ab6, Ab7, Ab8, Ab9, Ab10, Ab11, Ab12, Ab13, Ab14, Ab15, Ab16,<br>Ab17, Ab18, and Ab19<br>EIVLTQSPGTLSLSPGERATLSCKGSQNIENYLAWYQQKPGQAPRLLIYNRHNLQTGIPD<br>RFSGSGSGTDFTLTISRLEPEDFAVYYCYQYSDGYTFGGGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC<br><br>SEQ ID NO: 91 HC DNA for Ab19<br>CAAGTGCAGCTGGTGCAGTCAGGAGCCGAAGTCAAGAAGCCTGGAGCCTCGGTGAA<br>AGTGTCCTGCACCGTGTCGGGGAGGAGCCTGACCAACTACCATCTTCAATGGGTCCG<br>CCAAGCACCGGGACAGGGTTTGGAGTGGATGGGCTTCATCAGACGCAGCGGCAACA<br>CCGAGTATAACTCTGAATTCAAGTCCAGAGTGACCATGACCCGGGACACTTCCACGT<br>CAACCGTCTACATGGAGCTGTCGTCCCTGCGGTCCGAAGATACTGCTGTGTACTACT<br>GTGCCCGGAATCGCTGGTACCACGGCACTTACTACTCCCCCGGGTACTACGTGATGG |

| SEQUENCES |
|---|
| ACGCGTGGGGACAGGGTACCCTCGTGACTGTGTCCAGCGCTAGCACCAAGGGCCCA<br>TCGGTCTTCCCCCTGGCACCCTCCTCCAAGAGCACCTCTGGGGGCACAGCGGCCCTG<br>GGCTGCCTGGTCAAGGACTACTTCCCCGAACCGGTGACGGTGTCGTGGAACTCAGG<br>CGCACTGACCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAGACCTACAT<br>CTGCAACGTGAATCACAAGCCCAGCAACACCAAGGTGGACAAGAGAGTTGAGCCCA<br>AATCTTGTGACAAAACTCACACATGCCCACCGTGCCCAGCACCTGAAGCCGAGGGG<br>GCACCGTCAGTCTTCCTCTTCCCCCCAAAACCCAAGGACACCCTCATGATCTCCCGG<br>ACCCCTGAGGTCACATGCGTGGTGGTGGACGTGAGCCACGAAGACCCTGAGGTCAA<br>GTTCAACTGGTATGTGGACGGCGTGGAGGTGCATAATGCCAAGACAAAGCCGCGGG<br>AGGAGCAGTACAACAGCACGTACCGTGTGGTCAGCGTCCTCACCGTCCTGCACCAA<br>GACTGGCTGAATGGCAAGGAGTACAAGTGCAAGGTTTCCAACAAAGCCCTCCCATC<br>CTCCATCGAGAAAACCATCTCCAAAGCCAAAGGGCAGCCCCGAGAACCACAGGTGT<br>ACACCCTGCCCCCATCCCGGGAGGAGATGACCAAGAACCAAGTCAGCCTGACCTGC<br>CTGGTCAAAGGCTTCTATCCCAGCGACATCGCCGTGGAGTGGGAGAGCAATGGGCA<br>GCCGGAGAACAACTACAAGACCACGCCTCCCGTGCTGGACTCCGACGGCTCCTTCTT<br>CCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA<br><br>SEQ ID NO: 39 LC DNA for Ab6, Ab7, Ab8, Ab9, Ab10, Ab11, Ab12, Ab13, Ab14, Ab15,<br>Ab16, Ab17, Ab18, and Ab19<br>GAGATCGTCCTCACCCAGTCTCCCGGCACATTGAGTTTGAGTCCAGGTGAAAGAGCA<br>ACACTGAGCTGCAAAGGTAGCCAGAACATCGAGAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGAGGGACAAAAGTGGAAATAAAGCGAACTGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |

| Ab20 |
|---|
| SEQ ID NO: 30 HCDR1 for Ab6, Ab8, Ab11, Ab13, Ab14, Ab15, Ab19, Ab20, and Ab21<br>TVSGRSLTNYHLQ<br><br>SEQ ID NO: 2 HCDR2 for Ab1, Ab2, Ab3, Ab4, Ab5, Ab7, Ab9, Ab10, Ab11, Ab12, Ab13,<br>Ab14, Ab15, Ab16, Ab17, Ab18, Ab20, and Ab21<br>FIRSSGNTEYNSEFKS<br><br>SEQ ID NO: 72 HCDR3 for Ab15 and Ab20<br>ARNLWYHGTYYSPGYYVMDA<br><br>SEQ ID NO: 4 LCDR1 for Ab1, Ab2, Ab3, Ab4, Ab5, Ab20, and Ab21<br>KGSQNINNYLA<br><br>SEQ ID NO: 5 LCDR2 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YNRHNLQT<br><br>SEQ ID NO: 6 LCDR3 for Ab1, Ab2, Ab3, Ab4, Ab5, Ab6, Ab7, Ab8, Ab9, Ab10, Ab11,<br>Ab12, Ab13, Ab14, Ab15, Ab16, Ab17, Ab18, Ab19, Ab20, and Ab21<br>YQYSDGYT<br><br>SEQ ID NO: 73 VH for Ab15 and Ab20<br>QVQLVQSGAEVKKPGASVKVSCTVSGRSLTNYHLQWVRQAPGQGLEWMGFIRSSGNT<br>EYNSEFKSRVTMTRDTSTSTVYMELSSLRSEDTAVYYCARNLWYHGTYYSPGYYVMD<br>AWGQGTLVTVSS<br><br>SEQ ID NO: 8 VL for Ab1, Ab20, and Ab21<br>EIVLTQSPGTLSLSPGERATLSCKGSQNINNYLAWYQQKPGQAPRLLIYNRHNLQTGIPD<br>RFSGSGSGTDFTLTISRLEPEDFAVYYCYQYSDGYTFGGGTKVEIK<br><br>SEQ ID NO: 74 HC for Ab15 and Ab20<br>QVQLVQSGAEVKKPGASVKVSCTVSGRSLTNYHLQWVRQAPGQGLEWMGFIRSSGNT<br>EYNSEFKSRVTMTRDTSTSTVYMELSSLRSEDTAVYYCARNLWYHGTYYSPGYYVMD<br>AWGQGTLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKRVEPKSCDKTH<br>TCPPCPAPEAEGAPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPSSIEKTISKAKG<br>QPREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |

| SEQUENCES |
|---|
| SEQ ID NO: 10 LC for Ab1, Ab20, and Ab21<br>EIVLTQSPGTLSLSPGERATLSCKGSQNINNYLAWYQQKPGQAPRLLIYNRHNLQTGIPD<br>RFSGSGSGTDFTLTISRLEPEDFAVYYCYQYSDGYTFGGGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC<br><br>SEQ ID NO: 75 HC DNA for Ab15 and Ab20<br>CAAGTGCAGCTGGTGCAGTCCGGTGCCGAAGTCAAGAAGCCCGGTGCTTCGGTGAA<br>AGTGTCATGTACCGTGTCCGGACGCTCCTTGACGAACTACCATCTCCAATGGGTCAG<br>ACAGGCGCCTGGACAGGGACTGGAATGGATGGGCTTCATCCGGTCCTCGGGGAATA<br>CCGAGTACAACAGCGAATTCAAGTCCCGCGTGACCATGACTCGGGACACCAGCACC<br>TCAACCGTGTACATGGAGCTTAGCAGCCTGCGCTCTGAGGACACTGCCGTGTACTAC<br>TGCGCCCGGAACCTCTGGTACCACGGGACCTACTACTCGCCGGGCTATTACGTGATG<br>GATGCATGGGGACAGGGCACTCTGGTCACTGTGTCCTCCGCTAGCACCAAGGGCCC<br>ATCGGTCTTCCCCCTGGCACCCTCCTCCAAGAGCACCTCTGGGGGCACAGCGGCCCT<br>GGGCTGCCTGGTCAAGGACTACTTCCCCGAACCGGTGACGGTGTCGTGGAACTCAG<br>GCGCACTGACCAGCGGCGTGCACACCTTCCCGGCTGTCCTACAGTCCTCAGGACTCT<br>ACTCCCTCAGCAGCGTGGTGACCGTGCCCTCCAGCAGCTTGGGCACCCAGACCTACA<br>TCTGCAACGTGAATCACAAGCCCAGCAACACCAAGGTGGACAAGAGAGTTGAGCCC<br>AAATCTTGTGACAAAACTCACACATGCCCACCGTGCCCAGCACCTGAAGCCGAGGG<br>GGCACCGTCAGTCTTCCTCTTCCCCCCAAAACCCAAGGACACCCTCATGATCTCCCG<br>GACCCCTGAGGTCACATGCGTGGTGGTGGACGTGAGCCACGAAGACCCTGAGGTCA<br>AGTTCAACTGGTATGTGGACGGCGTGGAGGTGCATAATGCCAAGACAAAGCCGCGG<br>GAGGAGCAGTACAACAGCACGTACCGTGTGGTCAGCGTCCTCACCGTCCTGCACCA<br>AGACTGGCTGAATGGCAAGGAGTACAAGTGCAAGGTTTCCAACAAAGCCCTCCCAT<br>CCTCCATCGAGAAAACCATCTCCAAAGCCAAAGGGCAGCCCCGAGAACCACAGGTG<br>TACACCCTGCCCCCATCCCGGGAGGAGATGACCAAGAACCAAGTCAGCCTGACCTG<br>CCTGGTCAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGCTCCTTCT<br>TCCTCTATTCCAAGCTCACCGTGGACAAGAGCAGGTGGCAGCAGGGGAACGTCTTCT<br>CATGCTCCGTGATGCATGAGGCTCTGCACAACCACTACACGCAGAAAAGCCTCTCCC<br>TGTCTCCGGGCAAA<br><br>SEQ ID NO: 12 LC DNA for Ab1, Ab20, and Ab21<br>GAGATCGTCCTCACCCAGTCTCCCGGCACATTGAGTTTGAGTCCAGGTGAAAGAGCA<br>ACACTGAGCTGCAAAGGTAGCCAGAACATCAATAATTATCTTGCATGGTACCAGCA<br>GAAACCTGGGCAGGCACCCAGGCTCTTGATCTACAATAGGCATAACCTGCAGACAG<br>GCATTCCTGATAGATTTTCTGGATCAGGTAGTGGTACCGACTTTACCCTTACCATCTC<br>ACGACTGGAGCCTGAAGATTTTGCCGTCTATTACTGTTATCAATACAGCGATGGTTA<br>CACTTTCGGGGAGGGACAAAAGTGGAAATAAAGCGAACCGTGGCTGCACCATCTG<br>TCTTCATCTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGATAACG<br>CCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTT<br>CAACAGGGGAGAGTGC |

Ab21

SEQ ID NO: 30 HCDR1 for Ab6, Ab8, Ab11, Ab13, Ab14, Ab15, Ab19, Ab20, and Ab21
TVSGRSLTNYHLQ SEQ ID NO: 2 HCDR2 for Ab1, Ab2, Ab3, Ab4, Ab5, Ab7, Ab9, Ab10, Ab11, Ab12, Ab13, Ab14, Ab15, Ab16, Ab17, Ab18, Ab20, and Ab21
FIRSSGNTEYNSEFKS SEQ ID NO: 68 HCDR3 for Ab14 and Ab21
ARNRWYHGTYYSPGYYVMDP SEQ ID NO: 4 LCDR1 for Ab1, Ab2, Ab3, Ab4, Ab5, Ab20, and Ab21
KGSQNINNYLA SEQ ID NO: 5 LCDR2 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YNRHNLQT SEQ ID NO: 6 LCDR3 for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21
YQYSDGYT SEQ ID NO: 69 VH for Ab14 and Ab21
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNRWYHGTYYSPGYYVMD
PWGQGTLVTVSS

| SEQUENCES |
| --- |

SEQ ID NO: 8 VL for Ab1, Ab20, and Ab21
EIVLTQSPGTLSLSPGERATLSCKGSQNINNYLAWYQQKPGQAPRLLIYNRHNLQTGIPD
RFSGSGSGTDFTLTISRLEPEDFAVYYCYQYSDGYTFGGGTKVEIK SEQ ID NO: 70 HC for Ab14 and Ab21
QVQLVQSGAEVKKPGASVKVSCTVSGRSLTNYHLQWVRQAPGQGLEWMGFIRSSGNT
EYNSEFKSRVTMTRDTSTSTVYMELSSLRSEDTAVYYCARNRWYHGTYYSPGYYVMD
PWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 10 LC for Ab1, Ab20, and Ab21
EIVLTQSPGTLSLSPGERATLSCKGSQNINNYLAWYQQKPGQAPRLLIYNRHNLQTGIPD
RFSGSGSGTDFTLTISRLEPEDFAVYYCYQYSDGYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC SEQ ID NO: 71 HC DNA for Ab14 and Ab21
CAAGTGCAGCTGGTGCAGTCCGGTGCCGAAGTCAAGAAGCCCGGTGCTTCGGTGAA
AGTGTCATGTACCGTGTCCGGACGCTCCTTGACGAACTACCATCTCCAATGGGTCAG
ACAGGCGCCTGGACAGGGACTGGAATGGATGGGCTTCATCCGGTCCTCGGGGAATA
CCGAGTACAACAGCGAATTCAAGTCCCGCGTGACCATGACTCGGGACACCAGCACC
TCAACCGTGTACATGGAGCTTAGCAGCCTGCGCTCTGAGGACACTGCCGTGTACTAC
TGCGCCCGGAACAGATGGTACCACGGGACCTACTACTCGCCGGGCTATTACGTGAT
GGATCCATGGGACAGGGCACTCTGGTCACTGTGTCCTCCGCTAGCACCAAGGGCC
CATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAG
GCGCACTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGAGGG
GGCACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCA
AGTTCAACTGGTATGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
AGACTGGCTGAATGGCAAGGAGTACAAGTGCAAGGTTTCCAACAAAGCCCTCCCAT
CCTCCATCGAGAAAACCATCTCCAAAGCCAAAGGGCAGCCCCGAGAACCACAGGTG
TACACCCTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCT
TCCTCTATTCCAAGCTCACCGTGGACAAGAGCAGGTGGCAGCAGGGGAACGTCTTCT
CATGCTCCGTGATGCATGAGGCTCTGCACAACCACTACACGCAGAAAAGCCTCTCCC
TGTCTCCGGGCAAA SEQ ID NO: 12 LC DNA for Ab1, Ab20, and Ab21
GAGATCGTCCTCACCCAGTCTCCCGGCACATTGAGTTTGAGTCCAGGTGAAAGAGCA
ACACTGAGCTGCAAAGGTAGCCAGAACATCAATAATTATCTTGCATGGTACCAGCA
GAAACCTGGGCAGGCACCCAGGCTCTTGATCTACAATAGGCATAACCTGCAGACAG
GCATTCCTGATAGATTTTCTGGATCAGGTAGTGGTACCGACTTTACCCTTACCATCTC
ACGACTGGAGCCTGAAGATTTTGCCGTCTATTACTGTTATCAATACAGCGATGGTTA
CACTTTCGGGGAGGGACAAAAGTGGAAATAAAGCGAACCGTGGCTGCACCATCTG
TCTTCATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGATAACG
CCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTT
CAACAGGGGAGAGTGC

| INX444 LALA |
| --- |

SEQ ID NO: 92 HC for INX444 LALA (CDRs bolded, underlined)
QVQLKESGPGLVKPSQTLSLTCTVSGFSLTNYHLQWVRQPPGKGLEWIG**FIRSSGNTE
YNPSLKSRVTISRDTSKNQVSLKLSSVTAADTAVYYCARKRWVHGTWYSPGYYVMD
A**WGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDKTH
TCPPCPAPEAAGGPSVFLFPPKPKDTLMISRTPEVTCVVVDVSHRDPEVKFNWYVDGVE
VHNAKTKPREEQYNSTYRVVSVLTVLHQDWLNGKEYKCAVSNKALPAPIEKTISKAKG
QPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

SEQUENCES

SEQ ID NO: 93 LC for INX444 LALA and INX444 IgG1EN (CDRs bolded, underlined)
DIQLTQSPSAMSASVGDRVTITCRASQGISNYLAWYQQKPGKAPKLLIYAASTLQSGVA
SRFSGRGSGTDFTLTISSLQPEDFATYYCQQSDILPYTFGQGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC

INX444 IgG1EN

SEQ ID NO: 94 HC for INX444 IgG1EN (CDRs bolded, underlined)
QVQLKESGPGLVKPSQTLSLTCTVSGFSLTNYHLQWVRQPPGKGLEWIG**FIRSSGNTE
YNPSLKSRVTISRDTSKNQVSLKLSSVTAADTAVYYCARKRWVHGTWYSPGYYVMD**
AWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTH
TCPPCPAPEAEGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPSSIEKTISKAKG
QPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 93 LC for INX444 LALA and INX444 IgG1EN (CDRs bolded, underlined)
DIQLTQSPSAMSASVGDRVTITCRASQGISNYLAWYQQKPGKAPKLLIYAASTLQSGVA
SRFSGRGSGTDFTLTISSLQPEDFATYYCQQSDILPYTFGQGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC SEQ ID NO: 95 Human MCT1 protein
MPPAVGGPVGYTPPDGGWGWAVVIGAFISIGFSYAFPKSITVFFKEIEGIFHATTSEVSWI
SSIMLAVMYGGGPISSILVNKYGSRIVMIVGGCLSGCGLIAASFCNTVQQLYVCIGVIGGL
GLAFNLNPALTMIGKYFYKRRPLANGLAMAGSPVFLCTLAPLNQVFFGIFGWRGSFLIL
GGLLLNCCVAGALMRPIGPKPTKAGKDKSKASLEKAGKSGVKKDLHDANTDLIGRHPK
QEKRSVFQTINQFLDLTLFTHRGFLLYLSGNVIMFFGLFAPLVFLSSYGKSQHYSSEKSAF
LLSILAFVDMVARPSMGLVANTKPIRPRIQYFFAASVVANGVCHMLAPLSTTYVGFCVY
AGFFGFAFGWLSSVLFETLMDLVGPQRFSSAVGLVTIVECCPVLLGPPLLGRLNDMYGD
YKYTYWACGVVLIISGIYLFIGMGINYRLLAKEQKANEQKKESKEEETSIDVAGKPNEVT
KAAESPDQKDTDGGPKEEESPV SEQ ID NO: 96 Cynomolgus Monkey MCT1 protein
MPPAVGGPVGYTPPDGGWGWAVVIGAFISIGFSYAFPKSITVFFKEIESIFHATTSEVSWIS
SIMLA VMYGGGPISSILVNKYGSRIVMIIGGCLSGCGLIAASFCNTVQELYFCIGFVGGLG
LAFNLNPALTMIGKYFYKRRPLANGLAMAGSPVFLCTLAPLNQVFFDIFGWRGSFLILG
GLLLNCCVAGALMRPIGPKPTKAGKDKSKASLQKAGKSGVKKGRHDANTDLIGRHPKR
EKRSVFQTINQFLDLTLFTHRGFLLYLSGNVIMFFGLFAPLVFLSSYGKSQHYSSEKSAFL
LSILAFVDMVARPSMGLVANTKPIRPRIQYFFAASIVANGVCHMLAPLSTTYVGFCVYA
GFFGFAFGWLSSVLFETLMDLVGPQRFSSAVGLVTIVECCPVLLGPPLLGRLSDMYGDY
KYTYWACGVVLIISGIYLFIGMGINYRLLAKEQKANEQKKESKEEETSIDVAGKPKEVTK
AAESPDQKDTEEGPKEEDSPV SEQ ID NO: 97 HCDR1
TXaa$_2$SGRSXaa$_7$TXaa$_9$Xaa$_{10}$HXaa$_{12}$Xaa$_{13}$
Wherein Xaa$_2$ is Valine or Arginine, Xaa$_7$ is Leucine or Arginine,
Xaa$_9$ is Asparagine or Glycine,
Xaa$_{10}$ is Tyrosine or Isoleucine, Xaa$_{12}$ is Leucine or Isoleucine, and
and Xaa$_{13}$ is Glutamine, Valine, or Glycine SEQ ID NO: 98 HCDR2
FIRXaa$_4$SGNTXaa$_9$YNSXaa$_{13}$FKS
Wherein Xaa$_4$ is Arginine or Serine, Xaa$_9$ is Isoleucine or Glutamic Acid, and
Xaa$_{13}$ is Glutamic Acid or Arginine SEQ ID NO: 99 HCDR3
ARNXaa$_4$WXaa$_6$HGTYYSPGYYVMDXaa$_{20}$
Wherein Xaa$_4$ is Arginine or Leucine, and Xaa$_6$ is Histidine or Arginine or
Tyrosine, and Xaa$_{20}$ is Proline or Alanine

---

The invention claimed is:

1. An antibody or antigen binding fragment thereof that specifically binds human MCT1, wherein the antibody comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein:
 a. the HCDR1 comprises SEQ ID NO: 30;
    the HCDR2 comprises SEQ ID NO: 31;
    the HCDR3 comprises SEQ ID NO: 32;
    the LCDR1 comprises SEQ ID NO: 33;
    the LCDR2 comprises SEQ ID NO: 5; and
    the LCDR3 comprises SEQ ID NO: 6;
 b. the HCDR1 comprises SEQ ID NO: 30;
    the HCDR2 comprises SEQ ID NO: 2;
    the HCDR3 comprises SEQ ID NO: 56, SEQ ID NO: 64, SEQ ID NO: 68, or SEQ ID NO: 72;
    the LCDR1 comprises SEQ ID NO: 33;
    the LCDR2 comprises SEQ ID NO: 5; and
    the LCDR3 comprises SEQ ID NO: 6;
 c. the HCDR1 comprises SEQ ID NO: 30;
    the HCDR2 comprises SEQ ID NO: 2;
    the HCDR3 comprises SEQ ID NO: 99;
    the LCDR1 comprises SEQ ID NO: 33;
    the LCDR2 comprises SEQ ID NO: 5; and
    the LCDR3 comprises SEQ ID NO: 6;
 d. the HCDR1 comprises SEQ ID NO: 30;
    the HCDR2 comprises SEQ ID NO: 2;
    the HCDR3 comprises SEQ ID NO: 72;
    the LCDR1 comprises SEQ ID NO: 4;
    the LCDR2 comprises SEQ ID NO: 5; and
    the LCDR3 comprises SEQ ID NO: 6;
 e. the HCDR1 comprises SEQ ID NO: 30;
    the HCDR2 comprises SEQ ID NO: 2;
    the HCDR3 comprises SEQ ID NO: 68;
    the LCDR1 comprises SEQ ID NO: 4;
    the LCDR2 comprises SEQ ID NO: 5; and
    the LCDR3 comprises SEQ ID NO: 6;
 f. the HCDR1 comprises SEQ ID NO: 40, SEQ ID NO: 48, SEQ ID NO: 52, SEQ ID NO: 60, SEQ ID NO: 76, SEQ ID NO: 80 or SEQ ID NO: 84;
    the HCDR2 comprises SEQ ID NO: 2;
    the HCDR3 comprises SEQ ID NO: 32;
    the LCDR1 comprises SEQ ID NO: 33;
    the LCDR2 comprises SEQ ID NO: 5; and
    the LCDR3 comprises SEQ ID NO: 6;
 g. the HCDR1 comprises SEQ ID NO: 97;
    the HCDR2 comprises SEQ ID NO: 2;
    the HCDR3 comprises SEQ ID NO: 32;
    the LCDR1 comprises SEQ ID NO: 33;
    the LCDR2 comprises SEQ ID NO: 5; and
    the LCDR3 comprises SEQ ID NO: 6;
 h. the HCDR1 comprises SEQ ID NO: 30;
    the HCDR2 comprises SEQ ID NO: 44 or SEQ ID NO: 88;
    the HCDR3 comprises SEQ ID NO: 32;
    the LCDR1 comprises SEQ ID NO: 33;
    the LCDR2 comprises SEQ ID NO: 5; and
    the LCDR3 comprises SEQ ID NO: 6; or
 i. the HCDR1 comprises SEQ ID NO: 30;
    the HCDR2 comprises SEQ ID NO: 98;
    the HCDR3 comprises SEQ ID NO: 32;
    the LCDR1 comprises SEQ ID NO: 33;
    the LCDR2 comprises SEQ ID NO: 5; and
    the LCDR3 comprises SEQ ID NO: 6.

2. The antibody or antigen binding fragment thereof of claim 1, wherein:
 the HCDR1 comprises SEQ ID NO: 30;
 the HCDR2 comprises SEQ ID NO: 31;
 the HCDR3 comprises SEQ ID NO: 32;
 the LCDR1 comprises SEQ ID NO: 33;
 the LCDR2 comprises SEQ ID NO: 5; and
 the LCDR3 comprises SEQ ID NO: 6.

3. The antibody or antigen binding fragment thereof of claim 2, wherein the VH comprises SEQ ID NO: 34, and the VL comprises SEQ ID NO: 35.

4. The antibody of claim 2 wherein the antibody comprises a heavy chain (HC) and a light chain (LC), wherein the HC comprises SEQ ID NO: 36 and the LC comprises SEQ ID NO: 37.

5. The antibody binding fragment thereof of claim 2, wherein said fragment is a Fab, Fab', F(ab')2, Fv fragments, scFv, scFab, disulfide-linked Fvs (sdFv), or a Fd fragment, and wherein the fragment comprises the VH of SEQ ID NO: 34, and the VL of SEQ ID NO: 35.

6. The antibody or antigen binding fragment thereof of claim 1, wherein:
the HCDR1 comprises SEQ ID NO: 30;
the HCDR2 comprises SEQ ID NO: 2;
the HCDR3 comprises SEQ ID NO: 56, SEQ ID NO: 64, SEQ ID NO: 68, or SEQ ID NO: 72;
the LCDR1 comprises SEQ ID NO: 33;
the LCDR2 comprises SEQ ID NO: 5; and
the LCDR3 comprises SEQ ID NO: 6.

7. The antibody or antigen binding fragment thereof of claim 6, wherein the VH comprises SEQ ID NO: 57, 65, 69, or 73 and the VL comprises SEQ ID NO: 35.

8. The antibody or antigen binding fragment thereof of claim 1, wherein:
the HCDR1 comprises SEQ ID NO: 30;
the HCDR2 comprises SEQ ID NO: 2;
the HCDR3 comprises SEQ ID NO: 99;
the LCDR1 comprises SEQ ID NO: 33;
the LCDR2 comprises SEQ ID NO: 5; and
the LCDR3 comprises SEQ ID NO: 6.

9. The antibody or antigen binding fragment thereof of claim 8, wherein the VH comprises SEQ ID NO: 57, 65, 69, or 73 and the VL comprises SEQ ID NO: 35.

10. The antibody of claim 8 wherein the antibody comprises a HC and a LC, wherein the HC comprises SEQ ID NO: 58, 66, 70, or 74, and the LC comprises SEQ ID NO: 37.

11. The antibody or antigen binding fragment thereof of claim 1, wherein:
the HCDR1 comprises SEQ ID NO: 30;
the HCDR2 comprises SEQ ID NO: 2;
the HCDR3 comprises SEQ ID NO: 72;
the LCDR1 comprises SEQ ID NO: 4;
the LCDR2 comprises SEQ ID NO: 5; and
the LCDR3 comprises SEQ ID NO: 6.

12. The antibody or antigen binding fragment thereof of claim 11, wherein the VH comprises SEQ ID NO: 73, and the VL comprises SEQ ID NO: 8.

13. The antibody of claim 11, wherein the antibody comprises a HC and a LC, wherein the HC comprises SEQ ID NO: 74 and the LC comprises SEQ ID NO: 10.

14. The antibody or antigen binding fragment thereof of claim 1, wherein:
the HCDR1 comprises SEQ ID NO: 30;
the HCDR2 comprises SEQ ID NO: 2;
the HCDR3 comprises SEQ ID NO: 68;
the LCDR1 comprises SEQ ID NO: 4;
the LCDR2 comprises SEQ ID NO: 5; and
the LCDR3 comprises SEQ ID NO: 6.

15. The antibody or antigen binding fragment thereof of claim 14, wherein the VH comprises SEQ ID NO: 69, and the VL comprises SEQ ID NO: 8.

16. The antibody of claim 14, wherein the antibody comprises a HC and a LC, wherein the HC comprises SEQ ID NO: 70 and the LC comprises SEQ ID NO: 10.

17. The antibody or antigen binding fragment thereof of claim 1, wherein:
the HCDR1 comprises SEQ ID NO: 40, SEQ ID NO: 48, SEQ ID NO: 52, SEQ ID NO: 60, SEQ ID NO: 76, SEQ ID NO: 80 or SEQ ID NO: 84;
the HCDR2 comprises SEQ ID NO: 2;
the HCDR3 comprises SEQ ID NO: 32;
the LCDR1 comprises SEQ ID NO: 33;
the LCDR2 comprises SEQ ID NO: 5; and
the LCDR3 comprises SEQ ID NO: 6.

18. The antibody or antigen binding fragment thereof of claim 17, wherein the VH comprises SEQ ID NO: 41, 49, 53, 61, 77, 81 or 85 and the VL comprises SEQ ID NO: 35.

19. The antibody or antigen binding fragment thereof of claim 1, wherein:
the HCDR1 comprises SEQ ID NO: 97;
the HCDR2 comprises SEQ ID NO: 2;
the HCDR3 comprises SEQ ID NO: 32;
the LCDR1 comprises SEQ ID NO: 33;
the LCDR2 comprises SEQ ID NO: 5; and
the LCDR3 comprises SEQ ID NO: 6.

20. The antibody or antigen binding fragment thereof of claim 19, wherein the VH comprises SEQ ID NO: 41, 49, 53, 61, 77, 81 or 85 and the VL comprises SEQ ID NO: 35.

21. The antibody of claim 19, wherein the antibody comprises a HC and a LC, wherein the HC comprises SEQ ID NO: 42, 50, 54, 62, 78, 82, or 86, and the LC comprises SEQ ID NO: 37.

22. The antibody or antigen binding fragment thereof of claim 1, wherein:
the HCDR1 comprises SEQ ID NO: 30;
the HCDR2 comprises SEQ ID NO: 44 or SEQ ID NO: 88;
the HCDR3 comprises SEQ ID NO: 32;
the LCDR1 comprises SEQ ID NO: 33;
the LCDR2 comprises SEQ ID NO: 5; and
the LCDR3 comprises SEQ ID NO: 6.

23. The antibody or antigen binding fragment thereof of claim 22, wherein the VH comprises SEQ ID NO: 45 or 89, and the VL comprises SEQ ID NO: 35.

24. The antibody or antigen binding fragment thereof of claim 1, wherein:
the HCDR1 comprises SEQ ID NO: 30;
the HCDR2 comprises SEQ ID NO: 98;
the HCDR3 comprises SEQ ID NO: 32;
the LCDR1 comprises SEQ ID NO: 33;
the LCDR2 comprises SEQ ID NO: 5; and
the LCDR3 comprises SEQ ID NO: 6.

25. The antibody or antigen binding fragment thereof of claim 24, wherein the VH comprises SEQ ID NO: 45 or 89, and the VL comprises SEQ ID NO: 35.

26. The antibody of claim 24, wherein the antibody comprises a HC and a LC, wherein the HC comprises SEQ ID NO: 46 or 90, and the LC comprises SEQ ID NO: 37.

27. An antibody or antigen binding fragment thereof, comprising a heavy chain variable region (VH) and a light chain variable region (VL), wherein the VH comprises SEQ ID NO: 7, 18, 21, or 27, and the VL comprises SEQ ID NO: 8, 13, or 22.

28. The antibody or antigen binding fragment thereof of claim 27, comprising a heavy chain variable region (VH) and a light chain variable region (VL), wherein:
a. the VH comprises SEQ ID NO: 7 and the VL comprises SEQ ID NO: 8;
b. the VH comprises SEQ ID NO: 7 and the VL comprises SEQ ID NO: 13;
c. the VH comprises SEQ ID NO: 18 and the VL comprises SEQ ID NO: 13;
d. the VH comprises SEQ ID NO: 21 and the VL comprises SEQ ID NO: 22; or
e. the VH comprises SEQ ID NO: 27 and the VL comprises SEQ ID NO: 22.

29. An antibody comprising a heavy chain (HC) and a light chain (LC), wherein the HC and the LC comprise the following amino acid sequences:
a. the HC comprises SEQ ID NO: 9 and the LC comprises SEQ ID NO: 10;

b. the HC comprises SEQ ID NO: 9 and the LC comprises SEQ ID NO: 15;
c. the HC comprises SEQ ID NO: 19 and the LC comprises SEQ ID NO: 15;
d. the HC comprises SEQ ID NO: 23 and the LC comprises SEQ ID NO: 24; or
e. the HC comprises SEQ ID NO: 28 and the LC comprises SEQ ID NO: 24.

30. The antibody or antigen binding fragment thereof of claim 1, wherein the antibody comprises a human IgG1 isotype.

31. The antibody or antigen binding fragment thereof of claim 30, wherein the human IgG1 is effector null.

32. An antibody produced by a process of culturing a cell comprising a vector having a nucleic acid sequence encoding SEQ ID NO: 9, 19, 23, 28, 36, 42, 46, 50, 54, 58, 62, 66, 70, 74, 78, 82, 86, 90, 10, 15, or 37 under conditions such that the antibody is expressed and recovering the expressed antibody from the culture medium.

33. An antibody produced by a process of culturing a cell comprising a first vector having a nucleic acid sequence encoding SEQ ID NO: 9, 19, 23, 28, 36, 42, 46, 50, 54, 58, 62, 66, 70, 74, 78, 82, 86, or 90, and a second vector comprising a nucleic acid sequence encoding SEQ ID NO: 10, 15, 24, or 37 under conditions such that the antibody is expressed and recovering the expressed antibody from the culture medium.

34. A pharmaceutical composition comprising the antibody of claim 1, and a pharmaceutically acceptable excipient, diluent, or carrier.

* * * * *

UNITED STATES PATENT AND TRADEMARK OFFICE
CERTIFICATE OF CORRECTION

PATENT NO. : 11,987,624 B2
APPLICATION NO. : 17/932039
DATED : May 21, 2024
INVENTOR(S) : Frank Charles Dorsey et al.

It is certified that error appears in the above-identified patent and that said Letters Patent is hereby corrected as shown below:

On the Title Page

Column 1; Line 1; Assignee: Delete "lmmunometabolism" and insert -- Immunometabolism --.

Column 2; Line 1; U.S. Patent Documents: Delete "Broeks" and insert -- Brooks --.

Column 2; Line 1-2; Other Publications: After "Report" delete "and Search Report,".

In the Claims

Column 130; Line 65; Claim 5: After "antibody" insert -- or antigen --.

Column 133; Line 29; Claim 34: Delete "1," and insert -- 1 --.

Signed and Sealed this
Third Day of September, 2024

Katherine Kelly Vidal
*Director of the United States Patent and Trademark Office*